United States Patent
Afargan

(10) Patent No.: US 10,987,402 B2
(45) Date of Patent: *Apr. 27, 2021

(54) PHARMACEUTICAL COMPOSITIONS OF WATER SOLUBLE PEPTIDES WITH POOR SOLUBILITY IN ISOTONIC CONDITIONS AND METHODS FOR THEIR USE

(71) Applicant: STRONGBRIDGE DUBLIN LIMITED, Dublin (IE)

(72) Inventor: Michel Afargan, Ra'anana (IL)

(73) Assignee: Strongbridge Dublin Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/512,536

(22) Filed: Jul. 16, 2019

(65) Prior Publication Data

US 2019/0336567 A1 Nov. 7, 2019

Related U.S. Application Data

(63) Continuation of application No. 15/984,646, filed on May 21, 2018, now Pat. No. 10,398,751, which is a
(Continued)

(51) Int. Cl.
*A61K 38/08* (2019.01)
*A61K 9/50* (2006.01)
(Continued)

(52) U.S. Cl.
CPC ............ *A61K 38/08* (2013.01); *A61K 9/0019* (2013.01); *A61K 9/107* (2013.01); *A61K 9/127* (2013.01);
(Continued)

(58) Field of Classification Search
CPC .. A61K 9/5015; A61K 9/5021; A61K 9/5036; A61K 9/5052; A61K 38/08; A61K 47/18; A61K 47/183
See application file for complete search history.

(56) References Cited

U.S. PATENT DOCUMENTS

| 4,235,886 A | 11/1980 | Freidinger et al. |
| 4,310,518 A | 1/1982 | Freidinger et al. |
| (Continued) | | |

FOREIGN PATENT DOCUMENTS

| CN | 104740599 | 7/2015 |
| EP | 1098660 | 10/2002 |
| (Continued) | | |

OTHER PUBLICATIONS

Afargan et al., Novel long acting somatostatin analog with endocrine selectivity:potent suppression of growth hormonebut not of insulin. Endocrinology vol. 142, 1, p. 477-486 (Year: 2001).*
(Continued)

*Primary Examiner* — Lakshmi S Channavajjala
(74) *Attorney, Agent, or Firm* — Reed Smith LLP; Robert R. Riddle; Hallie H. Wimberly

(57) ABSTRACT

The present invention provides compositions comprising water soluble peptides with poor solubility in isotonic solutions which exhibit enhanced bioavailability with reduced adverse effects including injection site reactions. Methods are also disclosed for using such compositions for the treatment of diseases including, but not limited to, cancer, type 2 diabetes, acromegaly, metabolic disorders, endocrine disorders, exocrine tumors, and hormone-related tumors. Methods to reduce adverse injection site reactions and improve bioavailability are also disclosed.

19 Claims, 17 Drawing Sheets

Related U.S. Application Data continuation of application No. 15/487,731, filed on Apr. 14, 2017, now Pat. No. 10,039,801, which is a continuation of application No. PCT/IB2017/000194, filed on Feb. 16, 2017.

(60) Provisional application No. 62/295,545, filed on Feb. 16, 2016.

(51) Int. Cl.
*A61K 9/00* (2006.01)
*A61K 9/107* (2006.01)
*A61K 9/127* (2006.01)
*A61K 47/12* (2006.01)
*A61K 47/36* (2006.01)

(52) U.S. Cl.
CPC .......... *A61K 9/5031* (2013.01); *A61K 9/5089* (2013.01); *A61K 47/12* (2013.01); *A61K 47/36* (2013.01)

(56) References Cited

U.S. PATENT DOCUMENTS

| | | | |
|---|---|---|---|
| 6,270,700 | B1 | 8/2001 | Ignatious |
| 6,406,719 | B1 | 6/2002 | Farrar et al. |
| 6,998,393 | B2 | 2/2006 | Jin et al. |
| 7,674,767 | B2 | 3/2010 | Pai et al. |
| 8,137,697 | B1 | 3/2012 | Sung et al. |
| 8,906,417 | B2 | 12/2014 | Lippard et al. |
| 9,439,864 | B2 | 9/2016 | Sebring |
| 10,039,801 | B2 * | 8/2018 | Afargan ............. A61K 9/107 |
| 2002/0009493 | A1 | 1/2002 | Schwendeman et al. |
| 2002/0094964 | A1 | 7/2002 | Chen et al. |
| 2003/0108743 | A1 | 6/2003 | Anderson |
| 2006/0121121 | A1 | 6/2006 | Jin et al. |
| 2007/0009605 | A1 | 1/2007 | Ignatious |
| 2009/0305995 | A1 | 12/2009 | Krawinkler et al. |
| 2010/0015184 | A1 | 1/2010 | Tuel |
| 2010/0247668 | A1 | 9/2010 | Eliasof et al. |
| 2011/0229580 | A1 | 9/2011 | Srivastava et al. |
| 2011/0293690 | A1 | 12/2011 | Griffin et al. |
| 2012/0021018 | A1 | 1/2012 | Woo |
| 2012/0052097 | A1 | 3/2012 | Fetzer et al. |
| 2012/0302505 | A1 | 11/2012 | Fetzer et al. |
| 2013/0142878 | A1 | 6/2013 | Rubsamen et al. |
| 2013/0171245 | A1 | 7/2013 | Imran et al. |
| 2013/0202659 | A1 | 8/2013 | Crawford et al. |
| 2014/0161892 | A1 | 6/2014 | Salman et al. |
| 2014/0377366 | A1 | 12/2014 | Krebs |
| 2015/0164805 | A1 | 6/2015 | Schwendeman et al. |
| 2015/0258195 | A1 | 9/2015 | Almutairi et al. |
| 2016/0193285 | A1 | 7/2016 | Haviv |

FOREIGN PATENT DOCUMENTS

| | | | |
|---|---|---|---|
| EP | 2389928 | 11/2011 | |
| EP | 2667844 | 12/2013 | |
| EP | 2787979 | 10/2014 | |
| PT | 1085896 | 8/2007 | |
| WO | 2010033207 | 3/2010 | |
| WO | WO-2010033207 A1 * | 3/2010 | ............ A61K 47/48 |
| WO | 2011087496 | 7/2011 | |
| WO | 2016004048 | 1/2016 | |

OTHER PUBLICATIONS

Wang et al., "Mechanistic evaluation of the glucose-induced reduction in initial burst release of octreotide acetate from poly(d,l-lactide-co-glycolide) microspheres", Biomaterials 25 (2004) 1919-1927.

Afargan et al., "Novel Long-Acting Somatostain Analog with Endocrine Selectivity: Potent Suppression of Growth Hormone But Not of Insulin", Endocrinology, 142:1 (2001) 477-486.

Lamberts, "The Role of Somatostatin in the Regulation of Anterior Pituitary Hormone Secretion and the Use of Its Analogs in the Treatment of Human Pituitary Tumors", Endocrine Reviews, 9:4 (1988) 417-436.

Rodrigues et al., "The Effect of Cyclodextrins on the In Vitro and In Vivo Properties of Insulin-Loaded Poly (D,L-Lactic-Co-Glycolic Acid) Microspheres", Artificial Organs, 27(5):492-497.

Ungaro et al., "Insulin-loaded PLGA/cyclodextrin large porous particles with improved aerosolization properties: In vivo deposition and hypoglycaemic activity after delivery to rat lungs", Journal of Controlled Release 135 (2009) 25-34.

Aguiar et al., "Encapsulation of insulin—cyclodextrin complex in PLGA microspheres: a new approach for prolonged pulmonary insulin delivery", J. Microencapsulation, Aug. 2004, vol. 21, No. 5, 553-564.

Mansour et al., "Materials for Pharmaceutical Dosage Forms: Molecular Pharmaceutics and Controlled Release Drug Delivery Aspects", Int. J. Mol. Sci. 2010,11, 3298-3322.

Emami et al., "A Novel Approach to Prepare Insulin-Loaded Poly (Lactic-Co-Glycolic Acid) Microcapsules and the Protein Stability Study", Journal of Pharmaceutical Sciences, vol. 98, No. 5, May 2009, 1712-1731.

La Salle et al., "PLA Nano- and Microparticles for Drug Delivery: An Overview of the Obtension Methods", Macromol. Biosci. 2007, 7, 767-783.

International Search Report and Written Opinion, dated Jun. 8, 2017, in corresponding International Patent Application No. PCT/IB2017/000194.

Koch "Pharmacotherapy: Somatoprim versus octreotide in acromegaly", Nature Reviews Endocrinology, vol. 8, No. 2, Nov. 29, 2011, p. 66.

Melmed "New therapeutic agents for acromegaly", Nature Reviews Endocrinology, vol. 12, pp. 90-98, Nov. 27, 2015.

Plockinger et al. "DG3173 (somatoprim), a unique somatostatin receptor subtypes 2-, 4- and 5-selective analogue, effectively reduces GH secretion in human GH-secreting pituitary adenomas even in Octreotide non-responsive tumours", European Journal of Endocrinology, vol. 166, No. 2, Nov. 7, 2011, pp. 223-234.

\* cited by examiner

PHARMACEUTICAL COMPOSITIONS OF WATER SOLUBLE PEPTIDES WITH POOR SOLUBILITY IN ISOTONIC CONDITIONS AND METHODS FOR THEIR USE

[1] The present application is a Continuation of U.S. patent application Ser. No. 15/984,646 filed on May 21, 2018, now U.S. Pat. No. 10,398,751, which is a continuation of U.S. patent application Ser. No. 15/487,731, now U.S. Pat. No. 10,039,801, filed on Apr. 14, 2017 which is a continuation of International Application No. PCT/IB17/00194 filed on Feb. 16, 2017 which claims the benefit of U.S. Provisional Application No. 62/295,545 filed on Feb. 16, 2016, the contents of which are incorporated herein by reference.

The present disclosure is directed to pharmaceutical compositions and methods for using such pharmaceutical compositions comprising peptides or pharmaceutically acceptable salts thereof wherein the peptide is water soluble, but has low solubility in physiological conditions.

FIELD OF THE INVENTION

Background of the Invention

The major problem which hinders the use of linear peptides as drugs is related to the fact that such peptides exist in a rapid equilibrium between multiple conformations while only very few of these conformations are bioactive. This flexibility leads to poor selectivity, rapid proteolytic digestion and low bioavailability. One of the best ways to overcome this problem is by cyclization, which introduces conformational constraint into peptides.

In naturally occurring cyclic peptides, cyclization links together specific side chains and/or terminal groups in the peptide. These modes of cyclization, referred to as classical modes of cyclization, are highly limited due to the small number of amino acid side chains and peptide termini which lend themselves to cyclization. Thus, the diversity of possible constrained "classical" cyclic analogs of a given sequence is small.

Backbone cyclization overcomes these limitations (Afargan et al., *Novel Long-Acting Somatostain Analog with Endocrine Selectivity: Potent Suppression of Growth Hormone But Not of Insulin*, Endocrinology, 142:1 (2001) 477-486). Applying this technology, cyclization takes place by a covalent interconnection of one or more α-nitrogen(s) in the peptide backbone to one another or to the amino or carboxy termini or to a side chain.

Somatostatin is a cyclic tetradecapeptide found both in the central nervous system and in peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (See Lamberts, *Endocrine Rev.*, 9:427, 1988). Additionally, somatostatin and its analogs are potentially useful antiproliferative agents for the treatment of various types of tumors.

In its natural form, somatostatin has limited use as a therapeutic agent since it exhibits two undesirable properties: poor bioavailability and short duration of action. For this reason, great efforts have been made during the last two decades to find somatostatin analogs that have superiority in either potency, biostability, duration of action or selectivity with regard to inhibition of the release of growth hormone, insulin or glucagon.

A group of somatostatin analogs (U.S. Pat. Nos. 4,310,518 and 4,235,886) includes Octreotide, the first approved somatostatin analog clinically available.

Another somatostain analog is veldoreotide (formerly known as PTR 3173 or DG3173), a conformationally-constrained, backbone-cyclic synthetic peptide, which is depicted in FIG. 1 and is as follows:
-γ-Abu-Phe-Trp-D-Trp-Lys-Thr-Phe-N-carbamoylmethyl
where Abu is aminobutyryl.

Veldoreotide acetate is more commonly described as Cyclo(γ-aminobutyryl-L-phenylalanyl-L-tryptophanyl-D-tryptophanyl-L-lysyl-L-threonyl-L-phenylalanyl-N-carbamoylmethyl-γ-aminobutyryl), acetate salt or Cyclo(-γ-Abu-Phe-Trp-D-Trp-Lys-Thr-Phe-N-carbamoylmethyl-γ-Abu), acetate salt.

Octreotide and veldoreotide have similar solubility in distilled water for injection, but very different solubility under physiological conditions. Once veldoreotide acetate progressed to human studies, it was found that, although veldoreotide acetate has the same receptor affinity for GH inhibition as Octreotide, an increased dose was required for the same pharmacological effect, when both were injected in lactic acid buffer. Upon investigating the cause of this problem, it was discovered that veldoreotide acetate is poorly soluble is physiological conditions, leading to "flip-flop" pharmacokinetics. Previous studies with veldoreotide acetate have found that injection of a solution of veldoreotide acetate results in adverse injection site reactions and limited bioavailability due to its relatively low solubility in isotonic solutions. Therefore, methods for enhancing the solubility of veldoreotide acetate in physiological (isotonic) solutions are needed.

SUMMARY

The present disclosure aims to provide formulations that enhance the solubility and dispersion of injectable peptides or pharmaceutically acceptable salts thereof, improve bioavailability and distribution, and reduce adverse reactions at an injection site.

Regardless of the theories and mechanisms discussed herein in this disclosure, the spirit of the invention encompasses the improved physiochemical and pharmacokinetic properties and use of compositions described herein regardless of the actual mechanism.

In one embodiment (Embodiment 1), a pharmaceutical composition comprises: a peptide or a pharmaceutically acceptable salt thereof, wherein the peptide or the pharmaceutically acceptable salt thereof is freely soluble in deionized water with a solubility in deionized water of from 100 to 350 mg/ml but is slightly soluble under physiological conditions, or otherwise in solutions with chloride ions, with a solubility of 2-3 mg/ml and the peptide or the pharmaceutically acceptable salt precipitates by salting out at a concentration greater than 3 mg/ml; a pharmaceutically acceptable carrier or diluent; and an excipient, wherein the excipient is a cyclic polysaccharide or dextrose or a combination thereof.

It certain embodiments, the unique surface activity properties of veldoreotide are utilized. For example, veldoreotide reduces the surface tension of water by more than 30% and its unique amphiphilic properties are consistent with its use as a surfactant. This reduction in surface tension is partially alleviated by the addition of dextrose or cyclic polysaccharide.

Thus, a composition comprising veldoreotide and either dextrose or cyclic polysaccharide in a carrier or diluent is provided, wherein the surface tension of the composition is from about 60% to about 80% of the carrier alone. In other embodiments, the surface tension of the composition is from about 40 dynes/cm to about 60 dynes/cm as measured at a temperature of 5° C.

The invention also provides a process for manufacturing polymeric microspheres comprising the steps of:

(i) mixing an excipient comprising a cyclic polysaccharide or dextrose or a combination thereof, and a peptide or a pharmaceutically acceptable salt thereof in water to form a first aqueous mixture, wherein the peptide or the pharmaceutically acceptable salt thereof is freely soluble in deionized water with a solubility in deionized water of from 100 to 350 mg/ml but is slightly soluble under physiological conditions, or otherwise in solutions with chloride ions, with a solubility of 2-3 mg/ml and the peptide or the pharmaceutically acceptable salt precipitates by salting out at a concentration greater than 3 mg/ml;

(ii) mixing a polymer in organic solvent such as dichloromethane to form a polymeric solution;

(iii) mixing the first aqueous mixture in the polymeric organic solution to form a first dispersion mixture comprising a water in oil primary emulsion;

(iv) mixing polyvinyl alcohol (PVA) in an amount of 0.1 to 3 weight % in phosphate buffer saline or in saline to form a second aqueous mixture;

(v) mixing the primary emulsion in the second aqueous mixture of PVA to form a double emulsion of water-in-oil-in-water to provide a secondary dispersion mixture;

(vi) allowing the organic solvent in the secondary dispersion mixture to evaporate to form solid polymeric microspheres, wherein the peptide or pharmaceutically acceptable salt thereof is encapsulated in the polymeric microspheres;

(vii) washing and isolating the polymeric microspheres; and (viii) drying the microspheres under control conditions with or without the addition of a surfactant and mannitol mixture during the drying process.

The invention also provides an extended-release pharmaceutical composition produced by the process of above. In this embodiment, a plurality of polymeric microspheres comprising veldoreotide is provided, wherein the polymeric microspheres have a surface area of from about 7 m$^2$/g to about 12 m$^2$/g as measured by, for example, the Brunauer-Emmett-Teller (BET) method. In certain embodiments, the plurality of polymeric microspheres have a mean diameter of from about 10 μm to about 100 μm and more preferably in the range of from about 10 μm to about 30 μm. In certain embodiments, the polymeric microspheres may comprise very small amounts of dextrose, such as from about 0.1% wt to about 1% wt of the total weight of the polymeric microspheres. In other embodiments, the polymeric microspheres may comprise a cyclic polysaccharide from about 1% wt to about 10% wt of the total weight of the polymeric microspheres, and more preferably from about 2.5% wt to about 5% wt. In certain embodiments, veldoreotide comprises from about 10% wt to about 30% wt of the total weight of the polymeric microspheres, and more preferably from about 15% wt to about 20% wt.

The invention also provides a composition for manufacturing polymeric microspheres comprising: veldoreotide or a pharmaceutically acceptable salt thereof; an excipient comprising a cyclic polysaccharide or dextrose or a combination thereof; and a polymer.

The invention also provides a method for treating a disease or condition selected from the group consisting of acromegaly, acromegaly cancer, SST-R5 expressing tumors, type 2 diabetes, hyperglycemia, carcinoid tumors, Cushing's Syndrome, and hormone-related tumors comprising the step of administering the pharmaceutical composition of any one of claims 1-37 to a patient with said disease or condition.

DESCRIPTION OF THE DRAWINGS AND FIGURES

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
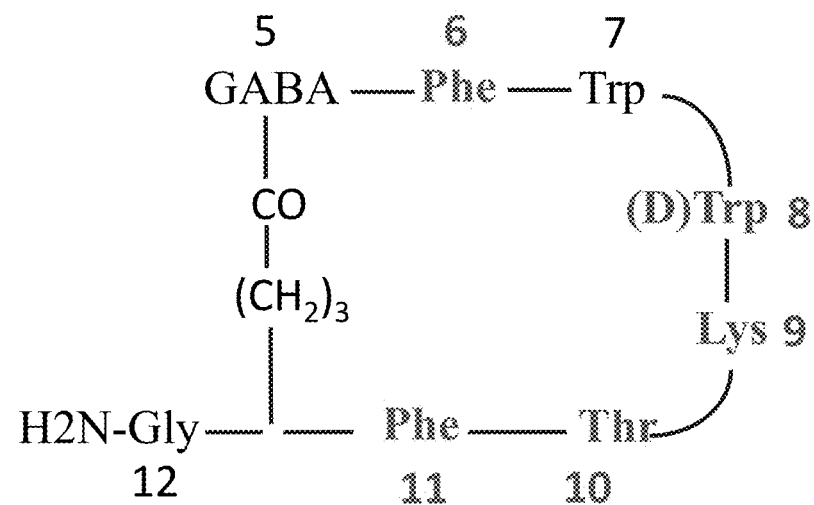
FIG. 1 depicts the chemical structure of veldoreotide.
Figure 1:
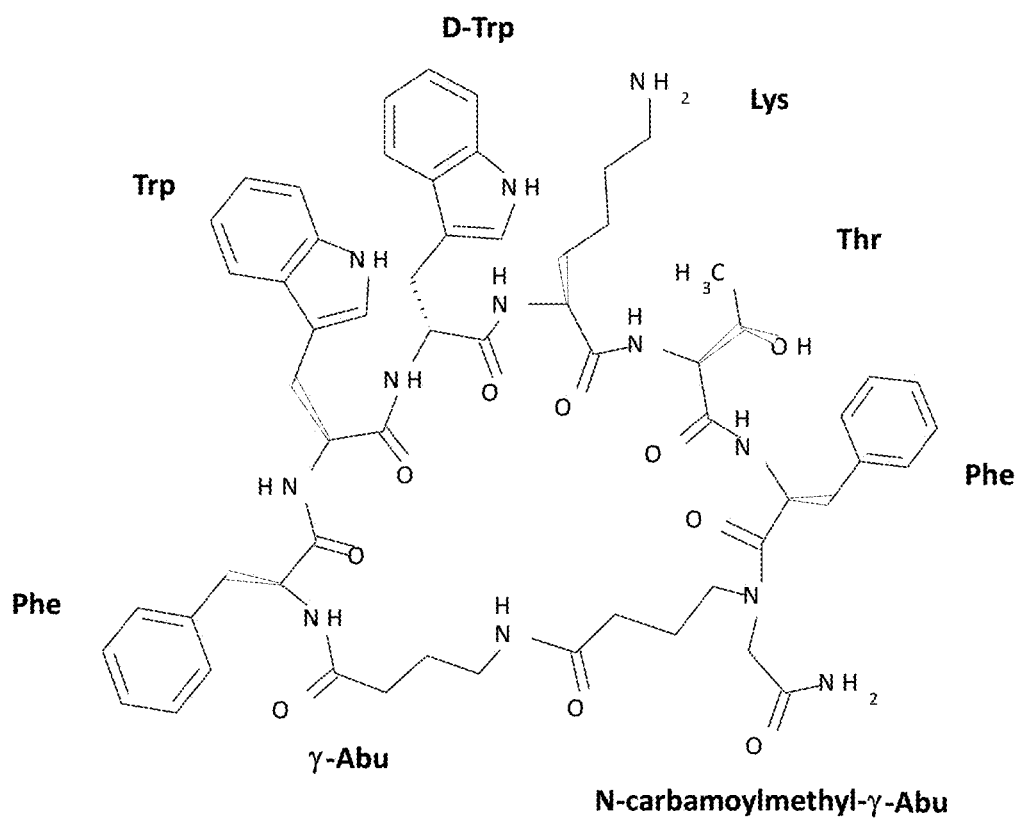

All patents and publications cited herein are incorporated by reference in their entirety, including any references cited therein.

"Polymer" as used herein refers to any type of polymer including, for example, a homopolymer, a copolymer, a block copolymer, a random copolymer, and the like. Unless stated to the contrary, species described herein comprise all possible individual isomers, e.g., each enantiomer and diastereomer, and a mixture of isomers, such as a racemic or scalemic mixtures. Enantiomeric species may exist in different isomeric or enantiomeric forms. Unless otherwise specified, enantiomeric species discussed herein without reference to their isomeric form shall include all various isomeric forms as well as racemic mixtures of isomeric forms. For example, reference to lactic acid shall herein include L-lactic acid, D-lactic acid, and racemic mixtures of the L- and D-isomers of lactic acid; reference to lactide shall herein include L-lactide, D-lactide, and DL-lactide (where DL-lactide refers to racemic mixtures of the L- and D-isomers of lactide); similarly, reference to poly(lactide) shall herein include poly(L-lactide), poly(D-lactide) and poly (DL-lactide); similarly, reference to poly(lactide-co-glycolide) will herein include poly(L-lactide-co-glycolide), poly(D-lactide-co-glycolide), and poly(DL-lactide-co-glycolide).

As used herein, the term "physiological conditions" refers to a condition normally present in mammalian (e.g. mouse, rat or human) bodies, such as a solution that contains solutes, (e.g. salts comprising chloride ions) at concentrations equivalent to those found in mammalian bodily fluids. The term "isotonic" as used herein refers to fluids a solution having the same osmotic pressure as some other solution, especially one in a cell or a body fluid. In some instances, an isotonic solution has the same concentration of solutes as the blood, such as an isotonic saline solution.

As used herein, the term "veldoreotide" is a cyclic polymer also known as cyclo(-γ-aminobutyryl-L-phenylalanyl-L-tryptophanyl-D-tryptophanyl-L-lysyl-L-threonyl-L-phenylalanyl-N-carbamoylmethyl-γ-aminobutyryl). It is also known as "COR-005", "COR005", used interchangeably herein. It was previously known as PTR 3173 or DG3173. The terms "veldoreotide acetate" "COR-005 acetate", "COR005 acetate", used interchangeably herein, refer to the monoacetate salt of veldoreotide.

The present invention combines conformationally-constrained, backbone-cyclic synthetic peptide analogs with excipients to increase solubility in isotonic solutions as well as to increase absorption and bioavailability when such peptides are delivered by injection. The present invention also discloses formulations of conformationally-constrained, backbone-cyclic synthetic peptide analogs with or without excipients which demonstrate improved pharmacokinetics and reduced injection site reactions.

Compositions of the invention may be used in methods of the invention for the treatment of various diseases including, but not limited to, cancer, type 2 diabetes, acromegaly and hormone-related tumors.

The pharmaceutical composition may comprise a peptide or a pharmaceutically acceptable salt thereof, wherein the peptide is water soluble, but has low solubility in isotonic conditions, a polymer, and optionally, an excipient, wherein the excipient is a hydrophobic scavenger, a sugar or an amino acid.

The pharmaceutical composition may comprise a peptide or a pharmaceutically acceptable salt thereof, wherein the peptide is water soluble, but has low solubility in isotonic conditions, a polymer forming microspheres, and optionally, an excipient, wherein the excipient is a hydrophobic scavenger, a sugar or an amino acid.

The pharmaceutical composition may comprise a peptide or a pharmaceutically acceptable salt thereof, wherein the peptide is water soluble, but has low solubility in isotonic conditions, a polymer forming microspheres, wherein the polymer is PLGA, and optionally, an excipient, wherein the excipient is a hydrophobic scavenger, a sugar or an amino acid.

The pharmaceutical composition may comprise a peptide or a pharmaceutically acceptable salt thereof, wherein the peptide is water soluble, but has low solubility in isotonic conditions, a polymer, and an excipient, wherein the pharmaceutical composition forms a gel.

The pharmaceutical composition may form an emulsion comprises a peptide or a pharmaceutically acceptable salt thereof, wherein the peptide is water soluble, but has low solubility in isotonic conditions, an oil phase, an aqueous phase, and optionally, an excipient, wherein the excipient is a hydrophobic scavenger, a sugar or an amino acid, wherein the pharmaceutical composition is an emulsion.

The pharmaceutical composition may comprise a peptide or pharmaceutically acceptable salt thereof, wherein the peptide is water soluble, but has low solubility in isotonic conditions, a pharmaceutically acceptable carrier or diluent, a liposomal agent forming liposomes, and optionally, an excipient wherein the excipient is a hydrophobic scavenger, a sugar or an amino acid.

Peptides or pharmaceutically acceptable salts thereof in any of the embodiments may be cyclic peptides, peptide amphiphiles, ionic, water soluble surfactants, somatostatin analogs, cyclic somatostatin analogs, conformationally-constrained, backbone-cyclic peptides, conformationally constrained, backbone-cyclic somatostatin analogs, conformationally-constrained, backbone-cyclic single amine somatostatin analogs, veldoreotide and pharmaceutically acceptable salts thereof, for example, veldoreotide acetate. The peptide or pharmaceutically acceptable salt thereof may act as a water in oil emulsifier and have a hydrophilic lipophilic balance of between 3 and 8.

Pharmaceutically acceptable salts may be hydrochloride, hydrobromide, sulfate, phosphate, acetate, trifluoroacetate, citrate, oxalate, malonate, salicylate, p-aminosalicylate, malate, fumarate, succinate, ascorbate, maleate, sulfonate, phosphonate, perchlorate, nitrate, formate, propioniate, gluconate, lactate, tartrate, pamoate, hydroxymaleate, pyruvate, phenylacetate, benzoate, p-aminobenzoate, p-hydroxybenzoate, methanesulfonate, ethanesulfonate, nitrite, hydroxyethanesulfonate, ethylenesulfonate, p-toluenesulfonate, naphthylsulfonate, sulfanilate, camphersulfonate, mandelate, o-methylmandelate, hydrogen-benzesulfonate, picrate, adipate, D-o-tolyltartrate, tartronate, α-toluate, (o, m, p)-toluate, napthylamine sulfonate, octanoate, palmitate, stearate, fatty acid salt, other mineral acid salt, and carboxylic acids.

The sugar of the may be a monosaccharide, disaccharide, polysaccharide, cyclic polysaccharide, cyclodextrin, β-cyclodextrin, hydroxypropyl-β-cyclodextrin, or dextrose. Dextrose may be present at about 2.5% by weight of the composition. The amino acid may be any amino acid, including lysine or arginine, or pharmaceutically acceptable salts thereof, such as a hydrochloride salt, for example, L-lysine hydrochloride or L-arginine hydrochloride. Hydrophobic scavengers may have at least one free amine group.

The pharmaceutically acceptable carriers or diluents may include isotonic acetate buffer, lactic acid, saline, and phosphate buffered saline. The pharmaceutically acceptable carrier may be at a concentration of about 0.45% by weight of the composition, for example, 0.45% saline.

Polymers may include polymers that form a matrix, that form particles, that form microspheres, that form a gel, and that are biocompatible. The polymer may include poly lactic-co-glycolic acid (PLGA) or carboxymethylcellulose. Polymers forming microspheres may include PLGA. The PLGA may comprise a 50:50 ratio of lactic acid to glycolic acid. Polymers forming a gel may include cellulose gums and their derivatives, such as carboxymethylcellulose. Polymers used for forming a gel may be characterized as viscosity modifying agents, thickeners and gelling agents (gellants). Such agents increase the viscosity of fluids to which they are added and may form gels. Such polymers may have an average viscosity of 1500-3000 cps in a 1% aqueous solution. Such polymers may also interact with the peptide or pharmaceutically acceptable salt thereof and a cyclodextrin to form a gel.

Liposomal agents forming liposomes may include any pharmaceutically acceptable liposomal agent including phosphatidylcholine and derivatives thereof, such as 1,2-dimyristoyl-sn-glycero-3-phosphocholine (DMPC), HSPC, cholesterol, DSPG, DOPC, DPPG, LIPOVA-E120, LECIVA-S70, LECIVA-S90, egg PG, MPEG-DSPE, soybean oil, polysorbate-80, egg sphingomyelin, and phosphatidylcholine.

Pharmaceutical compositions as described herein wherein the polymer forms microspheres may have increased porosity, increased surface area, increased peptide release, increased release of the peptide during a first 24-hour period after injection of the pharmaceutical composition in a patient as compared to microspheres without the excipient. Pharmaceutical compositions wherein the polymer forms microspheres may also exhibit a sustained release profile for at least one, two or four week after injection of the pharmaceutical composition in a patient. Additionally, polymers may encapsulate the excipient, the peptide or pharmaceutically acceptable salt thereof or both the excipient and the peptide or pharmaceutically acceptable salt thereof and the peptide or pharmaceutically acceptable salt thereof and the excipient may be co-localized within the polymer. Polymers of the foregoing embodiments may also have an average molecular weight between about 7 and about 17 kilodaltons or 38 and 54 kilodaltons.

Pharmaceutical compositions may be injectable by a small gauge needle as small as 27G.

The oil phase may include cottonseed or oil or any pharmaceutically acceptable oil. The aqueous phase of the foregoing embodiments may include water or any pharmaceutically acceptable aqueous vehicle. Pharmaceutical compositions may form an emulsion that is a water-in-oil emulsion. The ratio of the oil phase to the aqueous phase may be between 50.1:49.9 and 99.9:0.01. The ratio of the oil phase to the aqueous phase may be 80:20. In pharmaceutical compositions forming an emulsion, the peptide or pharmaceutically acceptable salt thereof may act as in emulsifier in a concentration of about 1% weight/volume.

Pharmaceutical compositions comprising the liposomal agent may exhibit a slow release profile of the peptide or pharmaceutically acceptable salt thereof for at least 48 hours. The slow release profile may comprise therapeutically effective plasma concentration of the peptide or pharmaceutically acceptable salt thereof for at least 48 hours.

It is to be understood that the embodiments herein may employ any potential combination of the components disclosed. For example, a pharmaceutical composition may include any possible combination of the peptide or pharmaceutically acceptable salt thereof, the pharmaceutically acceptable carrier or diluent and the excipient.

In certain aspects, a method for reducing injection site side effects in a patient as compared to injection with an excipient comprises formulating the pharmaceutical compositions of the embodiments herein with the excipient and administering the pharmaceutical composition to said patient by injection. In some embodiments a method for increasing the bioavailability of the peptide or pharmaceutically acceptable salt thereof comprises formulating the pharmaceutical compositions of the foregoing embodiments with the excipient and administering the pharmaceutical composition to said patient by injection. In such embodiments, the peptide or pharmaceutically acceptable salt thereof may be administered at a therapeutically effective dose.

In some aspects, a method for formulating a pharmaceutical composition of the embodiments herein comprising a polymer which forms a gel comprises mixing the peptide or pharmaceutically acceptable salt thereof and the excipient and slowly adding the polymer.

In certain aspects, a method for treating a disease comprises administering a pharmaceutical composition of the embodiments herein to a patient in need thereof. The disease may be cancer, type 2 diabetes, acromegaly, metabolic disorders, endocrine disorders, exocrine disorder or hormone-related tumors. The pharmaceutical compositions may be administered by injection, such as subcutaneous or intravenous injection. In addition, the peptide or pharmaceutically acceptable salt thereof may be administered at a therapeutically effective dose.

A notable peptide is veldoreotide and a pharmaceutically acceptable salt thereof is veldoreotide acetate. Although the invention is described in specific embodiments and examples with regard to veldoreotide and/or veldoreotide acetate, compositions, processes and methods described in this disclosure may also be applied to other peptide or peptide salts, including other somatostatin analogs.

Veldoreotide acetate has improved selectivity of binding and a unique binding profile to the SST receptor subtype SST-R2, SST-R4 and SST-R5 and offers a drug candidate with a clear therapeutic potential, for the treatment of Carcinoid tumors, Acromegaly, and diabetic-associated complications, a unique somatostatin receptor subtypes 2-, 4- and 5-selective analogue, effectively reduces GH secretion in human GH-secreting pituitary adenomas even in Octreotide non-responsive tumours. Veldoreotide acetate has significant advantages over any other somatostatin analog currently available, including Octreotide, in that it is equipotent to available somatostatin analogs in growth hormone inhibition without non-selective effects on insulin or glucagon. Therefore, veldoreotide acetate can improve the availability of pharmacotherapies for endocrine anomalies associated with oversecretion of growth hormone and IGF-1 with better selectivity and better glycemic control of these patients.

According to the present invention, conformationally-constrained, backbone-cyclic synthetic peptide analogs may be combined with excipients to form a pharmaceutical composition for administration to a patient. For example, although veldoreotide acetate is a water soluble molecule, certain excipients unexpectedly improve the solubility of veldoreotide acetate in isotonic conditions.

The pharmaceutical composition comprising peptides or pharmaceutically acceptable salts thereof and excipients may be combined with pharmaceutically acceptable carriers or diluents to formulate the composition for administration to patients.

Figure 2:
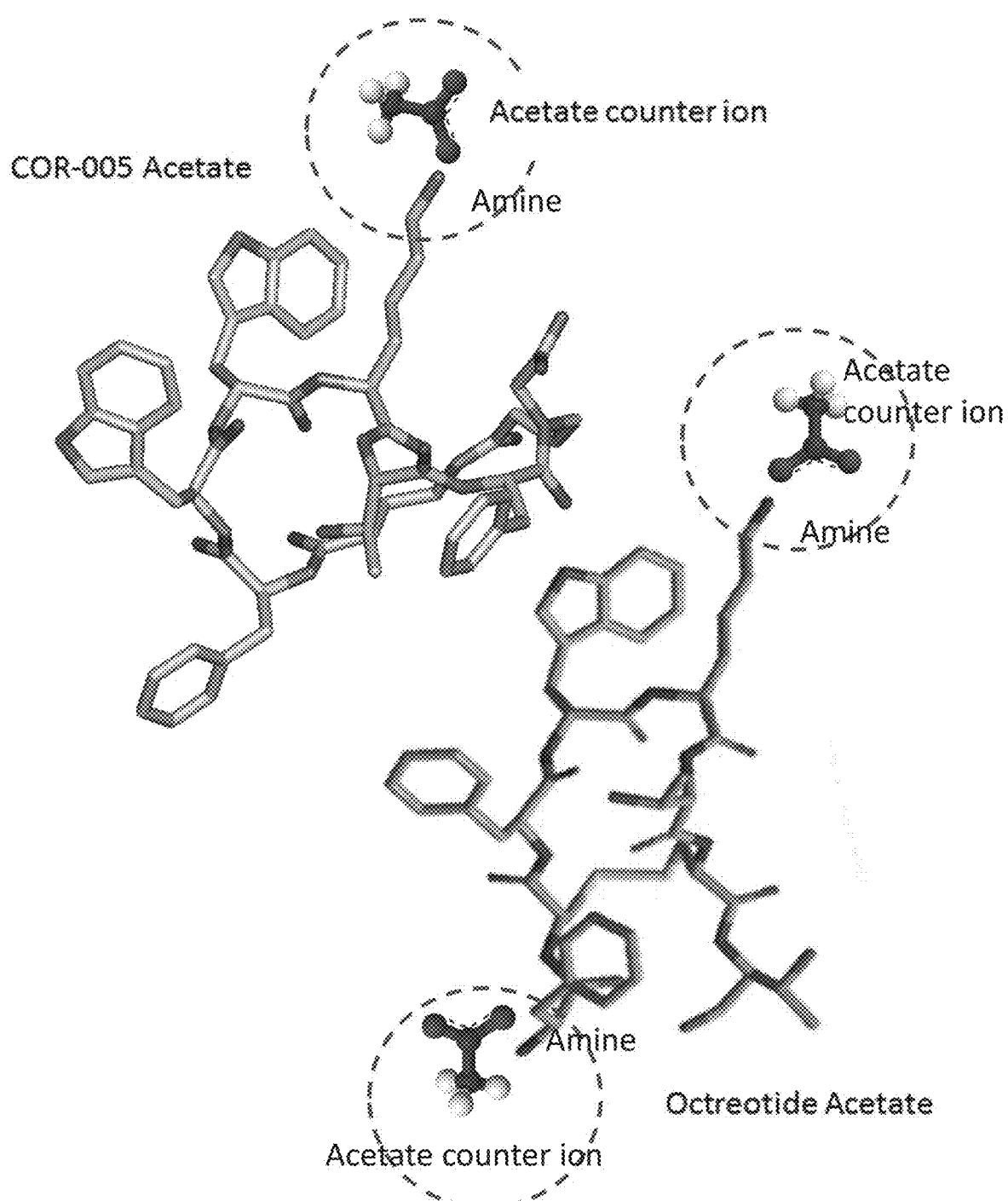
FIG. 2 depicts the three-dimensional structure of both veldoreotide acetate and Octreotide acetate.

The cyclic peptide veldoreotide is composed of a specific combination of amino acids residues that contribute to its unique physicochemical properties in addition to its mechanism of biological action. The combination of the hydrophobic amino acids in positions; $Phe^6$, $Trp^7$, $D-Trp^8$, $Phe^{11}$ opposed to the two hydrophilic head groups of the charged amine of $Lys^9$ and the polar hydroxyl head groups of $Thr^{10}$, creates two distinctive hydrophilic versus hydrophobic domains. As of result of its distinctive hydrophobic and hydrophilic domains, the three-dimensional beta turn and the specific salt form of a single acetate counter ion, veldoreotide acetate has an amphiphilic character and therefore is considered a peptide amphiphile and has a surfactant property as well. FIG. 2 shows a comparison of the three-dimensional structures of veldoreotide acetate and Octreotide acetate, showing that veldoreotide acetate has a single free amine on the lysine residue with a single acetate counterion while Octreotide has two acetate counter ions, one on the lysine residue and one on the terminal amine.

Given the pharmaceutical utility of somatostatin analogs, in particular veldoreotide acetate, a backbone-cyclic somatostatin analog with increased amphiphilic properties as an emulsifier and gel creating agent, and water in oil surfactant, such compositions may be used for the treatment of a variety of diseases and disorders including, but not limited to, cancer, type 2 diabetes, acromegaly, metabolic disorders, endocrine and exocrine disorders, and hormone-related tumors with improved pharmacotherapy characterized by less adverse effects and prolonged drug action.

Another advantage of the pharmaceutical composition is that the composition of veldoreotide acetate with the excipients of the present disclosure improves bioavailability and surprisingly reduces adverse injection site reactions.

Veldoreotide acetate and other backbone cyclic somatostatin analogs have been found to possess considerable metabolic bio-stability against degradation by enzymes.

Veldoreotide acetate exerts significant inhibition with prolonged duration of action on the Growth Hormone-IGF-1 axis of a similar magnitude as the drug Octreotide, but it lacks the disadvantages of Octreotide such as inhibition of Insulin secretion. Veldoreotide acetate also has a considerably lower effect on the release of glucagon than Octreotide, thus having the advantage of not causing hyperglycemia which makes it a very attractive compound for the improvement of glycemic control of acromegalic patients and for the treatment of Diabetes Type 2.

Veldoreotide acetate shows a significant growth inhibition of CHO-cells expression cloned human SST-R5, indicating a potential role in the treatment of SST-R5 expressing tumors (e.g. carcinoids, pituitary tumors). Veldoreotide acetate inhibits Chromogranin A release from the human Carcinoid cell line, indicating an anti-tumor effect.

The unique pharmacokinetic profile of veldoreotide acetate as evaluated in animals is consistent with its metabolic stability as evaluated in-vitro against various enzymes and tissue homogenates. Following subcutaneous administration to rats, veldoreotide acetate had a circulatory half-life of about 3 hours, significantly exceeding the long acting drug Octreotide, which has a circulation half-life of only 40 minutes. This prolonged half-life is due to its unique "flip-flop" kinetics, a result of its slow release from the injection site.

Veldoreotide acetate is selective to somatostatin receptors and binds significantly less to other human cloned G-protein coupled receptors than Octreotide. This characteristic is advantageous because binding to non-somatostatin receptors could cause potential adverse effects in humans.

Veldoreotide acetate has also been found to be non-mitogenic for human lymphocytes in human peripheral blood lymphocytes proliferation assays.

Veldoreotide acetate has been found to have relativity high solubility in water, 5% dextrose, acetone and various alcohols, including ethanol, glycerol and propylene glycol. Veldoreotide acetate has also been found to have relativity high solubility in acidic aqueous solutions such as lactic acid, acetic acid and trifluoroacetic acid. Unexpectedly, the solubility of veldoreotide acetate in hydrochloric acid was found to be concentration-dependent (increased chloride concentration resulted in decreased solubility due to peptide precipitation/salting out). This incompatibility with chloride led to the discovery of its relatively low solubility in physiological conditions (i.e., 0.9% sodium chloride pH 4.5 and phosphate buffered saline pH 7.2) which is not pH-dependent.

The limited solubility of veldoreotide acetate in physiological conditions is a very specific property of the peptide and was previously unknown. Given its relatively high solubility in water, veldoreotide acetate is considered a water-soluble drug. It was surprising and unexpected to find that veldoreotide acetate, a water-soluble drug was found to have low solubility under physiological conditions.

The three-dimensional structure of veldoreotide acetate contains a specific type II β-turn, a conformation that is typical in most of the somatostatin analogs. As a result of this conformation, the three-dimensional flexibility of the peptide is constrained and results in the superposition of the hydrophobic (aromatic) residues exposed on the outside of the peptide ring facing the aqueous environment.

Other cyclic somatostatin analogs, i.e. Octreotide, Lanreotide, Valpreotide and Pasireotide, contain two free amine groups (positively charged head groups); one is the amine of the lysine residue and the other amine at the amino terminus of these peptides. Veldoreotide acetate has only one free amine as a polar head group. Its amino terminus is an amide.

In addition, unlike most somatostatin analogs which have 1-2 phenylalanine and 1 tryptophan amino acids, veldoreotide acetate has 2 phenylalanine and 2 tryptophan amino acids in its sequence.

Veldoreotide is a cyclic molecule. The main role of cyclization is to reduce or constrain the conformational space or three-dimensional (3D) shape of the molecule. Therefore, as such, it is a conformationally constrained molecule. However, though the peptide is constrained by its cyclic structure, its 3D structure or conformation in various aqueous media might be dependent on inter- and intra-molecular interactions of H—H bonding. H—H bonding is the dominant factor of peptide and polypeptide 3D structure.

Veldoreotide acetate has a series of H-donors and acceptors: 12 hydrogen donors and 10 hydrogen acceptors. Other cyclic somatostatin analogs have similar ratios of hydrogen donors to hydrogen acceptors. For example, Octreotide acetate has 13 hydrogen donors and 10 hydrogen acceptors.

Because it has a doubled number of hydrophobic amino acids—2 Trp and 2 Phe and only a single cation/amine, veldoreotide has a 5:2 ratio of hydrophobic to hydrophilic groups. Notably there are more hydrophobic groups than hydrophilic groups in veldoreotide acetate. Octreotide acetate has only 1 Trp and 2 Phe but more importantly, it has two cations/amines and an additional terminal OH and a 3:5 ratio of hydrophobic to hydrophilic groups. This makes octreotide acetate more water soluble and with less surface activity than veldoreotide acetate.

The veldoreotide peptide has a unique composition of hydrophobic amino acids that dominate the hydrophilic portion of the peptide. This composition results in a relatively high degree of amphiphilicity. This amphiphilic property affects the peptide partitioning in aqueous media. It tends to concentrate at the surface of the medium in order to expose the hydrophobic residues to the air to provide thermodynamic stability. When it is concentrated at the surface of the water it reduces the solution surface tension.

Surface tension is the property of a fluid's molecules to adhere to each other at the fluid//air interface more strongly than to the molecules of air, and causes the fluid to behave as if its surface were covered with a stretched elastic membrane. Often, solutes will reduce the surface tension compared to that of the pure solvent. Water and various isotonic solutions have surface tension in the range of about 65-72 dynes/cm at 25° C. A peptide with surface activity will decrease the surface tension: the higher the surface activity of a solute, the lower the surface tension will be, and the more freely molecules or objects can pass through the interface. Veldoreotide acetate reduces the surface tension of doubly distilled water (pH=5.0) to about 45 dynes/cm (see Table 3).

When a peptide is dissolved in aqueous solution, hydrophobic amino acids usually form protected hydrophobic areas while hydrophilic amino acids interact with the molecules of solvation and allow peptides to form hydrogen bonds with the surrounding water molecules. If enough of the peptide surface is hydrophilic, the peptide can be dissolved in water. When the salt concentration is increased, for example in physiological media such as 0.9% NaCl or PBS, some of the water molecules are attracted by the salt ions, which decreases the number of water molecules available to interact with the charged part of the peptide by hydrogen bonding. As a result of the increased demand for solvent molecules, the peptide-peptide interactions are stronger than the solvent-solute interactions; resulting in desolvation of the peptide. The peptide molecules coagulate by forming hydrophobic interactions with each other. This process is known as salting-out.

Based on its amphiphilic properties, veldoreotide acetate was evaluated by means of emulsion formulation. However, it was found that veldoreotide acetate does not act as an oil-in-water o/w emulsifier. Surprisingly, it was found that veldoreotide acetate is a water-in-oil (w/o) emulsifier. Emulsification obtained with veldoreotide acetate with water-in-oil resulted in a stable w/o emulsion. Thus, veldoreotide acetate may be considered a w/o ionic surfactant or hydrotrope with a hydrophilic lipophilic balance (HLB) of 6.

Due to its high hydrophobic group to polar head group ratio (4:1), veldoreotide acetate is more amphiphilic and has enhanced surfactant behavior as demonstrated by the data in Table 3.

Veldoreotide Formulations with Various Excipients

Excipients can improve the solubility, dispersion and bioavailability of injectable peptides such as V veldoreotide acetate. Such excipients may include hydrophobic scavengers, sugars and amino acids such as hydroxypropyl-β-cyclodextrin, L-lysine HCl and dextrose.

Hydroxypropylβ-cyclodextrin

β-cyclodextrins, such as hydroxypropyl-β-cyclodextrin (HP-β-CD or HPBCD), are an exemplary class of excipients for use βn the present invention. HPBCD is a cyclic oligosaccharides composed of 7 dextrose units joined through 1-4 bonds that possess relatively lipophilic interiors and relatively hydrophilic exteriors and tend to form inclusion complexes (Chang, U.S. Pat. No. 7,259,153).

Without being bound by any particular hypothesis, HPBCD may form inclusion complexes with the hydrophobic portions of veldoreotide, thereby lowering its effective hydrophobicity. Ratios of HPBCD:PEP of 1:2 or above (e.g. 10:1) improve the solubility of the peptide in physiological conditions. However, the ratio used to achieve the desired pharmacokinetics profile and bioavailability (1 HPBCD:4 PEP) does not improve the solubility of high veldoreotide concentrations in physiological media (saline or phosphate buffered saline), but is shown to modulate the physical properties of the peptide as evidenced by surface tension. The HPBCD complex with veldoreotide acetate provided a surface tension of over 50 dynes/cm compared to 45 dynes/cm for the uncomplexed veldoreotide acetate (see Table 3). This indicates that the HPBCD:veldoreotide acetate complex is acting less at the surface and more in the bulk solution. Complexation with cyclodextrins to improve solubility occurs at a cyclodextrin to peptide ratio of 1:1 to 10:1, exactly opposite of that observed. The improved solvation of veldoreotide acetate with HPBCD provides less change in surface tension compared to that without HPBCD.

The present invention combines cyclic somatostatin analogs with HP-β-CD to increase solubility in isotonic solutions as well as to increase absorption and bioavailability when such peptides are delivered by injection. Additionally, reduced adverse side effects at the injection site are surprisingly found.

L-lysine HCl

It has been observed that the solubility of veldoreotide acetate is reduced in solutions containing chloride ions. For example, while soluble in 0.1N HCl, veldoreotide acetate is insoluble in 0.9N HCl. Similarly, veldoreotide acetate has limited solubility in isotonic solutions containing chloride, including 0.9% saline and phosphate buffered saline.

It has unexpectedly been discovered that veldoreotide acetate is highly soluble in 20 mM Tris-HCl despite the chloride content of this buffer solution. As chloride concentration increases, however, the solubility of veldoreotide acetate is drastically reduced. For example, the solubility of veldoreotide acetate is significantly reduced if the concentration of Tris-HCl is increased to 137 mM or 117 mM NaCl is added.

As evident from the structure of Tris, the TRIZMA/Tris buffer moiety is composed of a free amine. Therefore, it is hypothesized that the TRIZMA amine competes with the free amine of the lysine residue on veldoreotide acetate for chloride in solution. Even with increased chloride concentration, this effect results in increased solubility of the peptide as it can be dissolved with less chloride around the free amine group. This is confirmed by the decreased solubility of veldoreotide acetate in Tris-HCl as chloride concentration is increased.

In light of the solubility of veldoreotide acetate in Tris-HCl, the solubility of veldoreotide acetate was tested in solutions containing L-lysine and L-lysine HCl.

It was unexpectedly discovered that L-lysine, despite having a free amine to compete with the veldoreotide acetate amine for chloride, did not substantially improve the solubility of veldoreotide acetate. However, more surprisingly, it was discovered that addition of L-lysine HCl substantially improved solubility of veldoreotide acetate in isotonic media and limited precipitation of the peptide.

Dextrose

It has also unexpectedly been discovered that the bioavailability of veldoreotide acetate in isotonic and physiologic solutions is improved by the addition of dextrose as an excipient. Veldoreotide acetate was found to be freely soluble in 5% dextrose (USP), with a solubility of about 400 mg/ml. Surprisingly, 5% dextrose does not improve the solubility of high veldoreotide concentrations in physiological media (saline or phosphate buffered saline). This is counter to the very high solubility of veldoreotide in 5% dextrose in water. The improved LAR pharmacokinetic profile and bioavailability are achieved despite the low dextrose:peptide ratio used (1:8). Such a low ratio is not expected to improve peptide solubility in physiological media, but is shown here to modulate the physical properties of the peptide, as evidenced by surface tension behavior.

Without being bound by any particular hypothesis, dextrose improves the solvation of water around the peptide polar groups. The improved solvation of veldoreotide acetate with dextrose provides less change in surface tension compared to that without the dextrose. The dextrose complex with veldoreotide acetate provided a surface tension of over 50 dynes/cm compared to 45 dynes/cm for the uncomplexed veldoreotide acetate (see Table 3). This indicates that the dextrose:veldoreotide acetate complex is acting less at the surface and more in the bulk solution. This interaction increases the hydrophilicity of veldoreotide and therefore more peptide will be concentrated in the bulk solution rather than at the surface. This improves the bioavailability of veldoreotide.

The present invention combines cyclic somatostatin analogs with dextrose to increase solubility in isotonic solutions as well as to increase absorption and bioavailability when such peptides are delivered by injection. Additionally, reduced adverse side effects at the injection site are surprisingly found.

Nicotinamide is another excipient useful in the compositions (see U.S. Pat. No. 6,331,520.

Sustained Release (SR) Formulations

Microsphere Formulations

Given the pharmacokinetics of cyclic somatostatin analogs, it is often desirable to provide formulations for sustained-release in vivo. A number of methods may be used to accomplish sustained-release including the use of various polymer-based formulations such as the use of PLGA microspheres and hydrogels. Emulsions and liposome formulations may also be useful. While sustained-release formulations, including emulsions, gels, microspheres and liposomes may decrease injection site reactions, improve bioavailability and provide a sustained release profile, based on the findings with excipients for immediate release formulations, the use of such excipients in sustained release formulations was investigated and, surprisingly, the use of such excipients was found to improve the pharmacokinetics of cyclic somatostain analogs in vivo and to reduce injection site reactions.

Cyclic somatostatin analogs may be prepared in PLGA microspheres using conventional techniques well known to those of skill in the art such as that disclosed in Example 7. Cyclic somatostatin analogs may also be formulated into emulsions and gels based on their specific properties.

Without being bound to any particular hypothesis, the difference between the microspheres may be due to how the excipients interact with the 3D structure of veldoreotide, which may be related to its surface activity. As shown in Table 3, the surface tension of the Dextrose-veldoreotide acetate solution is similar to that of the HPBCD-veldoreotide acetate solution, with 54 and 51 Dyne/cm, respectively. Yet, the microscopic structure of microspheres prepared with HPBCD and dextrose are different.

HPBCD has much higher molecular weight (MW) than dextrose, roughly in the same range of the peptide MW. HPBCD has a hydrophobic core which can interact with hydrophobic moieties such as the hydrophobic residues of the peptide, creating one or more inclusion complexes with the hydrophobic portions of the peptide. The portions of the peptide entrapped in the inclusion complex(es) may impart less mobility and less availability to access the polymer when the hydrophobic polymer is introduced. The complex with HDPCD results in an effective decrease in hydrophobicity of the peptide. As a result, the surface interaction between the peptide and the polymer solution is less favored, and the complex of HPBCD with the peptide attracts water. This will result in less dilution/dispersion of HPBCD in the polymer solution, which sets up an internal structure of large droplets and as a result, fewer pores but having bigger diameter and less surface area are formed in comparison to microspheres containing dextrose.

In the microspheres containing dextrose we observed a larger number of small diameter pores. As a small molecule, the dextrose is dispersed/diluted much more in the peptide solution in comparison to the HPBCD. This diluted dextrose enables better mobility of the peptide. Better mobility will lead to better distribution of the peptide within the polymer solution. This better distribution/dispersion of the peptide is due to its hydrophobic property. When the hydrophobic polymer is added, the hydrophobic portions of the peptide will tend to be attracted to the hydrophobic polymer. In summary, the dextrose is affecting the peptide 3D structure via H—H bonding, improving its solvation and, due to its small MW, it improves the peptide distribution and dispersion within the hydrophobic polymer solution. The result is a higher density of pores in the microspheres. The changes in the internal structure of the microspheres are reflected in the surface are of the polymeric microspheres as measured by suitable methods, such as BET. When dextrose or HPBCD is added at certain ratios, such as 1:8 (dextrose to veldoreotide) and 1:2 or 1:4 (HPBCD to veldoreotide), to the primary emulsification used to form the microspheres, the resulting microspheres have a surface area from about 7 $m^2/g$ to about 12 $m^2/g$. It should be understood that there may only be trace amounts of dextrose remaining in the final microsphere product such that the effect of dextrose in formation of the microspheres may be largely a function of dextrose's ability to modify the surface activity of veldoreotide. This effect is discussed in more detail in the Examples set forth below. It does appear however that when HPBCD is used in the primary emulsions to form the microspheres, much of the HPBCD is retained in the final microsphere product.

Thus, in certain embodiments, the mass ratio of dextrose to veldoreotide in the primary emulsion to form the microspheres is from about 1:1 to about 1:16 and more preferably from about 1:4 to about 1:8. Thus, in some embodiments the mass ratio may be about 1:1, 1:2, 1:3, 1:4, 1:5, 1:6, 1:7, 1:8, 1:9, 1:10, 1:11, 1:12, 1:13, 1:14, 1:15, or 1:16.

In certain other embodiments, the mass ratio of HPBCD to veldoreotide in the primary emulsion to form the microspheres is from about 1:1 to about 1:8 and more preferably about 1:2 to about 1:4. Thus, in some embodiments the mass ratio may be about 1:1, 1:2, 1:3, 1:4, 1:5, 1:6, 1:7, or 1:8.

In further embodiments, the primary emulsion to form the microspheres may include both dextrose and HPBCD at the various mass ratios with respect to veldoreotide as set forth above.

Liposome Formulations

It has also been found that veldoreotide acetate can be formulated into liposomes which exhibit a sustained release profile for at least 48 hours wherein the plasma concentration of veldoreotide acetate is at a therapeutically effective level.

Liposomes are concentric, bi-layered vesicles in which an aqueous volume is entirely enclosed by a membranous lipid bilayer mainly composed of natural or synthetic phospholipids. Liposomes are formed when thin lipid films or lipid cakes are hydrated and stacks of liquid crystalline bilayers become fluid and swell. During stirring, hydrated lipid sheets detach and self-associate to form vesicles, which prevent the interaction of water with the hydrocarbon core of the bilayer at the edges. Such liposomes include multilamellar vesicles (MLV) which are composed of a single phospholipid, which is phosphatidylcholine, more preferably 1,2-dimyristoyl-sn-glycero-3-phosphocholine (DMPC).

Emulsions and Hydrogel Formulations

It has been found, as previously noted, that veldoreotide acetate acts as a surfactant and can emulsify water in oil. In addition, given its amphiphilic properties, veldoreotide acetate may also be formulated into a hydrogel. Both vehicles can provide sustained release formulations.

Surprisingly, it has been found that injection of veldoreotide acetate in a water in oil emulsion formulation reduces and delays the onset of injection set reactions and may be injected using as small as a 27G needle.

In addition, it has been found that veldoreotide acetate can form a stable hydrogel that delays induction of injection site reactions and is likewise injectable using as small as a 27G needle.

Thus, emulsion and hydrogel formulations of veldoreotide acetate have been found to be easier to inject and produce less injection site reactions while providing a sustained release formulation for veldoreotide acetate.

EXAMPLES

The present invention is demonstrated in the following examples, it being understood that these are for illustrative purposes only, and the invention is not intended to be limited thereto.

Materials

COR005 acetate (Lonza, DADR-APJ-001-5AN1R)
Hydroxy Propyl β Cyclodextrin—HPB (Merck KGaA, Darmstadt, Germany (Pharma grade) Cyclodextrin HPB Ph. Eur., NF 1.4220.0050)
Dextrose 5%—USP—DEX (Teva Medical Dextrose 5% AWB0064 pH 4.0 252 mOsmol/L pH 4.0 252 mOsmol/L)
Sterile Water For Injection—WFI (Norbrook laboratories Northern Ireland. B.W. 4364-90)
Mannitol—M200 (Merck KGaA, Darmstadt, Germany (Pharma grade) Parteck M200 Emprove exp Ph Eur, BP, JP, USP, E 421)
Lactic Acid Solution (90%)—(Sigma Aldrich USP spec. L6661 Batch #MKBR6268V)
Normal Saline 0.9% NaCl, pH 5.0 (Teva Medical AWB1324 lot XP5E035 pH 5.0, 308 m Osmol/L)
PBS 10 mM pH 7.4 without calcium and magnesium (Dulbecco's Phosphate Buffered Saline Biological Industries REF02023-1A).

Abbreviations

NS—Normal saline (0.9% NaCl), IR—Immediate release, F—Absolute bioavailability calculated against the AUC of the IV of the IR vehicle (rats or minipigs), MS—Microspheres, SC—subcutaneous, BA—Absolute bioavailability, Cmax—Maximal plasma concentration, MAN—Mannitol, HPB—Hydroxy Propyl β Cyclodextrin DEX—Dextrose, PEP—Peptide—COR005 Acetate, Lys-HCl—Lysine hydrochloride., Est.—Estimated by UV-Vis., NT—Not tested, NE—Not applicable due to variability Example 1

The solubility of veldoreotide acetate in aqueous media was screened by the following method. A fixed amount of 10 milligrams of the peptide was weighed and dissolved at ambient temperature by increased (incremental) volumes of the tested medium until a complete solubility was observed, i.e, clear/transparent solution and absence of any precipitates (the solubility endpoint values were defined according to USP guidance). Following the results of the screening studies, several media were selected for verification studies based on quantitative assessment of the peptide concentration by HPLC (maximal solubility). The results of the screening study are depicted in Table 1 while the results of the verification studies are included in Table 2. As can be appreciated from the data, veldoreotide acetate demonstrates high solubility in water and other aqueous media but suffers from limited solubility in isotonic media.

TABLE 1

Solubility Screening of Veldoreotide Acetate

| Medium (ml)/ veldoreotide acetate-10 mg | 0.01 ml Very soluble (1 g/ml) | 0.1 ml Freely soluble (0.1 g/ml) | 0.5 ml Soluble (0.02 g/ml; 20 mg/ml) | 1 ml Sparingly soluble (0.01 g/ml; 10 mg/ml) | 10 ml Slightly soluble (0.001 g/ml; 1 mg/ml) | Results USP Definition |
|---|---|---|---|---|---|---|
| Aqueous media (water based) | | | | | | |
| DDW (Double distilled water) | − | + | ++ | +++ | +++ | Freely soluble |
| WFI-USP (water for injection) | − | +/− | ++ | +++ | +++ | Soluble |
| Dextrose 5% (USP) | − | + | ++ | +++ | +++ | Freely soluble |
| Lactic acid 37 mM, Mannitol 250 mM (pH 4.3) | −/+ | ++ | ++ | +++ | +++ | Freely soluble |
| 0.1% TFA | −/+ | +++ | +++ | +++ | +++ | Freely soluble |
| Acetic acid 1% (glacial) | −/+ | +++ | +++ | +++ | +++ | Freely soluble |
| 0.1N HCL | − | + | ++ | +++ | +++ | Soluble |
| 0.9N HCL | − | − | − | − | − | Insoluble |
| Acetate saline 100 mM, Mannitol 250 mM (pH 4.3) | − | − | − | − | ++ | Slightly soluble (2-3 mg/ml) |
| Saline (USP) (0.9% NaCl) pH 4.5 | − | − | − | − | −/+ | Very slightly soluble |
| PBS pH 7.2 | − | − | − | − | −/+ | Very slightly soluble |
| Alcohols and lipid based media | | | | | | |
| Acetone (USP) | −/+ | ++ | +++ | +++ | +++ | Freely soluble |
| Ethanol (USP) | −/+ | ++ | +++ | +++ | +++ | Freely soluble |
| Propylene glycol | −/+ | ++ | +++ | +++ | ++++ | Freely soluble |
| Glycerol | − | −/+ | ++ | +++ | +++ | Soluble |
| Caprylic acid | − | −/+ | ++ | +++ | +++ | Soluble |
| Oleic acid | − | − | − | − | −/+ | Very slightly soluble |
| 10% EtOH (95%) in olive oil (or cottonseed oil) | − | − | − | +++ | +++ | Sparingly soluble |
| 2% Propylene glycol in olive oil (or cottonseed oil) | − | − | − | +++ | +++ | Sparingly soluble |
| Refined vegetable oils; Olive, Cotton, Coconut, Canola | − | − | − | − | − | Insoluble |

TABLE 2

Quantitative Assessment of Veldoreotide Acetate Solubility

| Medium | Solubility (g/liter) - HPLC |
|---|---|
| Water | 234.49 |
| 20 mM Phosphate*, pH 7.2 | 211.97 |
| 20 mM HEPES, pH 7.2 | 211.76 |
| PBS, pH 7.4 | 3.25 |
| 0.9% NaCl, pH 4.5 | 2.31 |

*10 mM $Na_2HPO_4$ + 10 mM $NaH_2PO_4$

Table 3 summarizes the solubility values of COR005 acetate in various aqueous media, the effects of additives such as DEX and HPB on the peptide solubility in saline and physiological conditions, as well as the PK profile of IR and MS formulations prepared with these additives in comparison to COR005 without additives as control.

Solubility of COR005 Acetate in Aqueous Media

The solubility of COR005 acetate in water and in isotonic 5% Dextrose (see below) is relatively high (at least 300 mg/ml). While, in comparison to its high solubility in water, the solubility of COR005 acetate is significantly lower in physiological (aqueous) conditions (in the range of 1-2 mg/ml) as observed in isotonic PBS pH 7.4 and in saline. Note that both media (PBS or Saline) contained physiological concentrations of chloride which indicates the incompatibility and salting out of the peptide in the presence of the chloride ion.

The Effects of Additives

Dextrose: The relatively high solubility of COR005 acetate in 5% dextrose (in water) of greater than 500 mg/ml indicates the improved solubility of the peptide in water with dextrose. The addition of dextrose to isotonic saline results in an increase in the peptide solubility from 2 mg/ml to about 6 to 7 mg/ml in diluted 5% dextrose in normal saline, which has a final concentration of 2.5% dextrose and 0.45% saline (NaCl). Note that this 1:1 diluted dextrose in saline was used as a vehicle in the IR study of COR005 acetate in rats and minipigs (the DEX:PEP ratio was 5:1).

TABLE 3

| Solution of COR005 Acetate | Additives | Solubility of COR005 Acetate (mg/ml) at 25° C. | Rats Dose mg/Kg Cmax (ng/ml) & BA (F %) | PK Minipigs Dose mg/Kg Cmax (ng/ml) & BA (F %) | |
|---|---|---|---|---|---|
| Water | None | 350 | | NT | |
| 5% Dextrose Isotonic | None | 530 | | | |
| NS—0.9% NaCl | None | 2 | | | |
| 0.45NS—0.45% NaCl | None | 3 | | | Dosage form (SC) |
| Isotonic 0.45NS(0.45% NaCl) 2.5D Dextrose 2.5% | DEX:PEP 5:1 | ≥6.5 | 3 mg/Kg Cmax = 544 F = 116 | 0.1 mg/Kg Cmax = 53 F = 91 0.4 mg/Kg Cmax = 255 F = 85 | IR |
| Lactic acid buffer pH 4.0 Isotonic | Mannitol MAN:PEP 20:1 | 500 (Est.) | 3 mg/Kg Cmax = 345 F = 83 | 0.1 mg/Kg Cmax = 29 F = 45 0.4 mg/Kg Cmax = 108 F = 69 | |
| Saline Isotonic | HPB:PEP 15:1 | 10 | 3 mg/Kg Cmax = 451 F = 85 | 0.4 mg/Kg Cmax = 238 F = 88 | |
| Lactic acid buffer pH 4.0 Isotonic | MAN:PEP 20:1 HPB:PEP 15:1 | 500 (Est.) | Cmax = 350 F = 70 | NT | |
| Saline Isotonic | Lys-HCl:PEP 4:1 | 1.7 | 1.5 mg/Kg Cmax = 220 F = 82 | | |
| PBS pH 7.4 Isotonic (physiologic) | None | 2.2 | B10; 21.9 mg/Kg Cmax = 211 F0-28 d = NE (>B13) | B10; 2.3 mg/Kg Cmax = 1.4 F0-7 d < 1 | MS |
| | HPB:PEP 10:1 | 10 | | NT | |
| | HPB:PEP 1:1 | 4.5 | | | |
| | HPB:PEP 1:2 | 3 | B13; 19.7 mg/Kg Cmax = 211 F0-28 d = 87 | B13; 2.2 mg/Kg Cmax = 47 F0-7 d = 26 | |
| | HPB:PEP 1:4 | 2.5 | NT | B14; 1.81 mg/Kg Cmax = 63 F0-7 d > 100 | |
| | DEX:PEP 5:1 | 1.6 | | NT | |
| | DEX:PEP 1:8 | 2 | B12; 20 mg/Kg Cmax = 133 F0-28 d = NE (>B13) | PSH3; 2.9 mg/Kg Cmax = 12.6 F0-7 d = 21 | |

The PK data for IR formulations injected subcutaneously in rats and minipigs show that the dextrose vehicle increases the Cmax and absolute bioavailability values of COR005 acetate above the other IR formulations (Rats—Cmax of COR005 in dextrose—544 ng/ml versus Cmax of 345 ng/ml of COR005 in lactic acid buffer as control. Minipigs—Cmax of COR005 0.4 mg/Kg in dextrose—238 ng/ml and BA 88.4 versus Cmax of 108 ng/ml and BA 69% of COR005 0.4 mg/Kg in lactic acid buffer as control, the BA of COR005 0.1 mg/Kg were 91% versus 45% respectively). This PK data provided a possible rationale to add dextrose to the MS formulations for two main reasons: 1) Dextrose may increase the solubility and BA of the peptide following its release from the MS, and 2) Dextrose is known as a porosity agent and it may enhance the permeability of the MS thereby improving the release of the peptide from MS matrix.

Unexpectedly, the solubility results of dextrose in PBS were significantly different from the dextrose effect of the peptide solubility in saline. As shown in Table 3, dextrose does not improve the solubility of the peptide in physiological conditions as observed in the isotonic PBS pH 7.4 with DEX:PEP ratios of 5:1 and 1:8, where the solubility is only 1.6 mg/ml and 2 mg/ml, respectively. A possible reason for the poor (unchanged) peptide solubility with dextrose in PBS is the increased ionic strength of the PBS in comparison to saline; PBS contains 0.02% KCl, 0.02% KH2PO4, 0.115% Na2HPO4 and 0.8% NaCl while saline contains only 0.9% NaCl.

The ratio of DEX:PEP 1:8 was the ratio used for the MS formulations B12 or PSI13. This may indicate that the observed PK profile of COR005 acetate in these DEX formulations, which exhibited Cmax and absolute BA higher the basic MS formulation B10 (no DEX), is not due to improved solubility of the peptide in physiological conditions, as the solubility of COR005 acetate in PBS with added DEX is only 1-2 mg/ml. Therefore, there appears to be an effect of DEX on the peptide in MS formulations which goes beyond the effect of increased solubility in physiological conditions.

The mechanism by which dextrose enhances the release and BA of COR005 from MS is discussed in details in the surface tension versus SEM summary data below.

HPB: As shown in Table 3, the additive HPB enhances the solubility of COR005 acetate in both saline and PBS in a concentration dependent manner. A slight increase in solubility was observed with the HPB:PEP ratio of 1:2 (MS formulation B13, see below) over no HPB (an increase from 2.2 to 2.5 mg/ml). The HPB improves further the solubility when the HPB:PEP ratios increased to 1:1, 10:1 and 15:1 and upward, finally reaching a solubility of 10 mg/ml. Note that the solubility of COR005 with the HPB:PEP ratio of 1:4 (MS formulation B14, see below) was in the same range of the poor solubility of the peptide in PBS alone.

The PK data of HPB as an additive to COR005 acetate in the IR formulations indicates an increase in Cmax and BA in rats, and significant increase in minipigs (in both cases, this was the IR formulation with the second highest Cmax and BA). Rats—Cmax of COR005 in HPB—451 ng/ml versus Cmax of 345 ng/ml of COR005 in lactic acid buffer as control. Minipigs —Cmax of COR005 in HPB—255 ng/ml and BA 85.3% versus Cmax of 108 ng/ml and BA of 69% of COR005 in lactic acid buffer as control).

These PK results provided a similar rationale to use HPB in the MS formulations to achieve the same effect as dextrose. Both dextrose and HPB are porosity agents and their composition in the MS might lead to enhancement of the MS permeability and increase of the peptide release. Moreover, in the case of HPB, we hypothesized that it may slightly improve the solubility of the peptide in physiological conditions (especially in the case of HPB:PEP ratio of 1:2 as depicted in the solubility data) in addition to the anticipated porosity effect.

However, unexpectedly, the PK data in rodents of MS with HPB as an additive shows two distinct effects of HPB on the burst and BA in MS formulations B13 and B14. In the case of B13, which was the only one of the two tested in rats, the MS formulation prepared with HPB:PEP ratio of 1:2 (this ratio results in a slight increase of peptide solubility in physiological conditions), the PK in rats shows a significant increase of burst release and absolute BA during the first 24 hours (BA 0-24 hrs) in comparison to the basic formulation B10; Cmax of COR005-B13 211 ng/ml and BA (0-24 hrs) 11% versus Cmax of COR005-B10 30 ng/ml and BA (0-24 h) 2%.

This trend was also observed and verified in the minipig PK studies. In the case of B14, which has a reduced HPB:PEP ratio of 1:4, the expected results were that a reduced porosity of the microspheres with a lower solubility for peptide in physiological condition (as depicted in the table) would consequently reduce the peptide release and plasma concentrations over time.

Surprisingly, and unexpectedly, the PK data for B14 in minipigs shows the opposite effect: the reduced ratio of HPB:PEP results in a significant increase of peptide release, with the Cmax, BA, and plasma peptide levels significantly higher than the values observed for B13, B12, and the basic MS formulation B10.

Note that B14 (HPB:PEP 1:4) as well as B12 and PSI13 (each with DEX:PEP 1:8) all have relatively low ratios of HPB to PEP. These low ratios did not show an improved solubility of the peptide in physiological conditions. Despite the low solubility, there was a significant increase in the release of peptide from the B14 MS as demonstrated by the high BA and prolonged plasma concentrations over time of COR005 acetate in vivo, as compared with the values for B12 and PSI13. Therefore, there appears to be an effect of HPB on the peptide in MS formulations which goes beyond the effect of increased solubility in physiological conditions.

The mechanism by which HPB enhances the release and BA of COR005 from MS is discussed in details in the surface tension versus SEM summary data below.

Example 2

The effect of veldoreotide acetate on the density, pH and surface tension of water was analyzed as shown in Table 4. It has been found that veldoreotide acetate behaves as a peptide amphiphile and reduces the surface tension of water. However, reduction of surface tension of water did not decrease in a dose-dependent manner, suggesting that veldoreotide acetate behaves as a hydrotrope rather than a surfactant.

Tween 80 was used as a control surfactant for comparison. Densities were measured on 1 mL fixed volume samples. All tests were performed in triplicate at 25° C. The effect of veldoreotide acetate on the pH of double distilled water (DDW) was the same at all veldoreotide acetate concentrations. The pH of DDW of 5.0 was reduced to pH 4.5. The effect of veldoreotide acetate on the density of DDW (starting density of DDW was 1.003 g/ml) was concentration dependent from 1.4 mg/ml to 21.5 mg/ml with density ranging from 0.986 to 0.998 g/ml respectively. However, at veldoreotide acetate concentrations of 45 and 102 mg/ml the density was increased above the starting density of DDW. These results indicated that above 45 mg/ml the peptide solution in DDW became saturated. The effect of veldoreotide acetate on the surface tension of DDW (starting surface tension was 64.9 dyne/cm) was consistent with veldoreotide acetate behaving as a peptide amphiphile (surfactant). The surface tension of DDW was reduced by veldoreotide acetate at maximum from 64.9 to 45 dyne/cm. In order to elucidate the meaning of this effect, Tween 80 was used as a reference surfactant. Other surfactants include Polexamer 188. The reduction of surface tension induced by Tween 80 was in the range of 40% (from 64.9 dyne/cm to about 39 dyne/cm), in comparison to veldoreotide acetate of 30% (from 64.9 dyne/cm to about 45 dyne/cm). Note that, under these experimental conditions; the effect of Tween 80 indicated a concentration-effect relationship. Whereas, the effect of veldoreotide acetate on the reduction of surface tension was at the same range for all concentrations tested.

TABLE 4

Effect of Veldoreotide Acetate on Density and Surface Tension of Water

| Tested items | Density (g/ml) Weighted 1 ml (Mettler AT250) | Surface tension (dyne/cm) capillary method | % change in surface tension compared to baseline |
| --- | --- | --- | --- |
| (temperature 25° C.) | | | |
| Sterile water for injection (WFI) pH 5.0 (Norbrook) | 1.012 | 70.9 | |
| Tap water pH 6.0 | 1.014 | 71.12 | |
| Sterile saline (0.9NaCl) pH 5.0 (Teva Medical) | 1.016 | 65.8 | |
| DDW pH 5.0 (Siemens, Labostar, DI 2 Clear, Water System) | 1.003 | 64.9 | — |
| Veldoreotide Acetate 1.4 mg/ml in DDW pH 4.5 | 0.986 | 45.2 | −30 |
| Veldoreotide Acetate 12 mg/ml in DDW pH 4.5 | 0.994 | 46.9 | −28 |

TABLE 4-continued

Effect of Veldoreotide Acetate on Density and Surface Tension of Water

| Tested items | Density (g/ml) Weighted 1 ml (Mettler AT250) | Surface tension (dyne/cm) capillary method | % change in surface tension compared to baseline |
|---|---|---|---|
| Veldoreotide Acetate 21 mg/ml in DDW pH 4.5 | 0.998 | 47.1 | −27 |
| Veldoreotide Acetate 45 mg/in DDW pH 4.5 | 1.003 | 45.97 | −29 |
| Veldoreotide Acetate 102 mg/ml in DDW pH 4.5 | 1.015 | 49.3 | −24 |
| Tween 80 28 mg/ml in DDW (Sigma Aldrich) | 0.975 | 38.8 | −40 |
| Tween 80 14 mg/ml in DDW (Sigma Aldrich) | 0.988 | 39.35 | −39 |
| Tween 80 7 mg/ml in DDW (Sigma Aldrich) (temperature 5° C.) | 0.9945 | 39.6 | −39 |
| Sterile water for injection (WFI) | 0.977 | 68.5 | — |
| Veldoreotide Acetate 200 mg/ml in WFI | 1.03 | 44 | −36 |
| Veldoreotide Acetate 200 mg/ml + 100 mg/ml HPBCD in WFI | 1.12 | 51 | −26 |
| Veldoreotide Acetate 200 mg/ml + 50 mg/ml HPBCD in WFI | 1.04 | 45 | −34 |
| 5% Dextrose in WFI | 1.01 | 62.7 | — |
| Veldoreotide Acetate 200 mg/ml in 5% Dextrose in WFI | 1.03 | 54 | −14 |

Table 5 shows the comparative surface tension of veldoreotide acetate compared to octreotide (somatostatin analog) and goserelin (LHRH analog) in water for injection (WFI)

TABLE 5

| Medium | Water surface tension (dyne/cm) | Effect of reduced surface tension (%) |
|---|---|---|
| Water for injection (WFI-USP) | 52 | Baseline (WFI) |
| Veldoreotide at 10 mg/ml in WFI | 33 | −37% |
| Octreotide at 10 mg/ml in WFI | 38 | −27% |
| Goserelin at 10 mg/ml in WFI | 33 | −37% |

The Surface Activity of COR005 Acetate in Microsphere Formulations

The data of table 4 show the surface activity of highly concentrated COR005 acetate (200 mg/ml), with or without additives in WFI, which emulates the preparation conditions of the primary emulsion of the microspheres. The results of Test 1 and 2 (Table 4) show the effect of COR005 acetate on the surface tension of water. When COR005 acetate is dissolved in water the surface tension is reduced by about 36%, from 68.5 dyne/cm for the water alone to 44 dyne/cm for the solution of water with CR005 acetate at 200 mg/ml.

Figure 3:
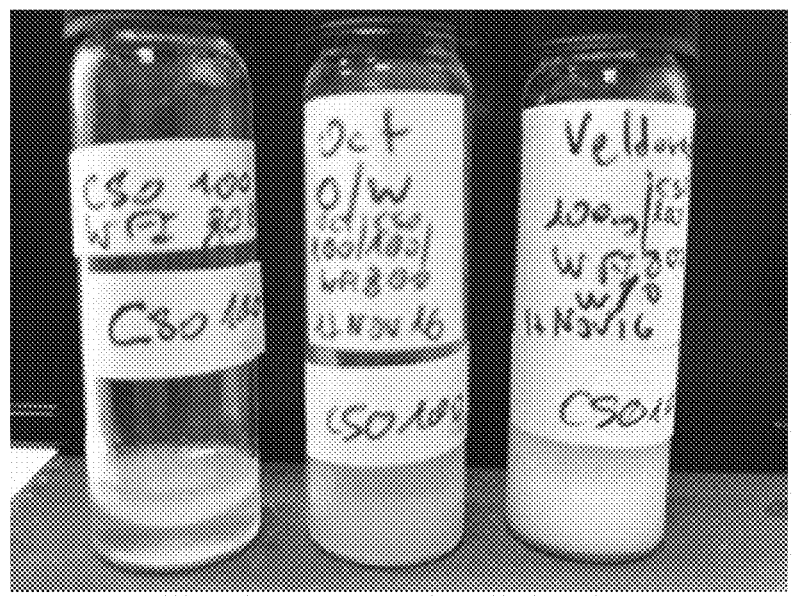
FIG. 3 shows a photograph of the water-in-oil (w/o) emulsion formulations of veldoreotide acetate, octreotide acetate and goserelin in 80:20 cottonseed oil:water for injection (WFI).

The data in Table 5 and FIG. 3 show the comparative emulsification properties of COR005 versus Octreotide and Goserelin provided here as amphiphilic peptide controls. The data show a unique surface activity of COR005 in comparison to the control peptides. COR-005 has higher surface activity than Octreotide and similar surface activity to Goserelin (which is a more hydrophobic peptide than Octreotide).

FIG. 3 shows photographs of emulsification samples of COR005 versus octreotide and goserelin with 16.6 weight % of cottonseed oil (CSO), 74.2 weight % water for injection WFI and 9.2 weight % of peptide. The samples were mixed using 25G syringe and vortexed at room temperature. The emulsification results show the significant affinity of COR005 to the oil/water interface allowing an emulsion to form. Octreotide shows weak emulsification efficiency and goserelin shows the least potential for emulsion formation. These results confirm the unique amphiphilic properties of COR005 as a surfactant.

Without being bound to any particular hypothesis, in aqueous media COR005 appears to have a preferred affinity to the interfacial surface between the water and air due to its hydrophobic amino acids as shown in FIG. 2 (2 Tryptophan, 2 Phenylalanine and only a single cation of the amine type). Consequently less entropy of water will be lost due to the peptide hydrophobicity. The thermodynamics of water are characterized by maximal entropy, the disorder of water molecules and their dynamic hydrogen bonding. When a hydrophobic moiety is mixed with water it interrupts the natural disorder of water molecules and creates "ice cages" that reduce the water entropy and as a result the water molecules repulse the hydrophobic moiety to the surface in order to minimize loss of entropy.

In dispersion systems such as water and oil or aqueous medium with hydrophobic polymer such as PLGA, COR005 will have a high affinity to the lipophilic/hydrophobic interfacial surface due to its amphilic properties. The anticipated effect on the primary emulsion of the MS would be to create smaller droplet sizes in the primary emulsion, an increased stability of the emulsion due to the reduced surface tension of the system by the peptide, and better interaction, orientation, and dispersion of the peptide in the PLGA polymer which is a hydrophobic "surface" forming at the interface.

The observed in vitro release profile of COR005 from the basic B10 MS formulation showed the lowest rate of release. In addition, SEM images (see below) showed a solid and condensed matrix of the MS of the basic formulation B10, which correlates with the peptide release profile. Moreover, the PK data in minipigs demonstrates poor plasma concentrations of COR005 over time for the B10 formulation (Table 3).

The Effect of HPB on COR005 Acetate Surface Activity HPB:PEP 1:2

The addition of HPB at a ratio of 1:2 HPB:PEP results in reduced surface activity of the peptide. The observed surface activity of the peptide in water (44 dyne/cm) without additives is increased back toward water (68 dyne/cm) when HPB is added in a 1:2 ratio (52 dyne/cm). This result indicates that HPB is reducing the potential of the peptide to act as a surfactant by increasing its solubility in water. The result of the reduced peptide surface activity and higher water solubility is that there is less peptide at the interface.

The effect of this on the primary emulsion of the MS will be a relatively higher surface tension of the primary emulsion (in comparison to the basic formulation of the peptide without HPB) and a relatively lower concentration of the peptide at the interfacial surface of the water to the polymer solution. In addition, relatively more water will be retained within the PLGA matrix during the precipitation of the MS due to the high affinity of water to HPB.

The in vitro and in vivo observed burst release (Cmax) of COR005 from B13 (HPB:PEP with 1:2 ratio) was the highest among the basic B10 and the DEX—B12 and PSI13 MS compositions. Moreover, the PK data of B13 in rats shows that most of the peptide was released during the first 24 hours, "dumping" about 20% of total AUC (0-28 days) followed by significantly lower plasma levels during the rest of the 27 days.

The Effect of HPB on COR005 Acetate Surface Activity HPB:PEP 1:4

The results of Test 4 (Table 4) show the effect of reducing the HPB:PEP ratio from 1:2 (Formulation B13) to 1:4 (Formulation B14). The surface tension results show that the reduced concentration of HPB:PEP 1:4 (45 dyne/cm) has the same surface activity as CR005 acetate in water (44 dyne/cm), showing no effect of the HPB on the peptide surfactant properties, in this lower ratio.

In this case the peptide would be expected to have higher concentration at the interface than the HPB:PEP 1:2. The anticipated effect of the reduced HPB:PEP 1:4 ratio would be a reduced in vitro release and BA as well as PK profile in comparison to the IVR and PK profile of Formulation B13. The basic assumption was that the reduced HPB concentration in the MS formulation from HPB:PEP 1:4 would form a microsphere with a denser core in comparison to that from HPB:PEP 1:2 because less water would be attracted to the peptide/HPB complex. Moreover, the permeability of the MS surface would be expected to be reduced (less HPB=less pores). All of these possible effects of the MS with the HPB:PEP 1:4 ratio would result in reduced burst release followed by slower release over time of COR005 from the MS in comparison to the PK profile of Formulation B13 (HPB:PEP 1:2). In other words, instead of having rapid release of the peptide from the MS during the first few days, such as observed with Formulation B13, the B14 formulation should release the same amount of the peptide over a more prolonged period of time.

Unexpectedly, the IVR and PK studies of this HPB:PEP 1:4 ratio showed the opposite effect: the reduced HPB:PEP ratio results in an increased IVR (see the IVR of the PSI series). The same trend was observed in the PK studies as well: the PK profile of B14 results in a higher burst (Cmax), which is greater than Formulation B13. In addition, the plasma levels over time of COR005 released from Formulation B14 were significantly higher than Formulation B13, and also above Formulations B10 and B12.

The Effect of DEX on COR005 Acetate Surface Activity DEX:PEP 1:8

The results of Test 5 (Table 4) show the effect of DEX:PEP when added to the MS formulation at a ratio of DEX:PEP 1:8. The surface tension results shows that the apparent surface tension of the DEX:PEP 1:8 solution (54 dyne/cm) is comparable to the HPB:PEP 1:2 of Test 3 (51 dyne/cm). This effect suggests that more peptide is concentrated in the bulk solution rather than at the interface. Indeed, the surface activity of the peptide under these DEX and HPB to peptide ratios is reduced compared to peptide alone (44 dyne/cm). The additives concentrated in the water may lead to increased water attraction around the peptide during the primary emulsion. This may lead to an increased porosity of the microspheres due to relatively higher water content in the internal matrix such as was expected to happen with the B13 formulation.

However, the comparative PK data of Formulations B12 (DEX:PEP) and B13 (HPB:PEP) do not support these assumptions. While the peptide release and plasma levels of Formulation B13 showed a high burst release and low plasma concentration over time, the burst release from Formulation B12 is reduced and the plasma levels are increased over time significantly above those of Formulation B13. These unexpected results indicate that the surface tension of the primary emulsion and the external porosity of the final MS are not the only factors affecting the observed peptide PK profile.

Thus, we searched for another factor linking the external porosity of the MS and surface tension of the peptide to support (empirically) the unexpected effects of the additives observed in the IVR and PK studies. This factor was identified, following attempts to evaluate the effects of the various conditions on the internal (rather than external) morphology of the various MS formulations. In addition, the SEM images discussed below supported the hypothesis that the surface tension measurements identified a condition of varying peptide interfacial concentration which was affected by changing concentrations of the additives HPB and DEX. Indeed, only when the SEM imaging was repeated by cutting the microspheres in order to expose their internal texture, were the links observed between the surface activity data and the IVR and PK data of COR005 MS formulations (see below).

Table 6 summarizes the effects of additives on the surface activity profile of COR005 acetate under physiological conditions (37° C.) that emulate the release of COR005 at the injection site.

TABLE 6

| Medium | Dextrose (wt %) | HPB:PEP ratio | COR005 (mg/ml) | Solubility (mg/ml) | Surface tension (dyne/cm) | Effect of surface tension (% of baseline) |
|---|---|---|---|---|---|---|
| PBS pH 7.4 | 5 | None | None | ND | 57 | Baseline (PBS/5% DEX) |
|  |  |  | 10 | 3.3 | 49 | −14% (−18% at 48 h) |

TABLE 6-continued

| Medium | Dextrose (wt %) | HPB:PEP ratio | COR005 (mg/ml) | Solubility (mg/ml) | Surface tension (dyne/cm) | Effect of surface tension (% of baseline) |
|---|---|---|---|---|---|---|
| | None | None | None | ND | 48 | Baseline (PBS) |
| | | None | 10 | 3.6 | 34 | −29% |
| | | 10:1 | | 8.9 | 50 | +4% |
| | | 1:2 | | 5 | 45 | −6% |
| | | 1:4 | | 3.9 | 39 | −19% |

The data depicted in Table 6 shows that the ratios of both additives DEX or HPB to the COR005 acetate do not improve the solubility of COR005 acetate in physiological conditions (it was shown in Tables 3 and 4 that DEX doesn't improve the solubility of peptide in PBS and that HPB improves the solubility of the peptide in PBS in a concentration dependent manner). The solubility of the peptide with additives in the concentrations used for MS formulations does not support the observed increased release and BA of the peptide due to solubility. The surface tension of COR005 with HPB at high ratio of HPB:PEP of 10:1 (50 dyne/cm) confirms the assumption and the observed effect of HPB of the peptide surface activity: increased HPB will increase peptide solubility and reduce the peptide surface activity because more peptide will be in the bulk solution rather at the interface. In the case of reduced HPB:PEP, from 1:2 to 1:4, the surface tension of the solution is reduced as well. Less HPB in the system results in greater surface activity of the peptide, with more peptide available at the interface. These results support the observed IVR and PK data of Formulation B13 versus Formulation B14. When the HPB is added to MS, the porosity is increased and the peptide release is affected by the extent of interaction (inclusion complex) between the peptide and the HPB in the microenvironment of the internal space of the MS. In the case of Formulation B13 where the HPB:PEP is relatively high, more pores are produced in MS and more peptide is at the internal surface of the pores rather than within the polymer matrix. More water will be available to the internal matrix (due to more pores in the external shell) and rapid diffusion of water to the internal matrix occurs. At the internal matrix, most of the peptide is available to release from the polymer due to the effect of HPB. This results in relatively rapid release of the peptide as observed in the IVR and PK of Formulation B13, which showed increased burst and rapid release during the first few days followed by lower plasma concentrations over time.

The same trend is supported by the effect of reduced HPB:PEP ratio of 1:4 (Formulation B14). Table 4 shows that the surface activity of the peptide in this condition (of low HPB) is similar to the peptide surface activity without additive, 34 versus 39 dyne/cm respectively. In this case, the porosity of the MS is reduced in comparison to Formulation B13 (with more HPB) and the peptide surface activity is retained, leading to more peptide oriented at the interface of the pore. When water is diffused into the B14 MS the release of the peptide is affected by the release from the internal polymeric matrix and from the internal space of the pores.

These observations and conclusion are supported by the analysis of the residual HPB concentration in the MS formulations of HPB. Indeed, the analytical data (see below) confirms that the same ratio of HPB:PEP were maintained in the final MS of HPB and therefore verifying the conditions and data of Table 6.

As for the results of DEX, the analytical data of the residual DEX in the final MS showed significantly lower DEX:PEP ratio which indicates that most of initial DEX content was washed out from the MS during the preparation process. Therefore, unlike the case of HPB, the effect of the DEX on the COR005 surface activity at the injection site seems to be negligible. The effect for the DEX is addressed in the SEM analysis section below.

Example 3

Veldoreotide acetate immediate release formulations (Groups 1M-6M) were prepared for injection into HSD: SPRAGUE DAWLEY® SD® rats as shown in Table 8 below. The lactic acid vehicle for use in the formulations as shown in Table 7 below was prepared as follows:

TABLE 7

| Formulation | Amount | Dose (net peptide/kg) |
|---|---|---|
| Calculated batch size | ~2970 vials | 0.5 mL per rat |
| Veldoreotide Acetate | 6.83 g net peptide | sub-cutaneous |
| D-mannitol 0.5 mol/kg | 1707.5 g | 2.8 mg/kg |
| (s) - Lactic Acid Solution 0.185 mol/kg | 683 g | |
| WFI | 341.5 g | |
| Sodium Hydrogen Carbonate 0.185 mol/kg | q.s. pH 4.3 +/− 0.1 | |
| WFI (European Pharmcopeia) | 3466.23 g | |
| Final API concentration | 2 mg/mL (1.15 mL per vial) | |

Formulations for injection into rats were prepared as summarized in Table 8.

Subject rats (mean weight of about 370 grams per subject) were injected according to the above dosing schedule in groups of 5 rats per treatment. Baseline tail bleed samples were drawn from the rats at 2 days prior to dosing. For Group 1M, blood samples were drawn at 5 minutes, 10 minutes, 30 minutes, 1 hour, 2 hours, 4 hours, 6 hours, 8 hours and 24 hours post-dosing. For Groups 2M-6M, tail bleed samples were drawn from the rats at 30 minutes, 1 hour, 2 hours, 3 hours, 6 hours, 8 hours, 12 hours and 24 hours post-dosing. Blood samples were approximately 300 uL of whole blood collected in commercial K3 EDTA-coated tubes. Subject rats were also observed for injection site reactions for up to 5-7 days post-dosing.

All subcutaneous injections induced injection site reactions. The rating of injection site reactions is shown in Table 9.

TABLE 8

| Group | Formulation | Amount | Dose (net peptide) |
|---|---|---|---|
| 1M | Veldoreotide acetate in lactic acid vehicle (Table 4) | Total volume - 2.3 mL<br>Total net API - 4.6 mg | 0.28 mL per rat intravenous<br>1.5 mg/kg |
| 2M | Veldoreotide acetate in lactic acid vehicle (Table 4)<br>Additional Veldoreotide acetate (8 mg equivalent to 6.9 mg net peptide)<br>Hydroxypropyl-ß-cyclodextrin<br>Final Hydroxypropyl-ß-cyclodextrin concentration<br>Final API concentration | Total volume - 2.3 mL<br>Total net API - 11.5 mg<br>Total Hydroxypropyl-ß-cylclodextrin - 150 mg<br><br>150 mg<br>65 mg/mL<br><br>5 mg/mL | 0.23 mL per rat s.c.<br>Veldoreotide acetate (net peptide) - 3 mg/kg<br>Hydroxypropyl-ß-cylcodextrin 40 mg/kg |
| 3M | Veldoreotide acetate in lactic acid vehicle (Table 4)<br>Additional Veldoreotide acetate (8 mg equivalent to 6.9 mg net peptide)<br>Final API concentration | Total volume - 2.3 mL<br>Total net API - 11.5 mg<br><br><br>5 mg/mL | 0.23 mL per rat s.c.<br>Veldoreotide acetate (net peptide)<br>3 mg/kg |
| 4M | Veldoreotide acetate (8 mg equivalent to 6.9 mg net peptide)<br>Saline 0.9% NaCl<br>L-Lysine HCl<br>Final L-Lysine HCl<br>Final API concentration | Total volume - 4.4 mL<br><br><br>Total net API - 6.9 mg<br><br>6.8 mg/mL<br>1.6 mg/mL | 0.34 mL per rat s.c.<br>Veldoreotide acetate (net peptide) -<br>1.5 mg/kg<br>L-Lysine HCl - 6.3 mg/kg |
| 5M | Veldoreotide acetate (11.6 mg equivalent to 10 mg net peptide)<br>Saline 0.9% NaCl<br>Hydroxypropyl-ß-cyclodextrin<br>Final Hydroxypropyl-ß-cyclodextrin concentration<br>Final API concentration | Total volume - 2 mL<br><br>Total net API - 10 mg<br>150 mg<br>75 mg/mL<br><br>5 mg/mL | 0.23 mL per rat s.c.<br>Veldoreotide acetate (net peptide) -<br>3 mg/kg<br>Hydroxypropyl-ß-cylcodextrin - 47 mg/kg |
| 6M | Veldoreotide acetate (11.6 mg equivalent to 10 mg net peptide)<br>Saline 0.9% NaCl - 1 mL<br>Dextrose 5% - 1 mL<br>Final Saline concentration<br>Final Dextrose concentration<br>Final API concentration | Total volume - 2 mL<br><br>Total net API - 10 mg<br>150 mg<br><br>0.45%<br>2.5%<br>5 mg/mL | 0.23 mL per rat s.c.<br>Veldoreotide acetate (net peptide) -<br>3 mg/kg<br>Dextrose - 2.5% |

TABLE 9

| Group ID | Dose (mg/kg) | Injection Site Reaction |
|---|---|---|
| 2M | Peptide - 3<br>Hydroxypropyl-ß-cyclodextrin - 40 | Severe |
| 3M | Peptide - 3<br>Peptide - 3 | Severe |
| 4M | L-Lysine HCl - 6<br>Peptide - 3 | Mild/slight |
| 5M | Hydroxypropyl-ß-cyclodextrin - 40<br>Peptide - 3 | Severe |
| 6M | Dextrose - 15 | Mild |

Severe injection site reactions were observed with the lactic acid vehicle-formulated veldoreotide acetate injections. However, rats injected with veldoreotide acetate formulated with L-lysine HCl or Dextrose in saline (Groups 4M and 6M, respectively) exhibited relatively low injection site reactions.

Blood samples were kept on ice following collection until the time of centrifugation. Blood samples were processed within 60 minutes from blood collection. Samples were centrifuged at 3000 G for 15 minutes in a refrigerated centrifuge (5° C.). Plasma was withdrawn from the tubes after centrifugation and placed into new, appropriately labeled tubes and stored at −65° C. to −80° C. until transfer.

Plasma samples were analyzed via LC-MS/MS to determine plasma concentration of veldoreotide acetate for Groups 1M-6M. Veldoreotide acetate standard was serially diluted with methanol:water (1:9) and added to blank rat plasma to generate calibration standards and QC samples. The calibration samples were stored at −70° C. Frozen samples were then thawed to room temperature. Blank plasma and reagent blank (water) were also prepared. For each 100 uL aliquot of sample, calibrator or QC sample, 25 uL (~100 ng/mL) of internal standard (octreotide acetate) in methanol:water (1:9) and 600 uL of acetonitrile:formic acid (99:1) were added and the samples vortex mixed for 30 seconds. Samples were diluted by mixing 20 uL of plasma sample with 180 uL of blank plasma and aliquotted at 100 uL prior to addition of the internal standard and acetonitrile: formic acid solutions.

Samples were then centrifuged for 10 minutes at 14,000 rpm at 8° C. 450 uL of the upper (organic) layer was then transferred to evaporation tubes and evaporated under nitrogen at about 50° C. Samples were then reconstituted in 200 uL of reconstitution solution (water:acetonitrile:formic acid at 70:30:0.2). Samples were centrifuged for 10 minutes at 4000 rpm at 8° C. 160 uL of each sample was withdrawn and placed in an autosampler vial with conic glass insert and analyzed via LC-MS/MS.

Figure 4:
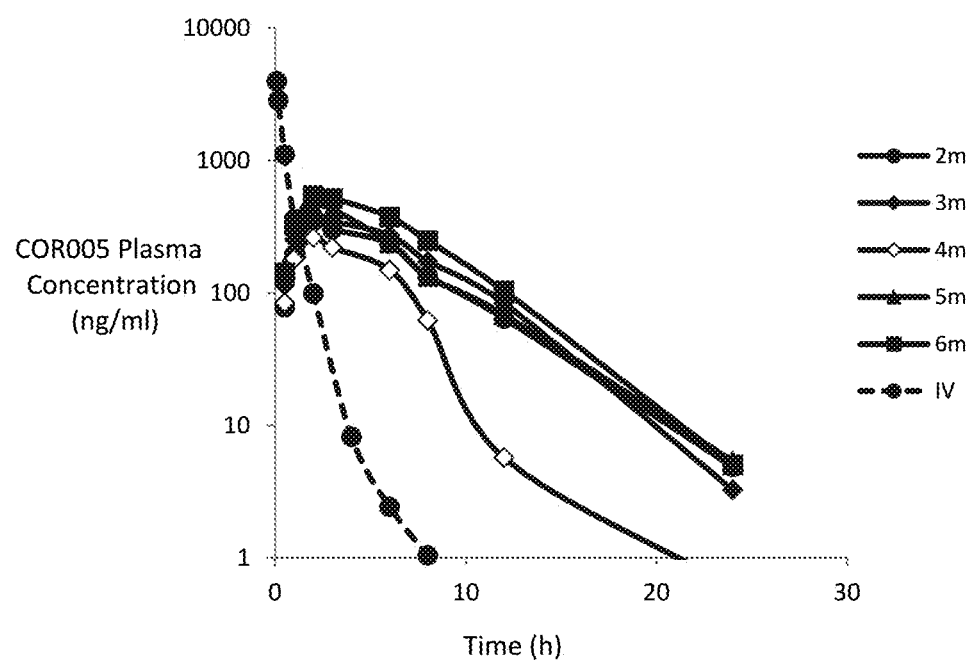
FIG. 4 shows a graph of plasma concentration of veldoreotide acetate in rats injected with various formulations of veldoreotide acetate with or without excipients.

Veldoreotide acetate plasma concentrations were then plotted and analyzed using standard pharmacokinetic techniques. The pharmacokinetic parameters obtained for Groups 1M-6M are shown in Table 10. A graph of plasma concentration (semi-log) versus time for Groups 2M-6M is shown in FIG. 4.

TABLE 10

| PK Parameters | 1M IV COR005 Acetate 1.5 mg/kg | 2M SC COR005 Acetate 3 mg/kg (HPB lactic acid) | 3M SC COR005 Acetate 3 mg/kg (in lactic acid) | 4M SC COR005 Acetate 1.5 mg/kg (with LysHCl) | 5M SC COR005 Acetate 3 mg/kg (HPB in NS) | 6M SC COR005 Acetate 3 mg/kg (2.5 Dex 0.45 NS) |
|---|---|---|---|---|---|---|
| N | 4 | 5 | 5 | 5 | 5 | 5 |
| Dose (mg/kg) | 1.5 | 3 | 3 | 1.5 | 3 | 3 |
| CMax (ng/mL) | 3991 ± 664 | 350 ± 111 | 345 ± 95 | 220 ± 54 | 451 ± 129 | 544 ± 245 |
| CL (mL/h/kg) | 782 | (—) | (—) | (—) | (—) | (—) |
| $T_{1/2}$ (h) | 0.66 | 3.3 | 2.5 | 2.8 | 3.3 | 2.8 |
| AUC (ng-h/mL) | 1918 ± 6 | 2703 ± 347 | 3179 ± 466 | 1574 ± 213 | 3254 ± 609 | 4458 ± 750 |
| F (%) | 100 | 70 | 83 | 82 | 85 | 116 |

The comparative semi-log PK profiles of SC versus IV of COR005 acetate show that COR005 acetate exhibits a flip-flop kinetics. The rate slope of the SC curves shift to right in comparison to the elimination curve of the IV. Hence, the apparent peptide absorption rate from the SC injection site is significantly slower and prolonged above the elimination rate. Thus, the apparent half-life values of all SC formulations are actually the half-life of absorption which dominates the effect of elimination phase of the pharmacokinetic profile.

Figure 5:
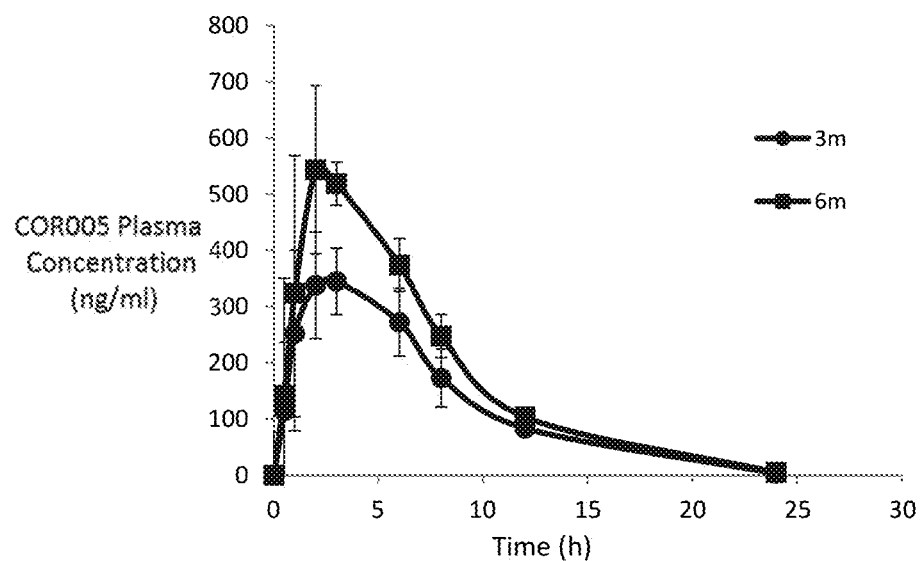
FIG. 5 shows a graph illustrating the effect of the dextrose/saline IR formulation on COR005 PK profile in rats at 0.3 mg/kg DEX:PEP ratio 5:1.
Figure 6:
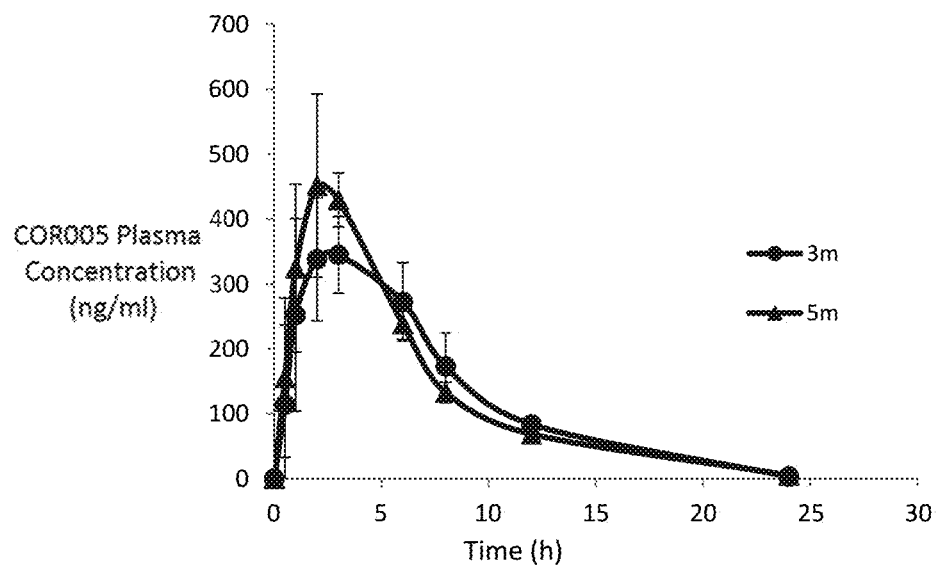
FIG. 6 is a graph illustrating the effect of the dextrose/saline IR formulation on COR005 PK profile in rats HPB/saline (HPB:PEP 15:1).
Figure 7:
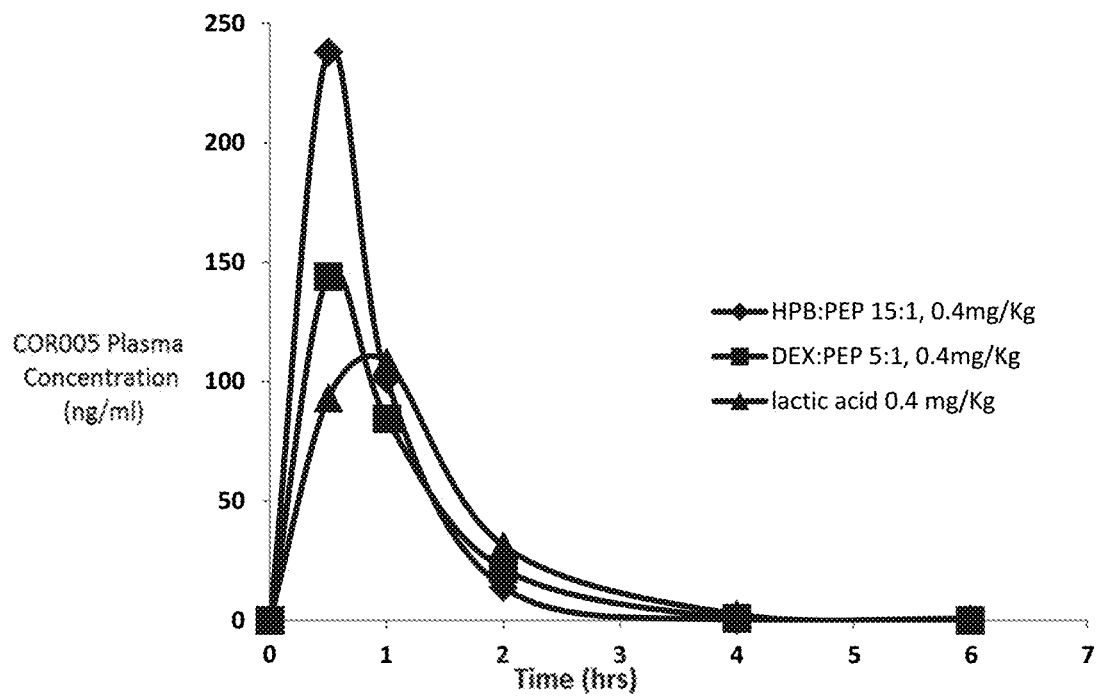
FIG. 7 is a graph comparing the HPB and DEX SC formulations in minipigs at 0.4 mg/kg.
Figure 8:
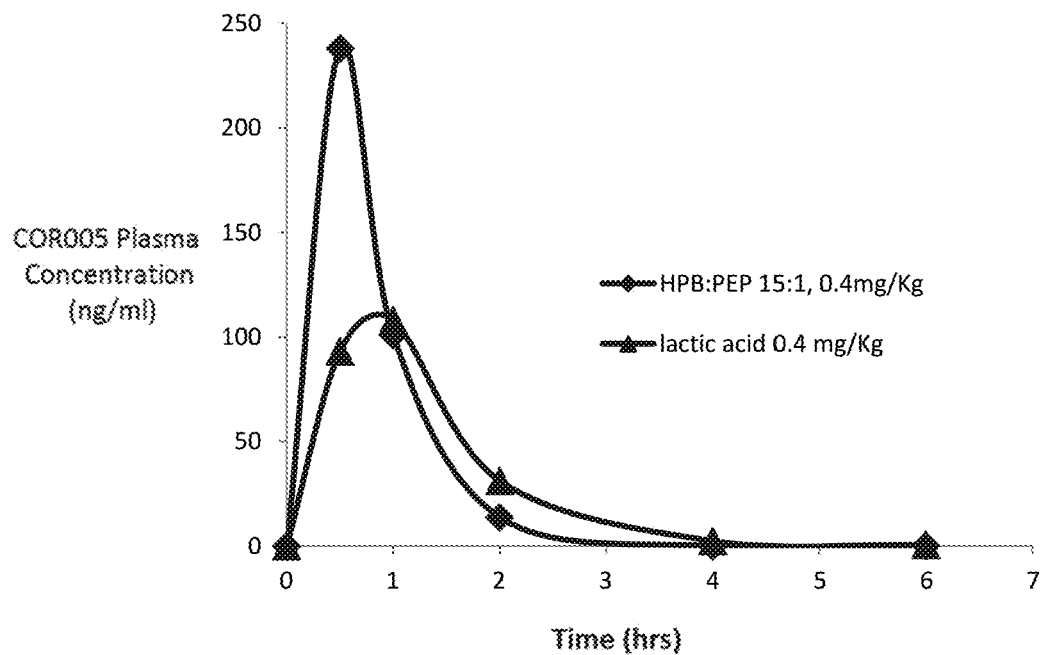
FIG. 8 is a graph comparing the HPB formulation to lactic acid in minipigs at 0.4 mg/kg.
Figure 9:
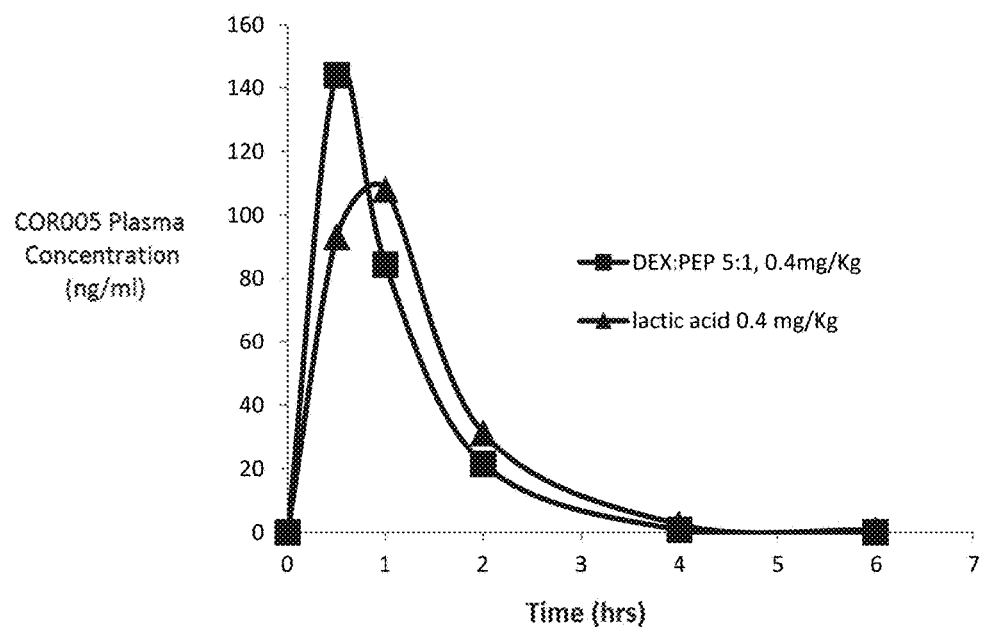
FIG. 9 is a graph showing the effect of DEX on the PK profile of COR005 acetate IR formulation, SC, 0.4 mg/Kg in minipigs.
Figure 10:
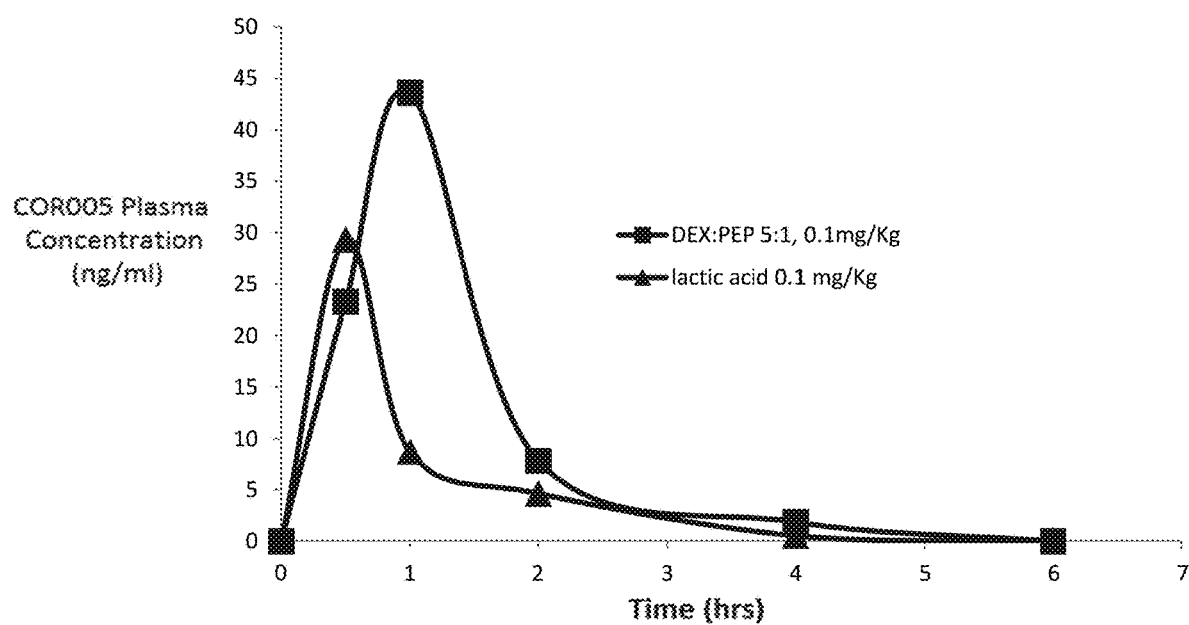
FIG. 10 is a graph showing the effect of DEX on the PK profile of COR005 acetate IR formulation, SC, 0.1 mg/Kg in minipigs.

FIG. 5 is a graph illustrating the effect of the dextrose/saline IR formulation on COR005 PK profile in rats at 0.3 mg/kg DEX:PEP ratio 5:1 (6 m) compared to the COR005 in lactic acid buffer pH of 4 (3 m) used as a control. FIG. 6 is a graph illustrating the effect on COR005 PK profile in rats of the HPB/saline (HPB:PEP 15:1) (5 m) compared to the COR005 in lactic acid buffer pH of 4 (3 m) used as a control. FIG. 7 is a graph comparing the HPB and DEX sc formulations in minipigs at 0.4 mg/kg compared to the COR005 in lactic acid buffer pH of 4 (3 m) used as a control. FIG. 8 is a graph comparing the HPB formulations in minipigs at 0.4 mg/kg compared to the COR005 in lactic acid buffer pH of 4 (3 m) used as a control. FIG. 9 is a graph showing the effect of DEX on the PK profile of COR005 acetate IR formulation, SC, 0.4 mg/Kg in minipigs compared to Lactic acid buffer pH 4 used as a control. FIG. 10 is a graph showing the effect of DEX on the PK profile of COR005 acetate IR formulation, SC, 0.1 mg/Kg in minipigs compared to Lactic acid buffer pH 4 used as a control.

The comparative PK profiles indicate that either Dextrose or HPB enhanced the COR005 plasma Cmax and its absolute bioavailability above the other vehicles.

Table 11 summarizes the Pharmacokinetic parameters of COR005 Acetate IR formulations in minipigs, (Dose 0.4 mg/Kg) showing the effect of HPB and DEX on COR005 Cmax and absolute BA, with Lactic acid buffer pH 4 used as a control. Table 12 summarizes the Pharmacokinetic parameters of COR005 Acetate IR formulations in minipigs, (Dose 0.1 mg/Kg) showing the effect of DEX on COR005 Cmax and absolute BA, with Lactic acid buffer pH 4 used as a control.

TABLE 11

| IR - COR 005 acetate | Dose (mg/Kg) | $T_{max}$ (hrs) | $C_{max}$ ng/ml) | $AUC_{last}$ (hrs * ng/ml) | Absolute BAF (%) |
|---|---|---|---|---|---|
| Lactic acid buffer | 0.4 | 1 | 108 | 161 | 69 |
| DEX:PEP 5:1 saline | 0.4 | 0.5 | 238 | 205 | 88.4 |
| HPB:PEP 15:1 saline | 0.4 | 0.25 | 255 | 198 | 85.3 |

TABLE 12

| IR - COR 005 acetate | Dose (mg/Kg) | $T_{max}$ hrs) | $C_{max}$ (ng/ml) | $AUC_{last}$ (hrs * ng/ml) | Absolute BAF (%) |
|---|---|---|---|---|---|
| Lactic acid buffer | 0.1 | 0.5 | 29.3 | 26 | 45 |
| DEX:PEP 5:1 saline | 0.1 | 1 | 43.6 | 53 | 91.4 |

The HPB increases the half-life of COR005 absorption (M2 and M5) in comparison to the lactic acid vehicle (M3) and dextrose (M6). This indicates a slower release and prolonged absorption of COR005 from the HPB vehicle.

The trough concentration for Groups 2M-6M at 24 hours was also analyzed and is shown in Table 13.

TABLE 13

| Group | Veldoreotide Acetate Plasma Concentration (ng/mL) for Each Subject | | | | |
|---|---|---|---|---|---|
| 2M | 4.44 | 6.99 | 7.87 | 0.00 | 5.10 |
| 3M | 60.3 | 0.00 | 2.01 | 8.31 | 0 |
| 4M | 0 | 3.036 | 0 | 0 | 0 |
| 5M | 7.70 | 6.235 | 7.621 | 3.700 | 1.65 |
| 6M | 15.08 | 2.55 | 1.25 | 2.24 | 4.15 |

As may be noted, the intravenous injection of veldoreotide acetate confirms an expected CL of 13 ml/min/kg based on available literature (See Afargan et al., Novel Long-Acting Somatostain Analog with Endocrine Selectivity: Potent Suppression of Growth Hormone But Not of Insulin, Endocrinology, 142:1 (2001) 477-486). In addition, the addition of excipients improves the pharmacokinetic performance of veldoreotide acetate. For example, addition of dextrose in saline (Group 6M) improves AUC and produces an F-value greater than 100%. As seen in FIGS. 5-11, the addition of excipients results in improved bioavailability of veldoreotide acetate. In addition, as shown in Table 13, the addition of excipients such as hydroxypropyl-β-cyclodextrin (Groups 2M and 5M) and dextrose (Group 6M) results in a measurable trough concentration of veldoreotide acetate after 24 hours. Therefore, the addition of excipients has been demonstrated to not only reduce injection site reactions but also to improve the pharmacokinetics of immediate release veldoreotide in a rat model.

Example 4

Veldoreotide acetate was formulated into PLGA (poly lactic-co-glycolic acid) microspheres according to the formulations in Table 14.

TABLE 14

| Composition | Formulations | | | | |
| --- | --- | --- | --- | --- | --- |
| | B9 | B10 | B11 | B12 | B13 |
| Veldoreotide acetate, mg | 200 | 200 | 200 | 200 | 200 |
| PLGA (7-17 kDa), mg | — | 500 | — | 500 | 500 |
| PLGA (38-54 kDa), mg | 500 | — | 500 | — | — |
| Dextrose 5% (USP), mg | — | — | 25 | 25 | — |
| Hydroxypropyl-ß-cyclodextrin, mg | — | — | — | — | 100 |

The formulations in Table 14 were administered to rats via injection using a 23G needle for formulations B9 and B10 and a 19G needle for formulations B11-B13. An exact volume of 0.5 mL of the formulation was administered to each animal. Tail bleed samples were drawn at various timepoints over 28 days to determine the pharmacokinetics of the veldoreotide acetate formulations and injection site reactions were monitored. Methodologies employed are similar to those disclosed in Example 3.

Pharmacokinetic Analysis of PLGA-MS-COR005 Acetate Formulations in Rat Plasma The analysis of the pharmacokinetics of COR005 was performed using the PK Solutions 2.0 software (Summit Research Services, CO. USA). The software calculates results using noncompartmental (area) and compartmental (exponential terms) methods without presuming any specific compartmental model. Multiple dose and steady-state parameters are automatically projected from single dose results. PK parameter calculations were based on two standard methods of analysis: (1) curve-stripping (or method of residuals) to derive the exponential terms that describe the blood level curve, and (2) area under the curve calculations. PK Solutions 2.0 applies both methods where applicable and compares the results side-by-side.

PK data analysis was performed by PK profiling of each animal of each group. The comparative PK parameters of the various treatments were represented by the mean±STDEV of each group.

Figure 11:
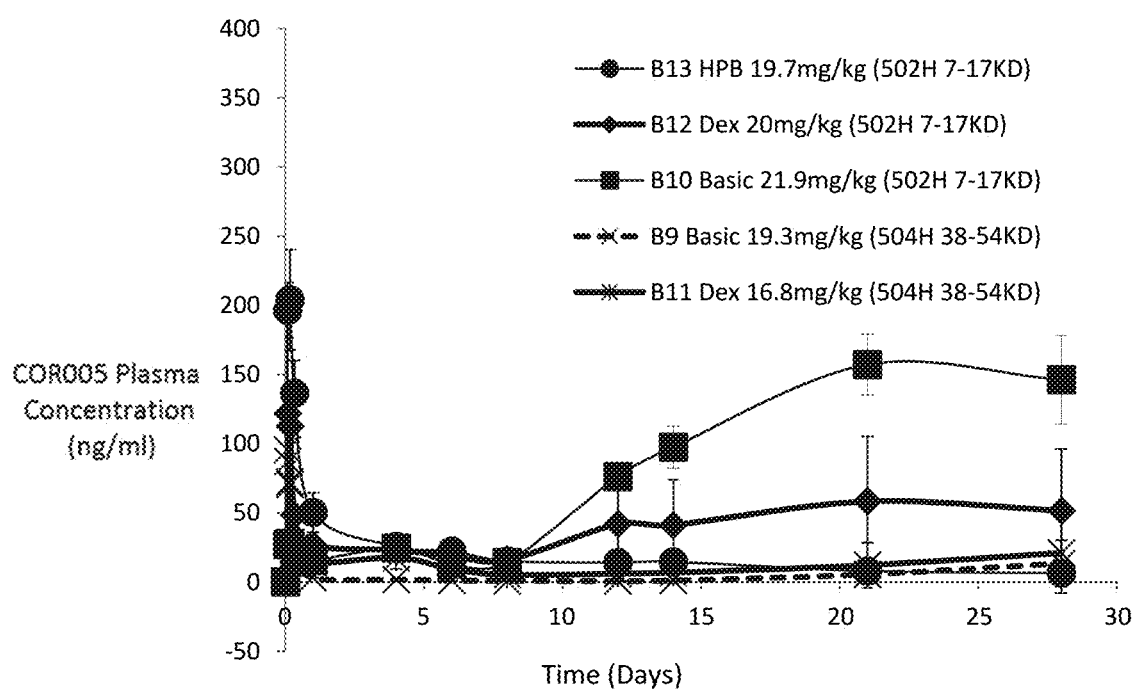
FIG. 11 shows a plot of the COR005 Plasma Concentration of SC treatment groups B9-13.

FIG. 11 shows a Standard Plot of the COR005 Plasma Concentration as Time Curves of the means±STDEV of SC treatment groups B9-13 PLGA-MS formulations of COR005 Acetate (time 0 to 28 days).

Figure 12:
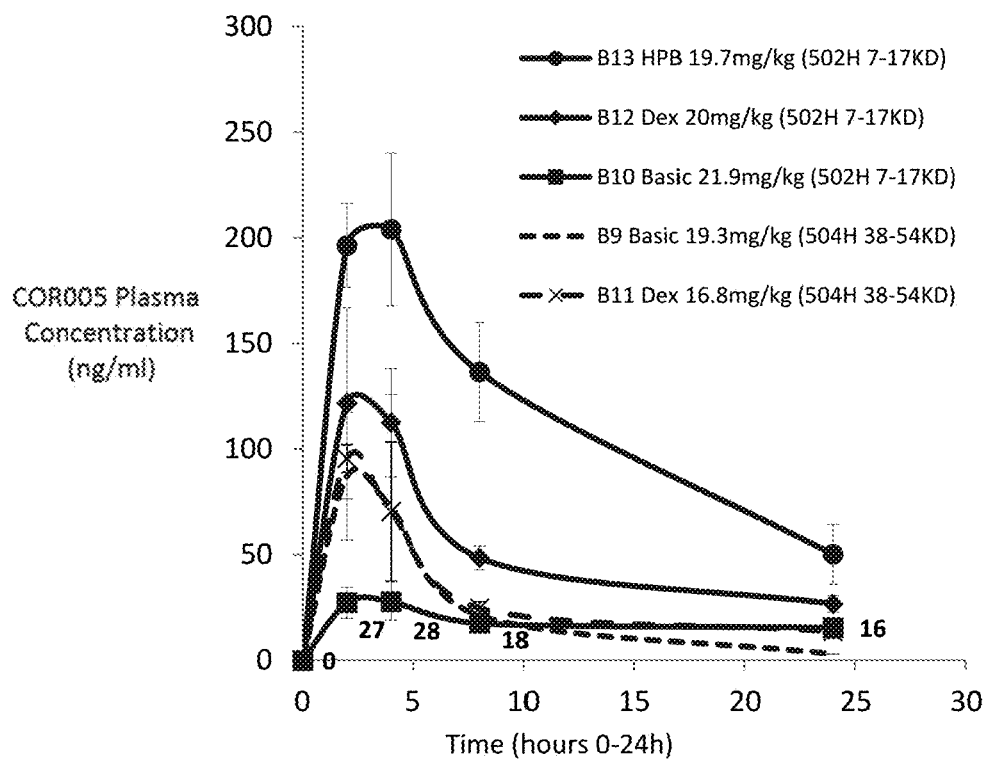
FIG. 12 shows a graph of the "Burst" pharmacokinetics of SC treatment groups B9-13 for a single SC Dose.

FIG. 12 shows a graph of the "Burst" pharmacokinetics as a Standard Plot of COR005 Plasma Concentration Time Curves of the means±STDEV of SC treatment groups B9-13 PLGA-MS-COR005 Acetate (time 0-24 hrs) for a single SC Dose, Rats (n=16).

Figure 13:
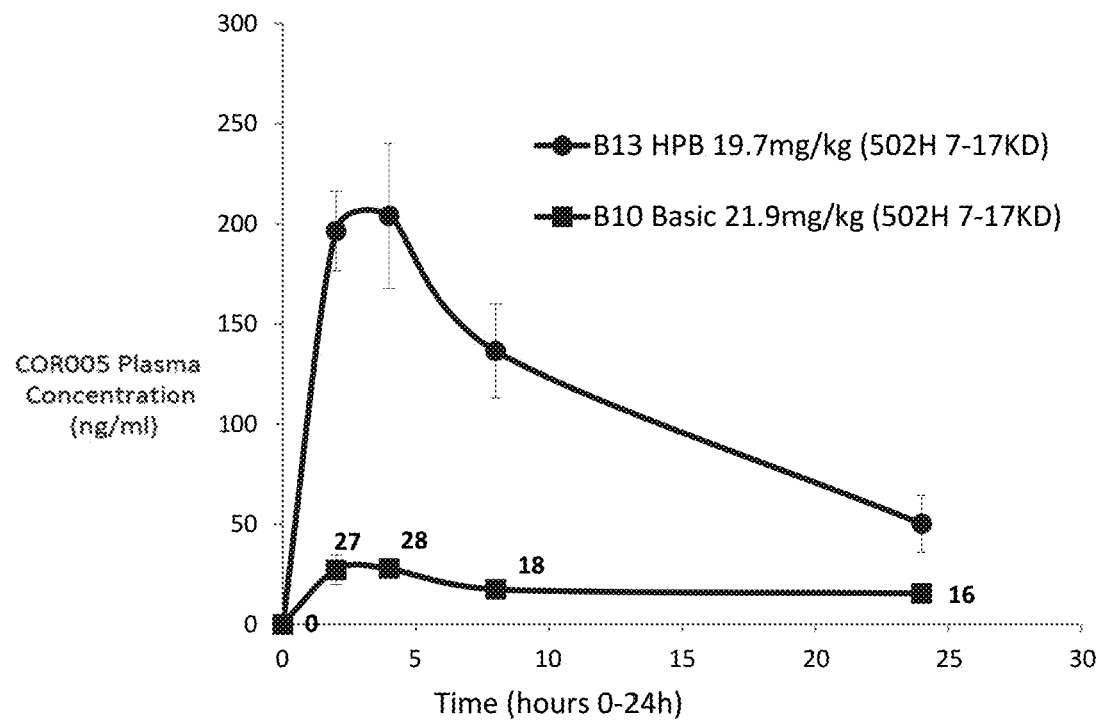
FIG. 13 shows the effect of HPB on the burst release of COR005 PLGA MS.

FIG. 13 shows the effect of HPB on the burst release (time 0-24 hrs) of COR005 PLGA MS in comparison to the basic MS formulation.

Table 15 summarizes the Pharmacokinetic parameters of COR005 Acetate burst release from MS formulations in rats, showing the effect of HPB on COR005 Cmax and absolute BA.

TABLE 15

| | Formulations | Dose (mg/kg) | Cmax "burst" (ng/ml) | AUC 0-24 h "burst" (ng*h/ml) | F % Absolute BA of the burst |
| --- | --- | --- | --- | --- | --- |
| B10 | Basic MS-PLGA (7-17 kDa) | Mean ± SD (n = 4) | 22 ± 2.8 | 30 ± 5 | 437 ± 80 | 2% |
| B13 (HPB:PEP 1:2) | HPB MS-PLGA (7-17 kDa) | Mean ± SD (n = 4) | 20 ± 1.3 | 211 ± 25 | 2771 ± 313 | 11% |

Figure 14:
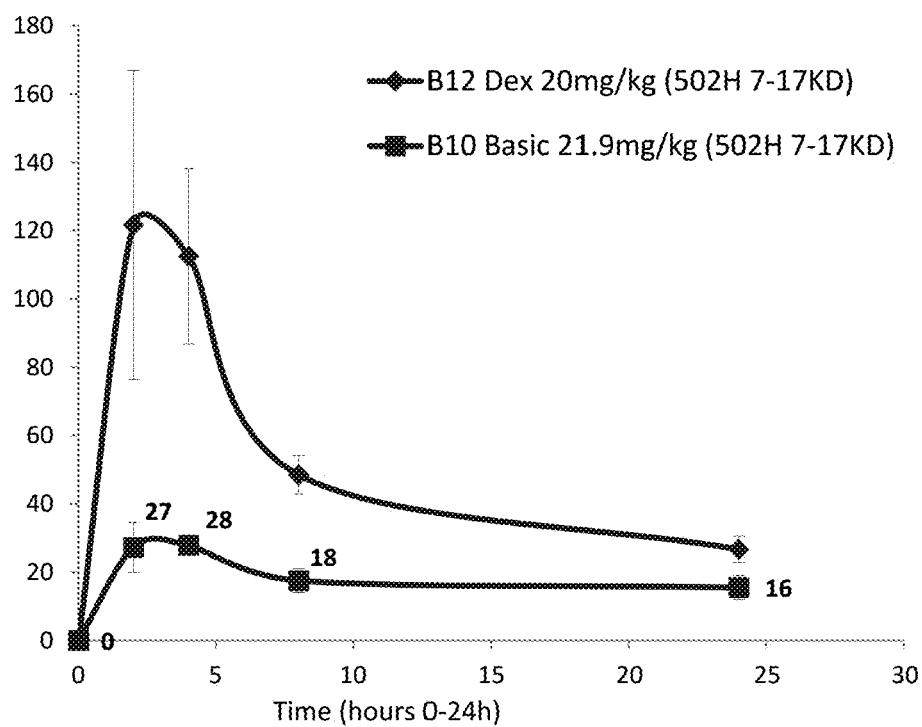
FIG. 14 shows the effect of DEX on the burst release of COR005 PLGA MS.

FIG. 14 is a graph showing the effect of DEX on the burst release (time 0-24 hrs) of COR005 PLGA MS in comparison to the basic MS formulation.

Table 16 summarizes the Pharmacokinetic parameters of COR005 Acetate burst release from MS formulations in rats, showing the effect of DEX on COR005 Cmax and absolute BA.

TABLE 16

| | Formulations | | Dose (mg/kg) | Cmax "burst" (ng/ml) | AUC 0-24 h "burst" (ng*h/ml) | F % Absolute BA of the burst |
| --- | --- | --- | --- | --- | --- | --- |
| B10 | Basic MS-PLGA 7-17 kDa | Mean ± SD (n = 4) | 22 ± 2.8 | 30 ± 5 | 437 ± 80 | 2% |
| B12 (DEX:PEP 1:8) | Dextrose MS-PLGA 7-17 kDa | Mean ± SD (n = 4) | 20 ± 2.4 | 113 ± 42 | 1280 ± 216 | 5% |

Table 17 summarizes the Absolute and Relative Bioavailability Values of Whole PK Profile—COR005 MS-PLGA 7-17 kDa—Formulation B13 in Rats (time 0-28 days).

TABLE 17

Absolute Bioavailability (AUC 0-t) of COR005 MS-B13 (SC) versus COR005 IR (IV)

| AUC(0-t) ng*h/ml IR M1 (IV) 1918 | AUC(0-t) ng*h/ml MS-B13 (SC) 12747 | Dose COR005 IR-MI (IV) 1.5 mg/Kg Dose COR005 MS-B13 (SC) 19.7 mg/kg | F = (1.5 * 12747)/(19.7 * 1918) * 100 | F = 51% |

Relative Bioavailability (AUC 0-t) of COR005 MS-B13 (SC) versus COR005 IR M5 (SC)

| AUC(0-t) ng*h/ml IR-M5 (SC) 3254 | AUC(0-t) ng*h/ml MS-B13 (SC) 12747 | Dose COR005 IR-M5 (SC) 3 mg/Kg Dose COR005 MS B13 (SC) 19.7 mg/kg | F = (3 * 12747)/(19.7 * 3254) * 100 | F = 60% |

Absolute Bioavailability (AUC 0-∞) of COR005 MS-B13 (SC) versus COR005 IR M1 (IV)

| AUC (0-∞) ng*h/ml IR M1 (IV) 1918 | AUC (0-∞) ng*h/ml MS-B13 (SC) 18487 | Dose COR005 IR-M1 (IV) 1.5 mg/Kg Dose COR005 MS-B13 (SC) 19.7 mg/kg | F = (1.5 * 18487)/(19.7 * 1918) * 100 | F = 73% |

Relative Bioavailability (AUC 0-∞) of COR005 MS-B13 (SC) versus COR005 IR M5 (SC)

| AUC (0-∞) ng*h/ml IR-M5 (SC) 3254 | AUC (0-∞) ng*h/ml MS-B13 (SC) 18487 | Dose COR005 IR-M5 (SC) 3 mg/Kg Dose COR005 MS B13 (SC) 19.7 mg/kg | F = (3 * 18487)/(19.7 * 3254) * 100 | F = 87% |

Table 18 summarizes the effects of additives HPB and DEX of COR005 acetate PLGA-MS formulations in minipigs.

TABLE 18

| COR005 PLGA-MS Formulations | PK Parameters | | |
| --- | --- | --- | --- |
| | Dose (mg/Kg) | Cmax (ng/ml) | F % BA (AUC 0-7 days) |
| B10 | 2.3 | 1.4 | ~1 |
| B13-HPB:PEP 1:2 | 2.2 | 47 | 26 |
| B14-HPB:PEP 1:4 | 1.8 | 63 | ~100 |
| B12(PSI13)-DEX:PEP 1:8 | 2.9 | 12.6 | 21 |

Figure 15:
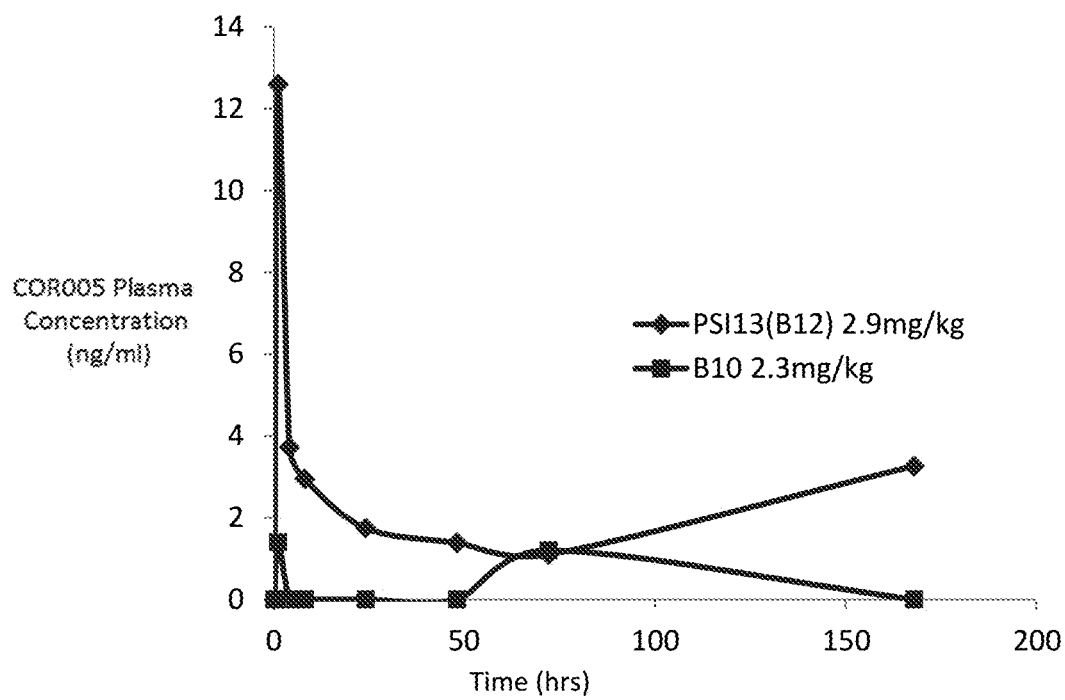
FIG. 15 shows the effect of DEX:PEP 1:8 in minipigs with PK profiles of microspheres of PSI13 (B12: DXE:PEP 1:8).
Figure 16:
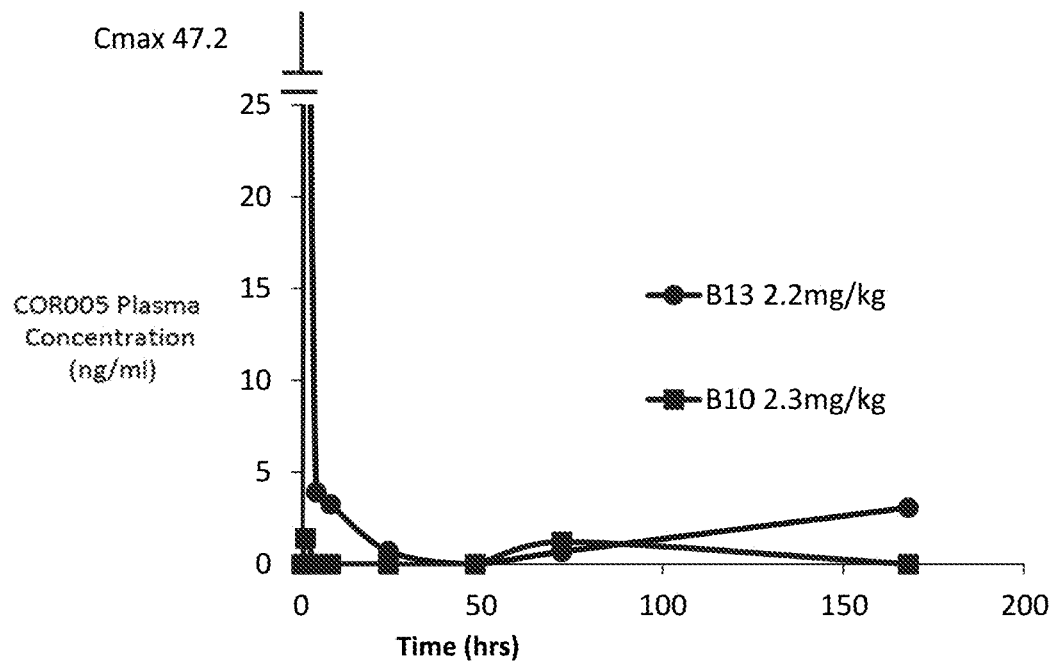
FIG. 16 shows the effect of HPB:PEP 1:2 in minipigs with PK profiles of burst release microsphere formulation B13.
Figure 17:
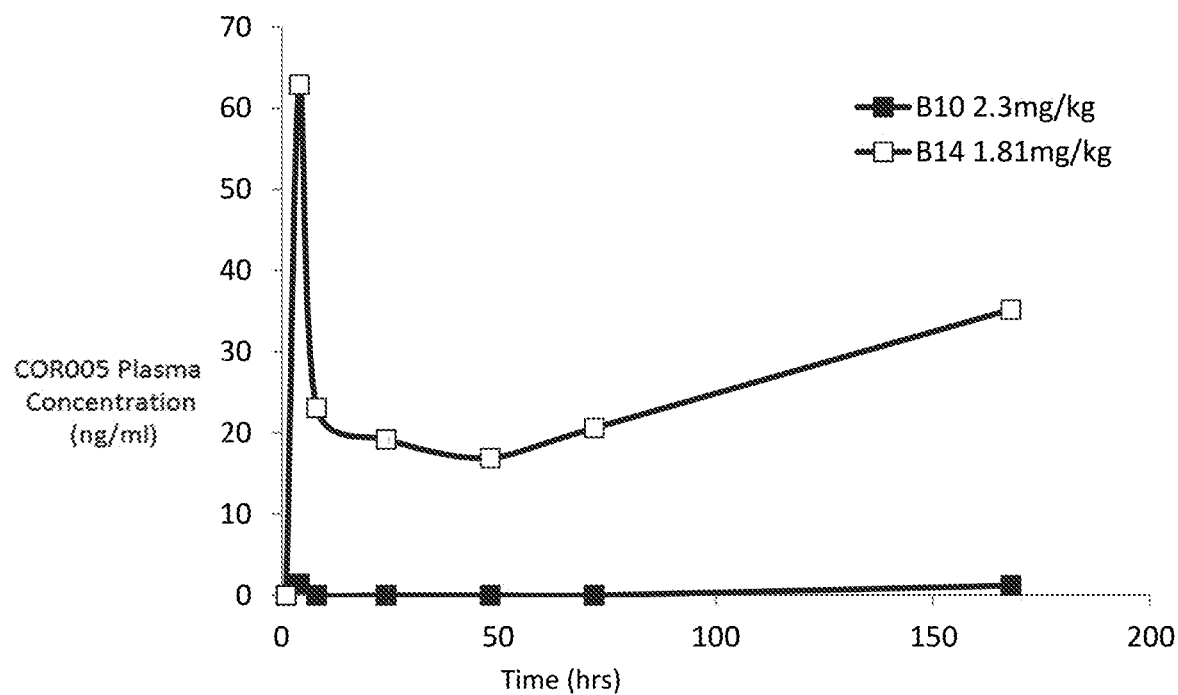
FIG. 17 shows the effect of HPB:PEP 1:4 in minipigs with PK profiles of burst release from microspheres of composition B14.

FIG. 15 shows the effect of DEX:PEP 1:8 in minipigs with comparative PK profiles of microspheres of PSI13 (B12: DXE:PEP 1:8) in comparison to B10 (basic MS formulation) as a control. FIG. 16 shows the effect of HPB:PEP 1:2 in minipigs in a graph of comparative PK profiles of burst release microsphere formulation B13 in comparison to B10 (basic MS formulation) as a control. FIG. 17 shows the effect of HPB:PEP 1:4 in minipigs as a graph of comparative PK profiles of burst release from microspheres of composition B14 in comparison to B10 (basic MS formulation) as a control.

Tables 19 and 20 summarize the peptide content and encapsulation efficiency (EE) of bulk samples of microspheres, measured by HPLC.

TABLE 19

| Sample | Peptide Content (%) | Encapsulation Efficiency EE (%) |
| --- | --- | --- |
| B9 | 4.52 | 65 |
| B10 | 11.53 | 79 |
| B11 | 3.95 | 55 |
| B12 | 11.53 | 81 |
| B13 | 11.82 | 74 |

TABLE 20

| | PSI-6 | PSI-7 | PSI-8 | PSI-9 | PSI 10 | PSI-1 (as B14) | PSI-13 (as B12) |
| --- | --- | --- | --- | --- | --- | --- | --- |
| Theoretical | | | | | | | |
| Theoretical Peptide, wt % | 23.7 | 24.6 | 28.6 | 23.7 | 27.7 | 22.9 | 27.5 |
| HPB Cyclodextrin %(mg) | — | — | — | 3.4 (150) 1:8 HPB:bulk pep | 3.2 (150) 1:10 HPB:bulk peptide | 6.7 (300) 1:4 HPB:bulk pep | |
| Dextrose | 3.4 (150) | — | — | | | | 4.0(187.5) |

TABLE 20-continued

| | PSI-6 | PSI-7 | PSI-8 | PSI-9 | PSI 10 | PSI-1 (as B14) | PSI-13 (as B12) |
|---|---|---|---|---|---|---|---|
| % (mg) | 1:8 Dex:bulk pep | | | | | | 1:8 Dex:bulk pep |
| Results | | | | | | | |
| Measured Peptide content, wt % | 17.5 | 17.8 | 19.5 | 17.3 | 17.6 | 16.4 | 19.3 |
| Encapsulation Efficiency, % | 74% | 72% | 68% | 73% | 64% | 72% | 70% |

Figure 18:
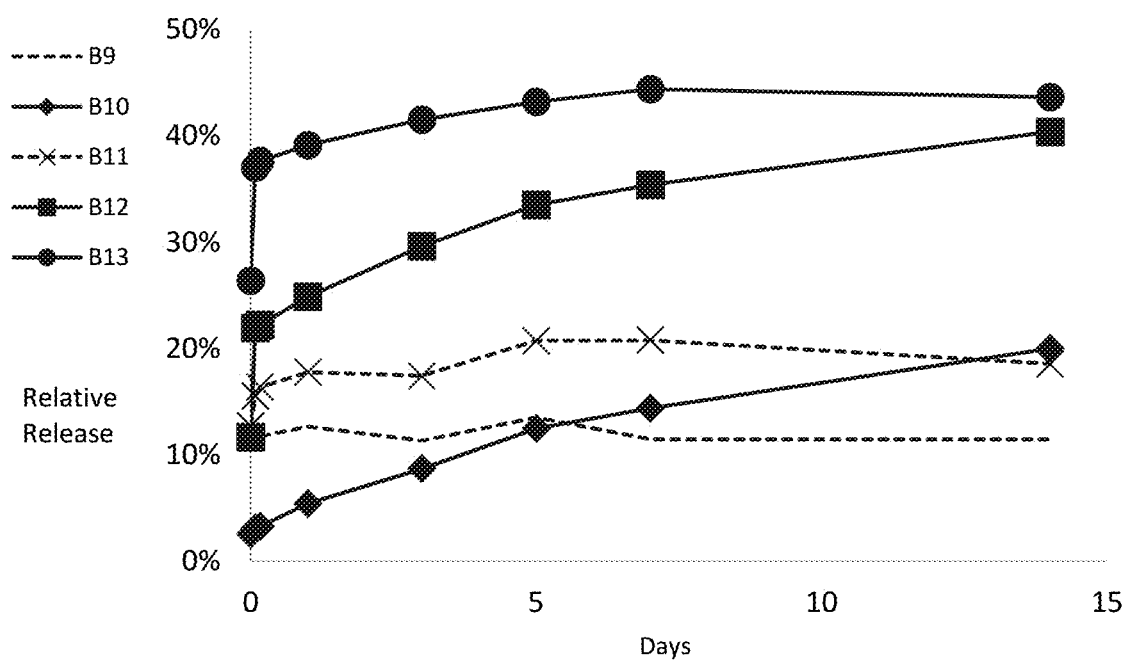
FIG. 18 shows comparative IVR Profiles of COR005 from microsphere formulations B9-13.

In vitro release (IVR) of veldoreotide acetate from the PLGA microspheres was measured. 50 mg of each microsphere batch (B9-B13) was added to 10 mL of phosphate buffer (10 mM, pH=7.4, without calcium, magnesium or chloride) in a 20 mL glass vial. The vials were maintained at 37° C. on a temperature-controlled shaker at 150 rpm. Samples were collected at various timepoints and analyzed via a NANOVUE® UV-Vis spectrophotometer at 280 nm against a standard calibration curve. Table 21 summarizes the results. FIG. 18 shows comparative IVR Profiles of COR005 from microsphere formulations B9-13.

TABLE 21

| Time (day) | B9 IVR (%) | B10 IVR (%) | B11 IVR (%) | B12 IVR (%) | B13 IVR (%) |
|---|---|---|---|---|---|
| 0 | 10.4% | 2.6% | 12.7% | 11.6% | 26.4% |
| 0.08 | 11.4% | 3.1% | 15.5% | 21.9% | 37.0% |
| 0.17 | 12.0% | 3.3% | 16.3% | 22.2% | 37.6% |
| 1 | 13.3% | 5.4% | 17.7% | 24.9% | 39.1% |
| 3 | 12.6% | 8.7% | 17.4% | 29.6% | 41.5% |
| 5 | 14.1% | 12.5% | 20.7% | 33.5% | 43.2% |
| 7 | 14.0% | 14.4% | 20.7% | 35.4% | 44.4% |
| 14 | 13.7% | 20.0% | 18.6% | 40.4% | 43.6% |

The comparative IVR profiles of COR005 from microspheres formulations B9 to B13 are depicted in FIG. 18 and Table 21 above. The data shows a significant difference between the two specific types of PLGA 50:50 that were used for the microspheres preparations. The accumulated amount of the released peptide, and the release rate were both significantly increased from the microspheres prepared with the low molecular weight polymer 7-17 kDa (7-17 KD) in comparison to the microspheres prepared with the higher molecular weight 38-54 kDa (38-54 KD). The comparative in vitro release profiles between HPB or DEX (B13 and B12 respectively) in comparison to the basic formulation B10 (without additives) show that the additives HPB or DEX increased the release rate and the total accumulated peptide released from microspheres above the basic formulation. The in vitro release profile of COR005 from B13, which was prepared with the additive HPB, shows the highest burst release of about 40%. The burst release was followed by a very low release rate during the next 14 days ending with a total release of about 45% at day 14. Note that the IVR profile of B13 is correlated with its PK profile as shown in the PK data in rats and in minipigs. The in vitro release profile of COR005 from B12, which prepared with the additive dextrose, shows a reduced burst release of about 20% in comparison to B13. The burst release from B12 was followed by a continuous increase in release rate over the time course of 14 days, ending with a total release of about 40% at day 14. This in vitro release profile of the comparative burst release of B12 versus B13 and B10 is correlated with the PK profile of B12 in rats and minipigs. The in vitro release profile of COR005 from the basic formulation—B10, which prepared with no additives, shows significantly low burst of about 5%. The burst release from B10 was followed by a continuous increase of release over the time course of 14 days, ending with a total release of about 20% at day 14. The observed release rate from B10 and the total accumulated peptide released from these microspheres were significantly lower in comparison to B12 and B13. The observed in vitro burst release from B10 is correlated with its PK profile. B10 exhibits a lower burst release in vivo in comparison to B12 and B13 in rats and minipigs.

Results for the "burst" kinetics (0-24 hours) of the formulations and injection site reactions over 28 days are shown in Tables 22 and 23, respectively. The pharmacokinetic profiles for the different formulations are shown in FIGS. 11 through 18.

TABLE 22

| Formulation | Mean Dose (mg/kg) | Mean $C_{max}$ "burst" (ng/mL) | Mean $AUC_{0-24\,h}$ "burst" (ng * h/mL) |
|---|---|---|---|
| B9 | 19 | 88 | 628 |
| B10 | 22 | 30 | 437 |
| B11 | 17 | 96 | 759 |
| B12 | 20 | 133 | 1280 |
| B13 | 20 | 211 | 2771 |

TABLE 23

| Formulation | Mean Peptide at Injection Site (mg, estimated), IVR | ISR "burst" 6 hours | ISR "burst" 24 hours | ISR 4 days | ISR 28 days |
|---|---|---|---|---|---|
| B9 | 0.65 | 2-3 | 2 | 1-2 | Recovery |
| B10 | 0.4 | 2 | 2 | 1-2 | Recovery |
| B11 | 1 | 2-3 | 2 | 1-2 | Recovery |
| B12 | 1 | 3-4 | 3-4 | 1-2 | Recovery |
| B13 | 1 | 5 | 5 | 4 | 1-2 |

*Injection site reactions are rated from 1-5 with 1 = tolerated and 5 = worse (See Table 24)

TABLE 24

| ISR Score | 24 h | Week | Month |
|---|---|---|---|
| 1 | NOEL | NOEL | Recovery NOEL |
| 2 | Slight Swelling | No redness | Recovery/scar |
| 3 | Mild Swelling | Slight redness | Slight alopecia |
| 4 | Swelling | Mild redness/scab | Slight redness Alopecia |
| 5 | Swelling + edema | Scab/Hemorrhage | Redness and alopecia |

As shown in Table 23, in rats it appears that tolerability is <0.5 mg at the injection site and about 1 mg induces injection site reaction.

PLGA microspheres from each batch prepared in this example were also subjected to electron microscopy (SEM). Resulting images are shown in FIGS. 19-27.

As may be observed from FIGS. 12 and 13, formulation B13 (veldoreotide acetate in low molecular weight PLGA microspheres with hydroxypropyl-β-cyclodextrin) exhibited increased "burst" release compared to other formulations of veldoreotide acetate during the first 24 hours followed by sustained release for 28 days with a defined $C_{min}$. Formulations B10 and B12 (veldoreotide acetate in low molecular weight PLGA microspheres without and with dextrose, respectively) exhibited a smaller "burst" followed increasing releasing from about weeks 2 through 4 without increasing injection site reaction indicating sustained release with improved tolerability. B12 specifically demonstrated a significantly higher bioavailability (AUC) than the extrapolated AUC for B13. However, PLGA microspheres containing veldoreotide acetate prepared with either hydroxypropyl-β-cyclodextrin or dextrose exhibited enhanced release in the "burst" phase over PLGA microspheres without the excipients. It is suspected, without being limited to the theory, that these excipients result in increased porosity and surface area of the microspheres. Overall, B10 was the most tolerated formulation resulting in plasma levels ($C_{max}$) of about 30 ng/mL during the "burst" phase. It is also notable that IVR is inversely correlated with injection site reactions and may be used to predict the injection site reaction potential for formulations.

Comparative SEM Imaging of COR005 Acetate PLGA-MS Formulations Showing the Effects of Additives The first aim of the SEM imaging was to evaluate and compare the external morphology of the various MS formulations and to verify the effects of the additives HPB and DEX on droplet size and surface tension. The second aim was to evaluate and compare the internal structures of the various MS matrices. More specifically, to identify possible differences between the various internal matrices that correlate with the suggested unique interactions between COR005, the additives (DEX and HPB) and the hydrophobic PLGA polymer (during the primary emulsion and during the release of peptide at the injection site, from the final MS) and the effects of these interactions on the observed IVR and PK profiles of COR005 (with or without additives).

Figure 19:
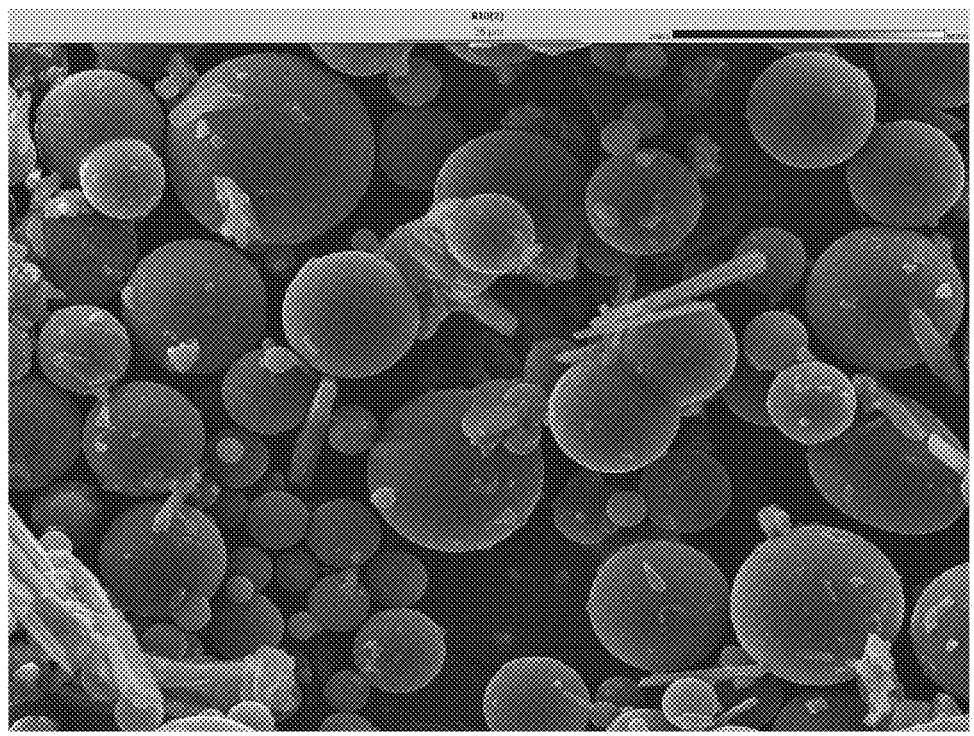
FIG. 19 shows a SEM micrograph of the external morphology of basic microsphere formulation B10.
Figure 20:
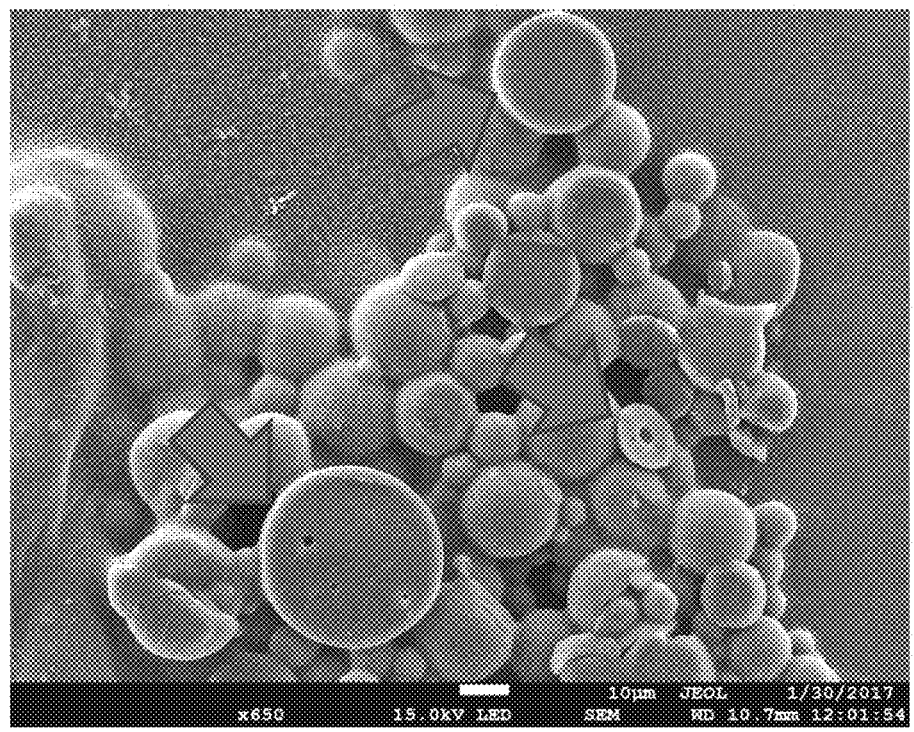
FIG. 20 shows a photomicrograph of the internal morphology of basic microsphere formulation B10.

FIG. 19 shows a SEM photomicrograph of the external morphology of basic microsphere formulations B10 of COR005 acetate without additives. FIG. 20 shows a photomicrograph of the internal morphology of basic microsphere formulations B10 of COR005 acetate without additives. In FIG. 20, arrows indicate microspheres that are cut open to show the internal morphology.

FIGS. 19 and 20 depict the external and internal morphologies of the basic formulation B10. The primary emulsion of this MS formulation was based on mixing the peptide water solution with the polymer in methylene chloride, without any other additives. Note that under these preparations conditions, COR005 possesses its maximal surface activity (as depicted in Tables 2, 3, and 4). FIG. 19 depicts the symmetrical shape of Formulation B10 MS and the relatively smooth external surface of the MS with only a few small pores. Therefore, another SEM series was performed following the cutting of MS samples in order to evaluate the consequence of these external pores with the internal morphology of the MS. The SEM image of FIG. 20 shows the exposed internal structure of the MS as a result of cryo-cutting. The observed internal matrix has a solid texture with only few pores, which correlates with the observation of the external surface of this basic B10 formulation. Based on these SEM observations, Formulation B10 is best described as a microsphere with relatively low permeability. These results support the assumptions of the high affinity between the COR005 and the polymer, which result with relatively smooth external surface and solid and condensed internal matrix. This morphology is due to the unique surface activity of COR005 as a water-in-oil, relatively hydrophobic surfactant and its orientation at the interface with the polymer methylene chloride solution as hydrophobic surface (FIG. 20 and Tables 3, 4 and 5). As a consequence of this peptide:polymer physical (not chemical) interaction the expected release of the peptide from Formulation B10 should be relatively slow. Indeed, the IVR data show that the release rate of COR005 from Formulation B10 is the slowest in comparison to the HPB and DEX MS formulations. This slow release rate correlated with the in vivo PK profile of B10, which has the lowest burst release (Cmax) as observed in rats and minipigs and the lowest plasma levels observed in the minipigs in comparison to Formulations B12, B13 and B14 (table 3). Note that the PK in rats indicated an increase of plasma levels of COR005 from the B10 MS formulation above Formulations B12 and B13, however due to the significant variability associated with the B10 animal group, the results were inconclusive. The determinative correlation between the slow release COR005 from Formulation B10 and poor plasma levels and low BA was evidenced in the PK studies in minipigs as depicted in Table 3. The release rate of COR005 from the basic B10 formulation was too slow to overcome the clearance rate of COR005 in minipigs and as a result the poor plasma levels were obtained over time.

The External and Internal Morphology of B12 Formulation with DEX

Figure 21:
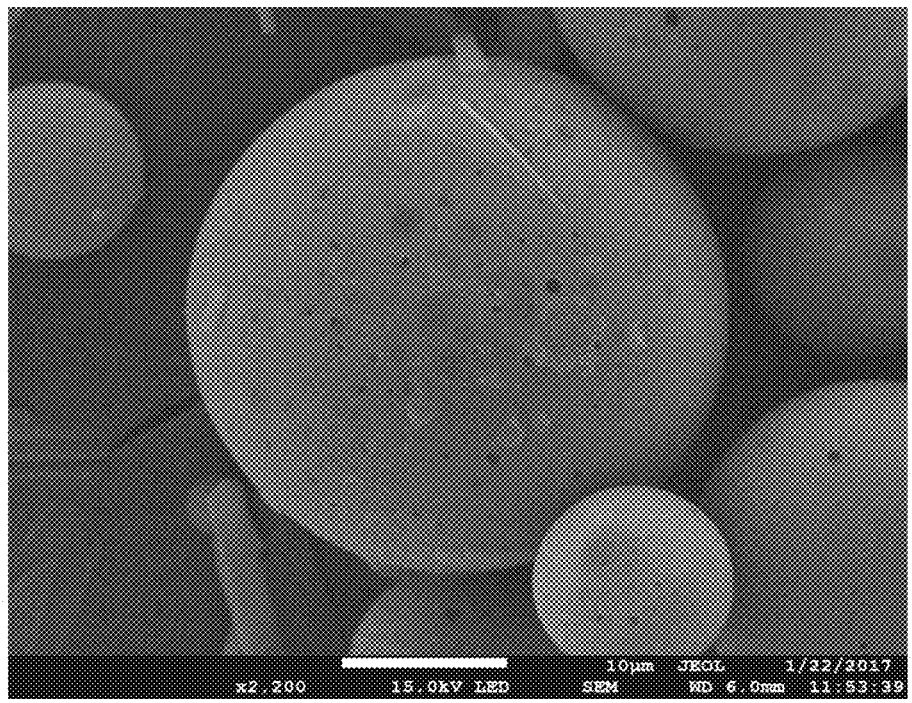
FIG. 21 shows an SEM image of the external morphology of formulation B12.
Figure 22:
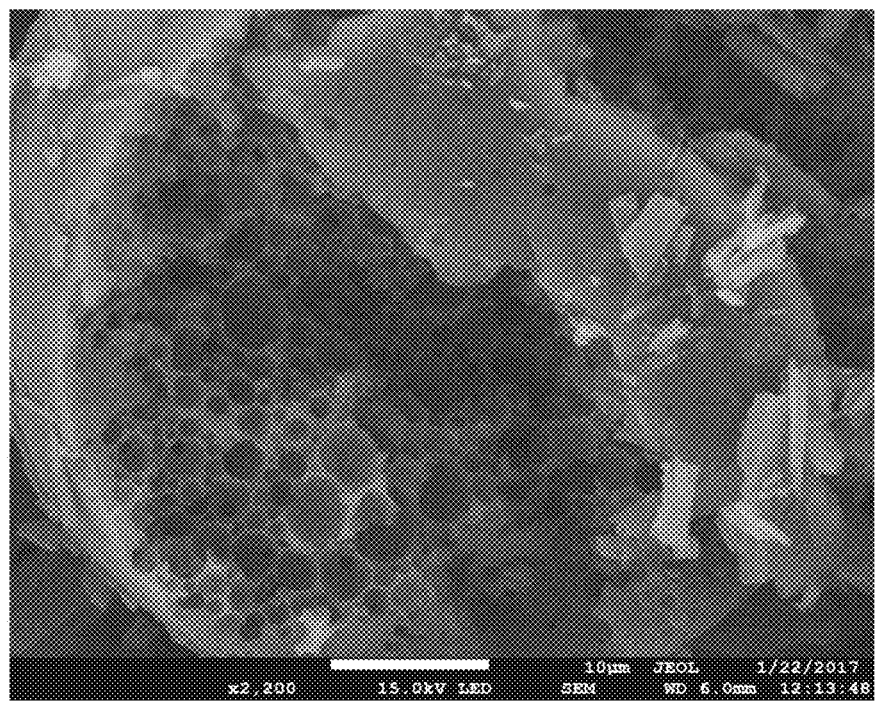
FIG. 22 shows an SEM image of the internal morphology of formulation B12.
Figure 23:
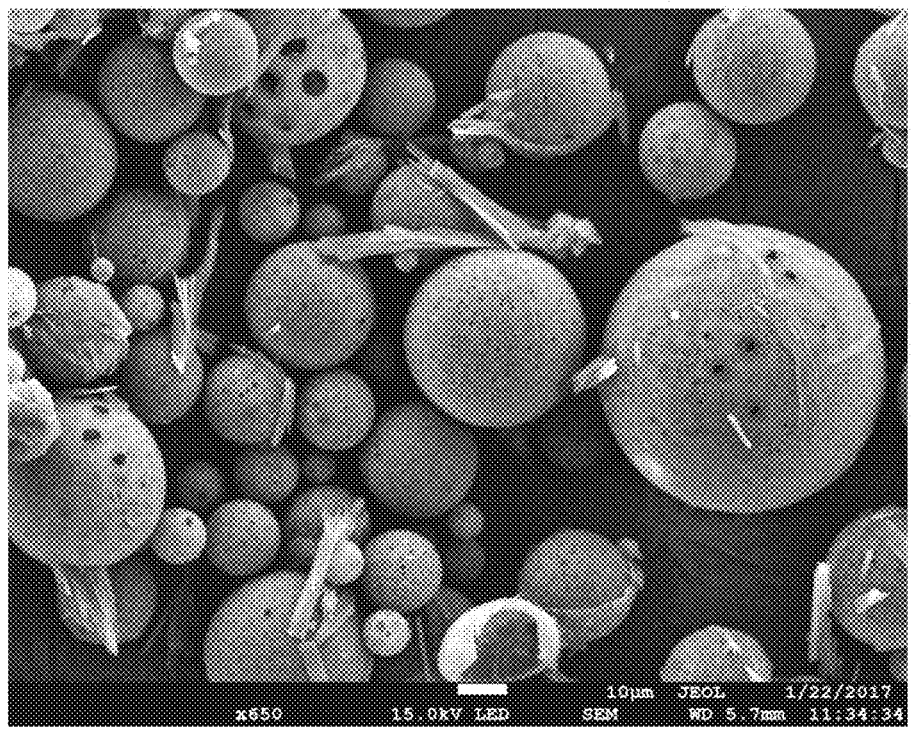
FIG. 23 shows an SEM image of the external morphology of formulation B13.
Figure 24:
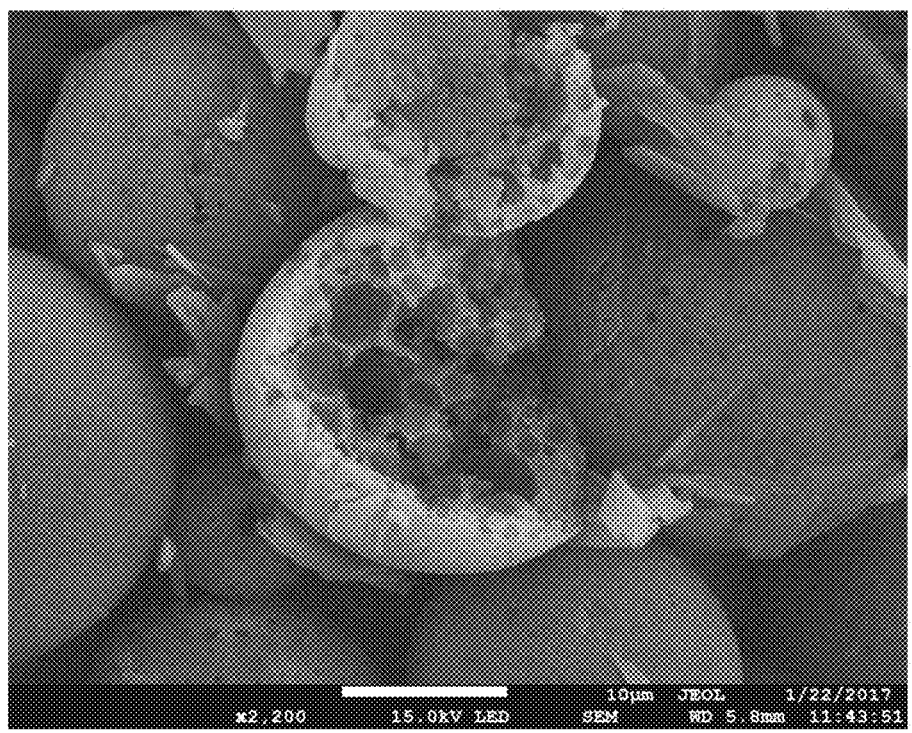
FIG. 24 shows an SEM image of the internal morphology of formulation B13.
Figure 25:
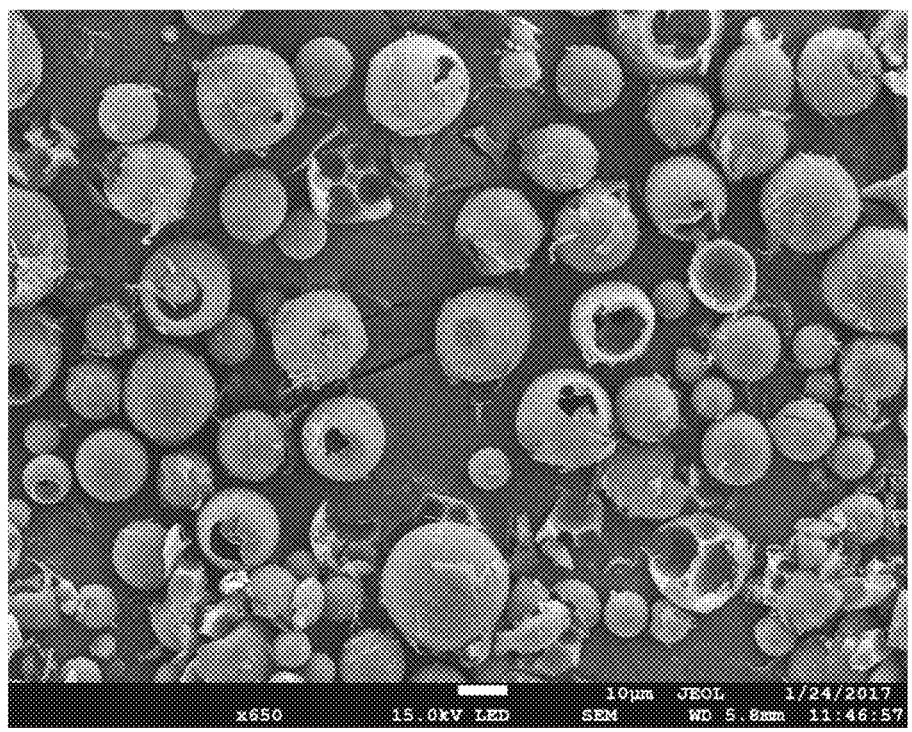
FIG. 25 shows the external and internal morphologies of a placebo MS with HPB but no peptide.
Figure 26:
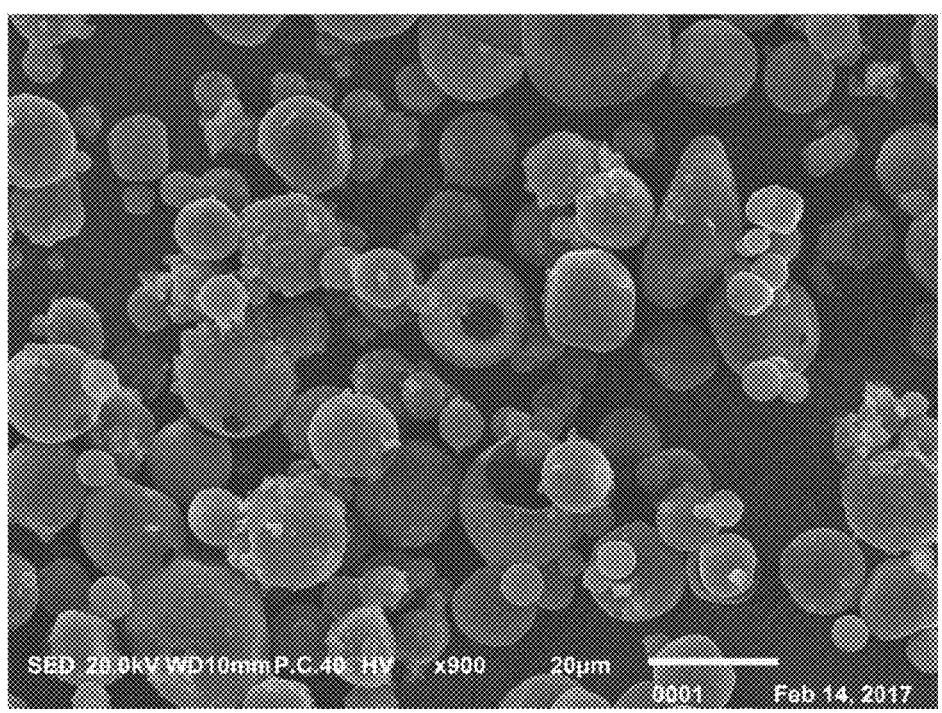
FIG. 26 shows the external and internal morphologies of a placebo MS with DEX but no peptide.
Figure 27:
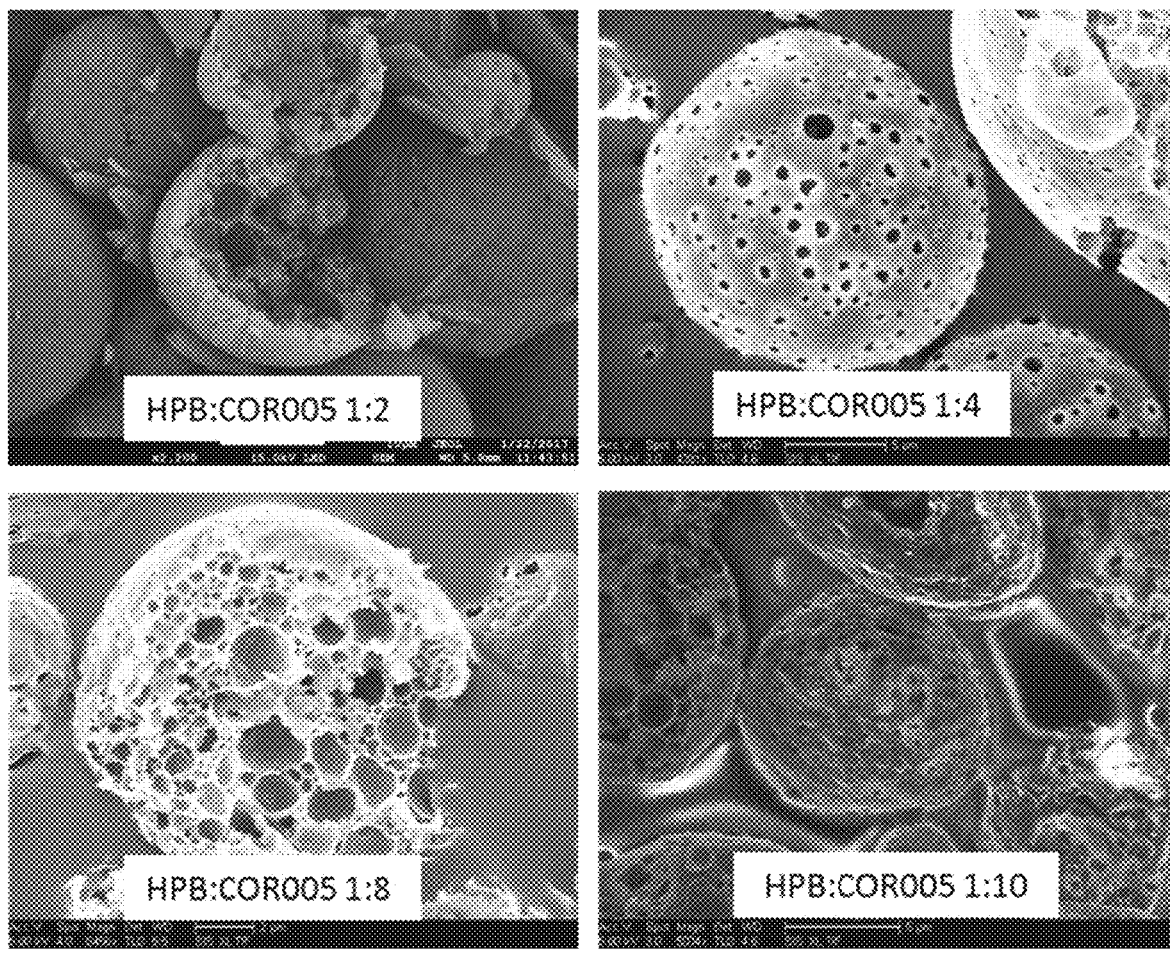
FIG. 27 shows SEM images of the morphology of internal matrices of MS formulations with various ratios of HPB: PEP.

FIGS. 21 and 22 depict the SEM images of the external and internal morphologies of Formulation B12 (PLGA-MS-DEX) respectively. The image depicted in FIG. 21 shows a representative MS of Formulation B12 with a significant high porosity of the external surface as a result of many pores visible at the surface, in comparison to the very few pores observed in the basic B10 formulation. In FIG. 22 the internal matrix of Formulation B12 is exposed after cryo-cutting of the MS. The image shows a significantly high number of voids separated by relatively thin interstitial polymeric boundaries, which result in a high density of small voids in the internal matrix and therefore, increased void volume. The first expected impact of this increased void volume is a reduced polymer density in the internal matrix. For a given volume of MS, more voids inside the MS equals less polymer due to the internal space of the voids. The second expected result of this high void volume is reduced peptide content in the MS. Less polymer in the matrix may lead to less encapsulation of the peptide inside the MS. The third expected impact of this high void volume is a rapid release of the encapsulated peptide from Formulation B12 MS with less duration of release in comparison to the solid and denser matrix of Formulation B10 basic MS.

However, unexpectedly, all of three anticipated results were not observed in the IVR and PK data of COR005. The IVR data (see below) shows prolonged and constant release of COR005 from Formulation B12 over Formulation B10 and the PK shows increased plasma levels over time and higher absolute BA of Formulation B12 above Formulation B10.

These results point to the fact that in the case of the primary emulsion of COR005 with DEX, the peptide is not concentrated within the PLGA matrix but at the surface of the polymer of the internal voids. Because COR005 has a unique surfactant activity which results in high affinity of the peptide to the hydrophobic PLGA polymer it is concentrated at the interface of the polymer and the internal water phase of the primary emulsion. As a consequence, during the solidification stage of the MS with no additives; most of COR005 will be concentrated between the PLGA polymeric chains.

However, when DEX is added, the many voids created inside the matrix present many small spaces that result in enhanced surface area inside the MS. In this case the total surface area of the MS is increased by a significant manner above the case of Formulation B10 MS that has a relatively solid matrix. This results in the significant prolonged release of COR005 from B12 which is followed by increased plasma levels over prolonged period of time, which can be explained by the release of COR005 from the internal surface of the voids rather than from the solid polymeric structures. Only when the peptide is released from a surface the kinetics of this release correlates with the PK Another unexpected impact of the DEX in the PLGA MS is its effect on the COR005 dispersion and distribution during the primary emulsion and solidification of the MS. It was shown that dextrose improves the solubility of COR005 in water (Table 3 shows the high solubility in 5% dextrose solution of >500 mg/ml). This effect may be due to the potential hydrogen bonding between the dextrose and COR005 which change the peptide conformation to a more hydrophilic conformation with less hydrophobic moieties exposed on the outside of the molecule. In other words, the high hydrogen bonding capacity and affinity of water for the dextrose may help solubilize the peptide. This effect leads to improved dispersion and volume of distribution of the peptide within the MS. When the primary emulsion is added to the secondary emulsion which is an aqueous PVA phase, most of the dextrose leaks from the embryonic MS to the continuous phase. The peptide will adopt again its original hydrophobic conformation, which has high affinity to the PLGA and thereby concentrates at the interfacial surfaces of the voids and within the polymer matrix. This is supported by the very low recovery of the dextrose in the final MS of only about 0.5% of dextrose detected in the final MS out of the 4% theoretical loading (Table 25 below).

used in Formulation B13 (where no COR005 acetate was added). The external morphology of Formulation B13 as depicted in FIG. 23 supports the expected effect of HPB as a porosity agent in PLGA-MS. There are many pores at the surface with a wide range of pore diameters. However, FIG. 24 shows the internal structure of Formulation B13 MS after being cut by cryo-cutting, which points out the significant difference between the internal morphology of Formulation B13 versus Formulation B12. The internal structure of Formulation B13 exhibits a significant increase in the void size in comparison to the size of voids in Formulation B12 (FIG. 22). Moreover, the number of the internal bigger voids in Formulation B13 is reduced in comparison to the high density of the many small voids found in Formulation B12. These results show that in the case of Formulation B13, the increase of total surface area due to the creation of internal voids is less than in the case of Formulation B12.

Therefore, it is expected that the encapsulation efficiency of COR005 in Formulation B13 will be reduced in comparison to Formulations B10 and B12 due to internal surface area. However, the encapsulation efficiency of COR005 was similar for these three MS formulations. This means that COR005 will be concentrated with relatively high concentration near the external shell of the MS which may result with increase burst release. Moreover, the interaction between HPB and COR005 as an inclusion complex will result in increased concentration of the hydrophilic complex of the HPB with peptide. Due to this interaction between HPB and COR005, the hydrophilic complex will attract more water and will limit the solidification efficiency of PLGA, which will end with an internal matrix with relatively bigger holes as shown in FIGS. 23 and 24.

The molecular weight of HPB is significantly higher (roughly the same level of COR005) in comparison to DEX and therefore its mobility and dispersion in the internal space of the MS will be limited as well, in comparison to higher distribution volume of DEX. The apparent bigger size of the internal voids, as found in Formulation B13, and the consequent effect of the peptide surface activity associated with this internal surface area are correlated with the unique IVR and PK profile of Formulation B13. When water accesses the Formulation B13 MS inner space, an immediate release of peptide occurs due to the high presence of HPB near the peptide. Most of the HPB remained in the final MS as shown in Table 25, which results in the same HPB:PEP ratio as the theoretical HPB:PEP ratio of 1:2. In addition, the

TABLE 25

| Tested MS formulations | Theoretical peptide content COR005 acetate | Theoretical additives content (HPB:PEP or DEX:PEP ratios) HPB | DEX | Actual peptide content COR005 acetate | Actual (residual) additives content in final MS (HPB:PEP or DEX:PEP ratios) HPB | DEX |
|---|---|---|---|---|---|---|
| PSI 12 (as B14) Lot SOT1542_001-40 | 26.6% | 6.7% (1:4) | | 16.4% | 4.23% (1:3.9) | |
| PSI-13 (as B12) Evonik Lot # 1459-1 | 32% | | 4% (1:8) | 19.3% | | 0.57% (1:34) | surface activity of the peptide at the injection site is reduced, as depicted in Table 6 under these conditions. The result of these two effects is that most of the peptide will be concentrated as a hydrophilic complex with the HPB at the surface of the internal space of the big voids in the MS.

This data further supports the immediate release of most of the peptide load during the early stage of water penetra-

The External and Internal Morphology of B13 Formulation with HPB

FIGS. 23 and 24 depict the SEM images of external and internal morphologies of Formulation B13 MS. FIG. 25 depicts the external and internal morphologies of the placebo MS prepared as a control with the same amount of HPB tion (post injection) which will be followed by very poor release of the rest of encapsulated peptide. Moreover, in order to further confirm the COR005:HPB interaction and the impact of this unique interaction on the surface activity of the encapsulated peptide, a "placebo" MS formulation of B13 was prepared which was based on the HPB and PLGA combination as Formulation B13 but without the peptide COR005. FIG. 25 shows the SEM image of the "MS" morphology of B13 formulation without the COR005 acetate. This image clearly shows that encapsulation of HPB without COR005 results in hollow microcapsules rather than solid microspheres. More specifically, the HPB retains water as the MS is solidifying, potentially slowing the solidification of the PLGA in the embryonic MS. This effect would lead to significantly bigger holes/pores in the PLGA matrix, as was observed for the placebo, much bigger than those for in Formulation B13. This evidence further supports the interaction between HPB and COR005 which results in a unique and unexpected internal surface in the PLGA-MS formulations.

FIG. 26 shows an SEM micrograph of a similar "placebo" microsphere formulation of Formulation B12, using DEX and the excipient, without the peptide COR005. These Figures show the external and internal structure of microspheres prepared with only the additive (no COR005) in the same input amounts as the peptide containing formulations. The external morphology of the placebo microspheres show very few surface pores. Internally, there are a limited number of large internal voids. The microspheres are only a "shell" of polymer with a hollow core. These are sometimes referred to as microcapsules. Without being bound by any particular hypothesis, once the primary water-in-oil emulsion is formed the surface tension of only the WFI and additive allows the smaller droplets to coalesce. The polyvinyl alcohol (PVA) is holding the embryonic microspheres (primary emulsion) as discrete droplets. The solvent evaporation process is relatively slow, allowing the primary emulsion to form two phases: the inner water phase containing the additive and the outer polymer solution phase comprised of the polymer and methylene chloride. The surface of the MS has few pores that would have been created by a fine dispersion of water droplets within the organic polymer phase.

In FIGS. 23 and 24 we see the effect of adding COR005 along with HPB. The change in surface tension in the inner aqueous phase allows the smaller droplets of peptide and HPB to remain throughout the solvent evaporation process setting the internal and surface structure as depicted. Similarly, the combination of Dextrose and COR005 provides microspheres with a large number of small internal voids (FIG. 22).

The B14 (PSI12) Paradigm and the Improved Release Profile and PK of COR005 with HPB The unexpected data of Formulation B13 IVR and its PK profile, which show an immediate release of most of the encapsulated peptide content followed by significantly low plasma levels over time, provided the basis for the design of MS formulations with reduced ratios of HPB:PEP. The counterintuitive IVR and PK results show that the reduced ratio of HPB:PEP from 1:2 to 1:4 and even to 1:8 result in an unexpected increase in the peptide release from the MS. In order to investigate the link between these IVR and PK results with the unique surface activity of COR005, a detailed SEM analysis of the MS with reduced HPB:PEP ratios was undertaken with the aim to evaluate their internal morphology. FIG. 27 shows SEM images comparing the morphology of internal matrices of COR005 MS formulations with various ratios of HPB:PEP.

As can be seen from the comparative SEM images of FIG. 27, the reduced HPB:PEP ratio from 1:2 (Formulation B13) to 1:4 (Formulation B14) and further reduction to 1:8 and 1:10 results in an unexpected increase in the number of voids in the internal matrix of these microspheres. Moreover, the reduced ratio from 1:2 to 1:4 leads to another counterintuitive result of increased distribution of pores in the external surface of MS as can be seen at the HPB:PEP 1:4 example of B14 in comparison to B13. The inverse/unexpected effect of the reduced HPB:PEP ratio is further strengthened in the case of the minimal HPB:PEP ratio of 1:10 as depicted in the SEM image of this ratio, which shows an internal matrix which has significantly denser distribution of smaller voids.

In conclusion, as the HPB:PEP ratio is reduced more COR005 is oriented at the internal surface of the MS. This unique surface activity results in an increased and prolonged release of the peptide that is mainly due to the peptide release from the increased void-filled internal surface area. As a result, the peptide release will be enhanced and prolonged over time such as was observed in the IVR and PK studies in the case of Formulation B14. Note that the inverse relationship between the HPB:PEP ratio observed by the SEM analysis is also correlated with the comparative IVR study of these various HPB:PEP ratios.

Surface Area

The surface area for microspheres was measured using nitrogen gas adsorption on a Micromeritics ASAP 2020 instrument. Between 15-25 mg of microsphere is added to machine's analysis tube and sealed inside the tube with specialized seal frit. Analysis was undertaken in two stages: degassing and nitrogen adsorption measurement. Degassing is a process that applies heat and vacuum to remove moisture and other trapped gasses within the interior of the microspheres. Microspheres were degassed under vacuum (100 μmHg) and heated at 35° C. for 150 min. Afterwards the sample tube was transferred to the analysis valve of the instrument. The sample tube is lowered into a dewar of liquid nitrogen to cool the sample to 77° K. Nitrogen gas is added in a controlled fashion and tube pressure is monitored in order to generate an adsorption isotherm. From the isotherm, Brunauer-Emmett-Teller (BET) theory is applied in order to calculate a surface area per unit mass. Analysis time is approximately 4 hours, total run time is 6.5 hours per sample.

The concept of surface tension affecting the pore structure is again confirmed with the surface area measurement. The results for this test on several different microspheres prepared without excipient (PSI-7) and with either DEX or HPB (PSI-6 and PSI-12) as described above are summarized in Table 26.

TABLE 26

| MS Formulation | Excipient | BET Surface Area ($m^2/g$) |
|---|---|---|
| PSI-7 | None | 5.084 |
| PSI-6 | 3.4% DEX (DEX:PEP = 1:8) | 9.7437 |
| PSI-12 | 6.7% HPB (HPB:PEP = 1:4) | 77.7176 |

Higher levels of surface area are indicative of a greater number of internal voids in the microspheres.

The microspheres comprising veldoreotide acetate and either dextrose or HPB as excipients have a surface area of the plurality of polymeric microspheres microsphere from about 7 m²/g to about 12 m²/g, such as from about 7 m²/g to about 10 m²/g.

In comparison, microspheres prepared from PLGA and octreotide acetate with 0, 0.2%, or 1% of glucose had surface area of 4.4, 4.7 or 4.9 m²/g, respectively (*Biomaterials*, 2004, 25, 1919-1927).

Example 5

Veldoreotide was formulated as a water in oil emulsion using 80% (wt %) cottonseed oil, 20% (wt %) water for injection (WFI) and 1% (wt %) veldoreotide acetate. Specifically, 10 mg of veldoreotide acetate was dissolved in 200 uL WFI in a 5 mL glass vial, 800 mg of cottonseed oil was added and the resulting mixture was stirred under magnetic stirring at room temperature for 15 minutes at 1000 rpm. The emulsion was then viewed under the light microscope and stored under refrigeration. The resulting emulsion was stable and found to be injectable via 27G needle.

Veldoreotide acetate was also formulated as a hydrogel using 0.7% (w/v) carboxymethylcellulose sodium salt (SIGMA C5013) high viscosity, 37.5% (w/v) hydroxypropyl-β-cyclodextrin and 0.5% (w/v) veldoreotide acetate. Specifically, 10 mg of veldoreotide acetate was mixed with 75 mg of hydroxypropyl-β-cyclodextrin in 2 mL WFI and mixed in a 5 mL glass vial until clear. The 14 mg carboxymethylcellulose sodium salt was added slowly by pouring into the mixture under magnetic stirring at room temperature followed by storage under refrigeration. The resulting hydrogel was also found to be injectable via 27G needle. Surprisingly, it was found that the order of formulation was critical to gel stability. Combination of veldoreotide acetate with hydroxypropyl-β-cyclodextrin followed by addition of carboxymethylcellulose resulted in a stronger hydrogel than adding carboxymethylcellulose to veldoreotide acetate first or combining the components simultaneously. Interestingly, combination of hydroxypropyl-β-cyclodextrin with carboxymethylcellulose alone did not result in gel formation. Therefore, it is believed that, without being bound to the theory, the polymer interacts with the cyclodextrin and the peptide due to its unique properties to result in formation of a stable gel.

Both the emulsion formulation and hydrogel were injected into rats at a dose of 1 mg per injection site using 27G needles, one formulation on each side of the rat. Swelling was not observed at the injection site for either formulation until 48 hours post-dosing. At 48 hours post-dosing, swelling was observed at the injection site for the hydrogel only and not for the emulsion. At 72 hours post-dosing, swelling and a small wound was observed for the gel formulation. Injection sites for the emulsion formulation did not exhibit any significant injection site reaction with no swelling and no alopecia observed.

Rats were sacrificed and necropsied to assess the injection site reaction sub-dermally. At the injection site for the hydrogel, at 72 hours, edema and signs of local inflammation were found, including a thickening of the sub dermis. At the injection site for the emulsion, at 48 hours, the sub-dermal tissue was benign with no signs of swelling, edema, inflammation or thickening of the sub dermis observed.

Example 6

Figure 28:
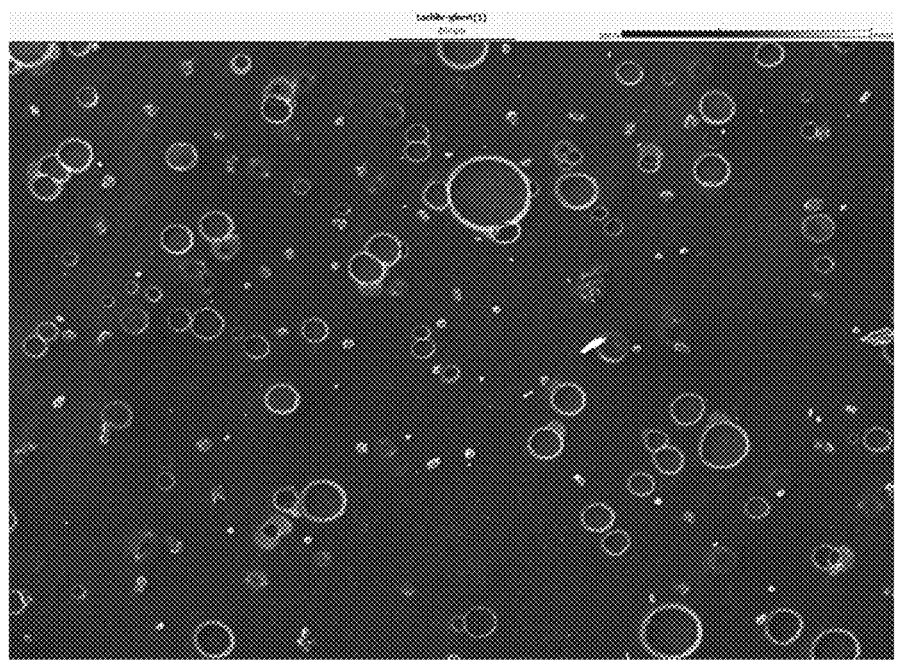
FIG. 28 shows a SEM micrograph of liposomes formulated with veldoreotide acetate.

Veldoreotide acetate was formulated into liposomes (multilamellar vesicles) by combining veldoreotide acetate and 1,2-dimyristoyl-sn-glycero-3-phosphocholine (DMPC) at a 1:10 ratio, by combining 7 mg veldoreotide acetate and 70 mg DMPC (14:0 PC (DMPC) 1,2-dimyristoyl-sn-glycero-3-phosphocholine 850345 by Avanti, 7 weight %) in 1 mL WFI in a 5 mL glass vial. The mixture was stirred at 1000 rpm for 30 minutes at room temperature using magnetic stirring. This formulation was analyzed using SEM imaging as shown in FIG. 28. The liposomes were stored under refrigeration.

Figure 29:
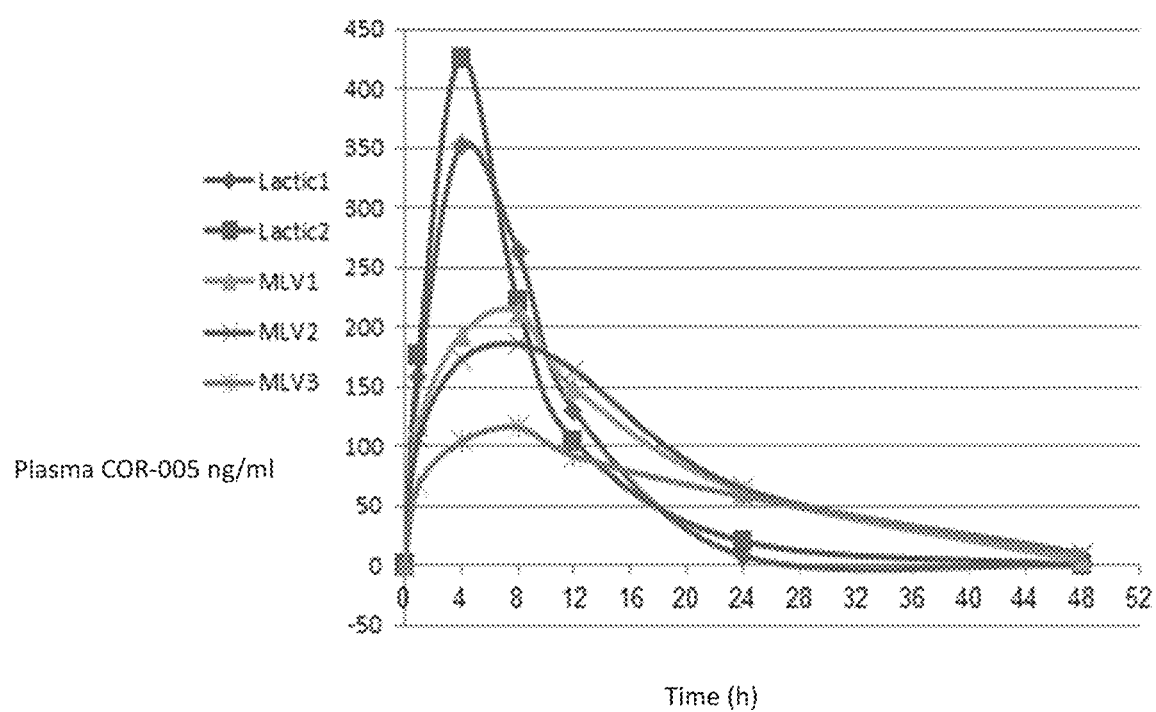
FIG. 29 shows the plasma concentration (ng/mL, vertical axis) of veldoreotide over time (hours, horizontal axis) in rats injected with veldoreotide acetate liposomes versus rats injected with veldoreotide acetate in a lactic acid vehicle.

Two rats were injected with veldoreotide acetate in the lactic acid vehicle of Example 3. Three SD® rats were injected with the veldoreotide acetate liposomes. Injections were made administered at about 4.5 mg/kg of veldoreotide acetate. Plasma samples were drawn at 1, 4, 8, 12, 24 and 48 hours and analyzed as discussed previously to determine the veldoreotide acetate plasma concentration in ng/mL. The data are shown in graphical form in FIG. 29.

Liposomes demonstrated a suitable delivery vehicle for sustained release of veldoreotide acetate with therapeutic concentrations (>1-5 ng/mL) for at least 48 hours which may correlate to a once weekly dosage form for humans. It may be understood that liposomes may be formed by any method known to those of skill in the art and that the ratio of veldoreotide acetate to the liposomal agent may range at least 1:5 to 1:20. In addition, any pharmaceutically acceptable carrier or diluent may be used.

Example 7

PLGA microspheres containing veldoreotide acetate were prepared. 500 mg of PLGA 50:50 (7-17 kDa) was dissolved in 5 mL dichloromethane oil phase). An aqueous solution contacting 50 mg of veldoreotide acetate in 1 ml of DDW prepared separately (inner aqueous phase). The first aqueous phase was emulsified into the oil phase (containing PLGA), using a high-speed homogenizer (Polytron) at 2-8° C. using different speeds and time durations to form water in oil primary emulsion. The primary emulsion was added (drop wise) into the 100 ml of external aqueous phase containing 1% PVA solution in PBS to form secondary emulsion. The rationale to dissolve the PVA in PBS was in order to reduce to minimum the leakage of veldoreotide acetate from the water to the external phase. The wet microspheres were then stirred at 1000 rpm for 2 h in ice to permit evaporation of DCM and solidification of microspheres. The wet microspheres were collected by centrifugation following three washing courses in PBS and then suspended in 6 ml of 2% mannitol and freeze dried. A sample of the dried microspheres was dissolved in DDW:Acetone 1:1 and the extracted amount of peptide was estimated by the naoVue spectrophotometer. The final drug load of veldoreotide acetate in microspheres was 6 weight % and the encapsulation efficiency (EE) % was 77%.

Embodiments of the pharmaceutical composition include:

A pharmaceutical composition comprising: a peptide or a pharmaceutically acceptable salt thereof, wherein the peptide is water soluble, but has low solubility in isotonic conditions; a pharmaceutically acceptable carrier or diluent; and an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions, wherein the pharmaceutically acceptable salt is selected from the group consisting of hydrochloride, hydrobromide, sulfate, phosphate, acetate, trifluoroacetate, citrate, oxalate, sulfonate, phosphonate, perchlorate, nitrate, formate, propioniate, gluconate, lactate, tartrate, pamoate, hydroxymaleate, pyruvate, phenylacetate, benzoate, p-aminobenzoate, p-hydroxybenzoate, methanesulfonate, ethanesulfonate, nitrite, hydroxyethanesulfonate, ethylenesulfonate, p-toluenesulfonate, naphthylsulfonate, sulfanilate, camphersulfonate, mandelate, o-methylmandelate, hydrogen-benzesulfonate, picrate, adipate, D-o-tolyltartrate, tartronate, α-toluate, (o, m, p)-toluate, napthylamine sulfonate, octanoate, palmitate, stearate, fatty acid salt, other mineral acid salt, and carboxylic acids; a pharmaceutically acceptable carrier or diluent; and an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions; a polymer; and optionally an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions; a polymer forming microspheres; and optionally an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions; a polymer forming microspheres; and optionally an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions; a polymer forming microspheres, wherein the polymer is PLGA; and optionally an excipient, wherein the excipient is a hydrophobic scavenger, a sugar or an amino acid.

A pharmaceutical composition comprising: a peptide or pharmaceutically acceptable salt thereof wherein the peptide or pharmaceutically acceptable salt thereof is veldoreotide or a pharmaceutically acceptable salt thereof; a pharmaceutically acceptable carrier or diluent; and an excipient, wherein the excipient is a hydrophobic scavenger, a sugar or an amino acid.

A pharmaceutical composition comprising: a peptide or pharmaceutically acceptable salt thereof, wherein the peptide or pharmaceutically acceptable salt thereof is veldoreotide or a pharmaceutically acceptable salt thereof, wherein the pharmaceutically acceptable salt is selected from the group consisting of hydrochloride, hydrobromide, sulfate, phosphate, acetate, trifluoroacetate, citrate, oxalate, malonate, salicylate, p-aminosalicylate, malate, fumarate, succinate, ascorbate, maleate, sulfonate, phosphonate, perchlorate, nitrate, formate, propioniate, gluconate, lactate, tartrate, pamoate, hydroxymaleate, pyruvate, phenylacetate, benzoate, p-aminobenzoate, p-hydroxybenzoate, methanesulfonate, ethanesulfonate, nitrite, hydroxyethanesulfonate, ethylenesulfonate, p-toluenesulfonate, naphthylsulfonate, sulfanilate, camphersulfonate, mandelate, o-methylmandelate, hydrogen-benzesulfonate, picrate, adipate, D-o-tolyltartrate, tartronate, α-toluate, (o, m, p)-toluate, napthylamine sulfonate, octanoate, palmitate, stearate, fatty acid salt, other mineral acid salt, and carboxylic acids; a pharmaceutically acceptable carrier or diluent; and an excipient, wherein the excipient is a hydrophobic scavenger, a sugar or an amino acid.

A pharmaceutical composition comprising: a peptide or pharmaceutically acceptable salt thereof wherein the peptide or pharmaceutically acceptable salt thereof is veldoreotide or a pharmaceutically acceptable salt thereof; a polymer; and optionally an excipient, wherein the excipient is a hydrophobic scavenger, a sugar or an amino acid.

A pharmaceutical composition comprising: a peptide or pharmaceutically acceptable salt thereof, wherein the peptide of pharmaceutically acceptable salt thereof is veldoreotide or a pharmaceutically acceptable salt thereof; a polymer forming microspheres; and optionally an excipient, wherein the excipient is a hydrophobic scavenger, a sugar or an amino acid.

A pharmaceutical composition comprising: veldoreotide or a pharmaceutically acceptable salt thereof, wherein the peptide is water soluble, but has low solubility in isotonic conditions; a polymer forming microspheres, wherein the polymer is PLGA; and optionally an excipient, wherein the excipient is a hydrophobic scavenger, a sugar or an amino acid.

A pharmaceutical composition comprising: a peptide or a pharmaceutically acceptable salt thereof, wherein the peptide is water soluble, but has low solubility in isotonic conditions; a polymer; and an excipient; wherein the pharmaceutical composition is a gel.

A pharmaceutical composition comprising: a peptide or a pharmaceutically acceptable salt thereof, wherein the peptide is water soluble, but has low solubility in isotonic conditions; an oil phase; an aqueous phase, wherein the peptide or a pharmaceutically acceptable salt thereof acts an an emulsifier; and optionally an excipient, wherein the excipient is a hydrophobic scavenger, a sugar or an amino acid; wherein the pharmaceutical composition forms an emulsion.

A pharmaceutical composition comprising: a peptide or a pharmaceutically acceptable salt thereof, wherein the peptide is water soluble, but has low solubility in isotonic conditions; a pharmaceutically acceptable carrier or diluent; and a liposomal agent forming liposomes; and optionally an excipient, wherein the excipient is a hydrophobic scavenger, a sugar or an amino acid.

Embodiments of any of the foregoing pharmaceutical compositions include:

The pharmaceutical composition wherein the peptide or pharmaceutically acceptable salt thereof is: a cyclic peptide; or a peptide amphiphile; or a somatostatin analog; or a cyclic somatostatin analog; or a conformationally-constrained, backbone-cyclic peptide; or a conformationally-constrained, backbone-cyclic somatostatin analog; or a conformationally-constrained, backbone-cyclic, single amine somatostatin analog; or an ionic, water soluble surfactant.

The pharmaceutical composition wherein the pharmaceutically acceptable salt is: acetate; or selected from the group consisting of hydrochloride, hydrobromide, sulfate, phosphate, acetate, trifluoroacetate, citrate, oxalate, malonate, salicylate, p-aminosalicylate, malate, fumarate, succinate, ascorbate, maleate, sulfonate, phosphonate, perchlorate, nitrate, formate, propioniate, gluconate, lactate, tartrate, pamoate, hydroxymaleate, pyruvate, phenylacetate, benzoate, p-aminobenzoate, p-hydroxybenzoate, methanesulfonate, ethanesulfonate, nitrite, hydroxyethanesulfonate, ethylenesulfonate, p-toluenesulfonate, naphthylsulfonate, sulfanilate, camphersulfonate, mandelate, o-methylmandelate, hydrogen-benzesulfonate, picrate, adipate, D-o-tolyltartrate, tartronate, α-toluate, (o, m, p)-toluate, napthylamine sulfonate, octanoate, palmitate, stearate, fatty acid salt, other mineral acid salt, and carboxylic acids.

The pharmaceutical composition wherein the excipient is the sugar, and wherein the sugar is: a saccharide; or selected from the group consisting of monosaccharides, disaccharides, and polysaccharides; or a cyclic polysaccharide; or a cyclodextrin; or a β-cyclodextrin; or hydroxypropyl-β-cyclodextrin; or a monosaccharide; or dextrose; or at a concentration of about 2.5% wt to about 5.0% wt based on the total weight of the composition.

The pharmaceutical composition, wherein the excipient is the amino acid and is a natural amino acid, and wherein the amino acid is lysine or arginine; or the hydrochloride salt of an amino acid; or L-lysine hydrochloride or L-arginine hydrochloride.

The pharmaceutical composition wherein the excipient is the hydrophobic scavenger, and wherein the hydrophobic scavenger has at least one free amine group.

The pharmaceutical composition wherein the pharmaceutically acceptable carrier or diluent is: selected from the group consisting of isotonic acetate buffer, lactic acid, saline, and phosphate buffered saline; or saline; or at a concentration of about 0.45% by weight of the composition.

The pharmaceutical composition wherein the polymer: is biocompatible; or forms a matrix; or forms particles; or forms microspheres.

The pharmaceutical composition wherein the microspheres: have increased porosity as compared to microspheres formulated without the excipient; or have increased surface area as compared to microspheres formulated without the excipient; or have increased peptide release as compared to microspheres formulated without the excipient; or have increased release of the peptide during a first 24-hour period after injection of the pharmaceutical composition in a patient as compared to microspheres formulated without the excipient; or exhibit a sustained release profile for at least one week after injection of the pharmaceutical composition in a patient; or exhibit a sustained release profile for at least two weeks after injection of the pharmaceutical composition in a patient; or exhibit a sustained release profile for at least four weeks after injection of the pharmaceutical composition in a patient.

The pharmaceutical composition wherein the polymer is poly lactic-co-glycolic acid (PLGA); or wherein the poly lactic co-glycolic acid (PLGA) comprises a 50:50 ratio of lactic acid to glycolic acid.

The pharmaceutical composition wherein the polymer encapsulates: the peptide or pharmaceutically acceptable salt thereof; or the excipient; or both the peptide or pharmaceutically acceptable salt thereof and the excipient.

The pharmaceutical composition wherein the polymer has an average molecular weight between about 7 and about 17 kilodaltons; or has a molecular weight between about 38 and about 54 kilodaltons.

The pharmaceutical composition wherein the peptide and the excipient are co-localized within the polymer.

The pharmaceutical composition wherein the pharmaceutically acceptable salt is veldoreotide acetate.

The pharmaceutical composition wherein the polymer encapsulates the veldoreotide or pharmaceutically acceptable salt thereof; or the excipient; or both the peptide or pharmaceutically acceptable salt thereof and the excipient; or both the veldoreotide or pharmaceutically acceptable salt thereof and the excipient.

The pharmaceutical composition wherein the veldoreotide and the excipient are co-localized within the polymer.

The pharmaceutical composition wherein the microspheres encapsulate the veldoreotide or pharmaceutically acceptable salt thereof; or the excipient; or both the veldoreotide or pharmaceutically acceptable salt thereof and the excipient.

The pharmaceutical composition wherein the polymer is a viscosity modifying agent; or is a thickener; or is a gelling agent (gellant); or has an average viscosity of 1500-3000 cps in a 1% aqueous solution; or is a cellulose gum or a derivative thereof; or is carboxymethylcellulose; or interacts with the peptide or pharmaceutically acceptable salt thereof; or interacts with the peptide and a cyclodextrin to form a gel.

The pharmaceutical composition, wherein the pharmaceutical composition is injectable by a small gauge need as small as 27G.

The pharmaceutical composition which is an emulsion wherein the oil phase comprises a pharmaceutically acceptable oil; or cottonseed oil; or wherein the aqueous phase comprises water; or the emulsion is a water-in-oil emulsion; or a ratio of the oil phase to the aqueous phase is between about 60:40 to 99.9:0.1; or between about 70:30 to 99.9:0.1; or between about 80:20 and 99.9:0.1; or between about 90:10 and 99.9:0.1; or between about 95:5 and 99.9:0.1; or between about 50.1:49.9 to 90:10; or between about 50.1:49.9 to 80:20; or between about 50.1:49.9 to 70:30; or between about 50.1:49.9 to 60:40; or between about 60:40 and 90:10; or between about 70:30 and 80:20; or about 80:20.

The pharmaceutical composition wherein the liposomal agent is: phosphatidylcholine or a derivative thereof; or DMPC.

Other embodiments include:

A method for reducing injection site side effects in a patient as compared to injection without the excipient comprising: (a) formulating the pharmaceutical composition of any the embodiments above with the excipient; and (b) administering the pharmaceutical composition to said patient by injection.

A method for increasing the bioavailability of the peptide or pharmaceutically acceptable salt thereof as compared to injection without the excipient comprising: (a) formulating the pharmaceutical composition of any the embodiments above with the excipient; and (b) administering the pharmaceutical composition to said patient by injection.

The method wherein the peptide or pharmaceutically acceptable salt thereof is administered at a therapeutically effective dose.

A method for formulating the pharmaceutical composition of any one of the embodiments above, comprising: (a) Mixing the peptide or pharmaceutically acceptable salt thereof and the excipient; and (b) Slowly adding the polymer.

A method for treating a disease comprising the step of administering the pharmaceutical composition of any one of the embodiments above to a patient in need thereof.

The method wherein the disease is selected from the group consisting of cancer, type 2 diabetes, acromegaly, metabolic disorders, endocrine disorders, exocrine disorders, and hormone-related tumors.

The method wherein the pharmaceutical composition is administered by injection; or subcutaneous injection; or intravenous injection.

Specific embodiments of the pharmaceutical composition of embodiment 1 include the following:

2. The pharmaceutical composition wherein the pharmaceutically acceptable salt is selected from the group consisting of hydrochloride, hydrobromide, sulfate, phosphate, acetate, trifluoroacetate, citrate, oxalate, malonate, salicylate, p-aminosalicylate, malate, fumarate, succinate, ascorbate, maleate, sulfonate, phosphonate, perchlorate, nitrate, formate, propioniate, gluconate, lactate, tartrate, pamoate, hydroxymaleate, pyruvate, phenylacetate, benzoate, p-aminobenzoate, p-hydroxybenzoate, methanesulfonate, ethanesulfonate, nitrite, hydroxyethanesulfonate, ethylenesulfonate, p-toluenesulfonate, naphthylsulfonate, sulfanilate, camphersulfonate, mandelate, o-methylmandelate, hydrogen-benzesulfonate, picrate, adipate, D-o-tolyltartrate, tartronate, α-toluate, (o, m, p)-toluate, napthylamine sulfonate, octanoate, palmitate, stearate, fatty acid salt, other mineral acid salt, and carboxylic acids.

3. The pharmaceutical composition of embodiment 1 or 2 wherein the pharmaceutically acceptable salt is the acetate of the peptide.

4. The pharmaceutical composition of any of embodiments 1-3, wherein the pharmaceutically acceptable carrier or diluent is selected from the group consisting of isotonic acetate buffer, normal saline of 0.9% NaCl in water or 0.45% NaCl in water, water for injection, isotonic 5% or 2.5% dextrose, isotonic lactic acid and phosphate buffered saline.

5. The pharmaceutical composition of any of embodiments 1-4, wherein the pharmaceutically acceptable carrier is saline of 0.9% NaCl in water or 0.45% NaCl in water.

6. The pharmaceutical composition of any of embodiments 1 to 5, wherein the pharmaceutically acceptable carrier or diluent is normal saline (0.9% NaCl in water).

7. The composition of any of embodiments 1-6 wherein the peptide or the pharmaceutically acceptable salt thereof is veldoreotide or veldoreotide acetate, respectively.

8. The pharmaceutical composition of any of embodiments 1-7, wherein the peptide is veldoreotide.

9. The composition of any of embodiments 1-8 wherein the pharmaceutically acceptable salt of the peptide is veldoreotide acetate.

10. The pharmaceutical composition of any of embodiments 1-9, wherein the excipient is the cyclic polysaccharide.

11. The pharmaceutical composition of embodiment 10, wherein the cyclic polysaccharide is hydroxypropyl-β-cyclodextrin.

12. The pharmaceutical composition of embodiment 11, wherein the mass ratio of the hydroxypropyl-β-cyclodextrin to peptide or pharmaceutically acceptable salt thereof is from 1:1 to 20:1.

13. The pharmaceutical composition of embodiment 12, wherein the mass ratio of hydroxypropyl-β-cyclodextrin to peptide or pharmaceutically acceptable salt thereof is 1:1.

14. The pharmaceutical composition of embodiment 12, wherein the mass ratio of the hydroxypropyl-β-cyclodextrin to peptide or the pharmaceutically acceptable salt is 20:1.

15. The pharmaceutical composition of any of embodiments 1-9, wherein the excipient is dextrose.

16. The pharmaceutical composition of embodiment 15, wherein the mass ratio of dextrose to peptide or pharmaceutically acceptable salt thereof is from 1:1 to about 5:1; preferably 5:1.

17. The pharmaceutical composition of embodiment 16, wherein the mass ratio of dextrose to peptide or pharmaceutically acceptable salt thereof is 5:1.

18. The pharmaceutical composition of any of embodiments 1-10 comprising:
veldoreotide acetate; a pharmaceutically acceptable carrier or diluent selected from the group consisting of isotonic acetate buffer, isotonic lactic acid, water, saline of 0.9% NaCl in water or 0.45% NaCl in water, water for injection, isotonic dextrose 5% or 2.5%, and phosphate buffered saline; and hydroxypropyl-β-cyclodextrin (HPBCD).

19. The pharmaceutical composition of embodiment 18, wherein the mass ratio of hydroxypropyl-β-cyclodextrin to veldoreotide acetate is from 1:1 to 25:1.

20. The pharmaceutical composition of embodiment 19, wherein the mass ratio of hydroxypropyl-β-cyclodextrin to veldoreotide acetate is 1:1.

21. The pharmaceutical composition of embodiment 19, wherein the mass ratio of hydroxypropyl-β-cyclodextrin to veldoreotide acetate is 25:1.

22. The pharmaceutical composition of any of embodiments 18-21, wherein the pharmaceutically acceptable carrier or diluent is saline of 0.9% NaCl in water or 0.45% NaCl in water for injection.

23. The pharmaceutical composition of any of embodiments 1, 2, 3, 4, 5, 6, 7, 8, or 15 comprising: veldoreotide acetate; a pharmaceutically acceptable carrier or diluent selected from the group consisting of isotonic acetate buffer, water for injection, saline of 0.9% NaCl in water or 0.45% NaCl in water for injection, isotonic lactic acid, isotonic dextrose 5% or 2.5%, and phosphate buffered saline; and dextrose.

24. The pharmaceutical composition of embodiment 23, wherein the mass ratio of dextrose to veldoreotide acetate is from 1:1 to about 5:1.

25. The pharmaceutical composition of embodiment 23 or 24, wherein the mass ratio of dextrose to veldoreotide acetate is 5:1.

26. The pharmaceutical composition of any of embodiments 23-25, wherein the pharmaceutically acceptable carrier or diluent is saline of 0.9% NaCl in water or 0.45% NaCl in water for injection.

27. The pharmaceutical composition of any of embodiments 1-26 comprising:
a peptide or a pharmaceutically acceptable salt thereof, wherein the peptide or the pharmaceutically acceptable salt thereof is freely soluble in water, but has slight solubility in physiological conditions; an excipient, wherein the excipient is a cyclic polysaccharide or dextrose or a combination thereof; and
a polymeric microsphere, wherein the peptide or the pharmaceutically acceptable salt thereof and the excipient are encapsulated in the polymeric microsphere.

28. The pharmaceutical composition of embodiment 27 wherein the polymeric microsphere comprises poly(lactic-co-glycolic acid) (PLGA).

29. The pharmaceutical composition of embodiment 27 or 28 wherein the excipient is dextrose.

30. The pharmaceutical composition of any of embodiments 27-29 wherein the amount of dextrose is from about 0.1 weight % to about 1.0 weight % based on the total weight of the polymeric microsphere.

31. The pharmaceutical composition of any of embodiments 27-30 comprising: veldoreotide acetate; dextrose; and a polymeric microsphere, wherein the polymeric microsphere comprises poly(lactic-co-glycolic acid) (PLGA), and wherein the veldoreotide and the dextrose are encapsulated in the polymeric microsphere.

32. The pharmaceutical composition of embodiment 27 or 28 wherein the excipient is the cyclic polysaccharide.

33. The pharmaceutical composition of any of embodiments 27, 28, or 32 wherein the cyclic polysaccharide is hydroxypropyl-β-cyclodextrin (HPBCD).

34. The pharmaceutical composition of any of embodiments 27, 28, 32 or 33 wherein the amount of HPBCD is from about 2 weight % to about 20 weight % based on the total polymer (PLGA) weight of the composition.

35. The pharmaceutical composition of any of embodiments 27, 28, 32, 33 or 34 comprising: veldoreotide acetate; hydroxypropyl-β-cyclodextrin (HPBCD); and a polymeric microsphere, wherein the polymeric microsphere comprises poly(lactic-co-glycolic acid) (PLGA), and wherein the veldoreotide acetate and the HPBCD are encapsulated in the polymeric microsphere.

36. The pharmaceutical composition of embodiment 27 or 28 comprising: veldoreotide acetate; dextrose and HPBCD; and a polymeric microsphere, wherein the polymeric microsphere comprises poly(lactic-co-glycolic acid) (PLGA), and wherein the veldoreotide, dextrose and HPBCD are encapsulated in the polymeric microsphere.

37. The pharmaceutical composition of any of embodiments 27-36, wherein the diameter of the polymeric microsphere is from about 10 microns to about 100 microns, more preferably from about 10 microns to about 30 microns.

Embodiment 38. A process for manufacturing polymeric microspheres comprising the steps of:
(i) mixing an excipient comprising a cyclic polysaccharide or dextrose or a combination thereof, and a peptide or a pharmaceutically acceptable salt thereof in water to form a first aqueous mixture, wherein the peptide or the pharmaceutically acceptable salt thereof is freely soluble in deionized water with a solubility in deionized water of from 100 to 350 mg/ml but is slightly soluble under physiological conditions with a solubility of 2-3 mg/ml and the peptide or the pharmaceutically acceptable salt precipitates by salting out at a concentration greater than 3 mg/ml;
(ii) mixing a polymer in organic solvent such as dichloromethane to form a polymeric solution;
(iii) mixing the first aqueous mixture in the polymeric organic solution to form a first dispersion mixture comprising a water in oil primary emulsion;
(iv) mixing polyvinyl alcohol (PVA) in an amount of 0.1 to 3 weight % in phosphate buffer saline or in saline to form a second aqueous mixture;
(v) mixing the primary emulsion in the second aqueous mixture of PVA to form a double emulsion of water-in-oil-in-water to provide a secondary dispersion mixture;
(vi) allowing the organic solvent in the secondary dispersion mixture to evaporate to form solid polymeric microspheres, wherein the peptide or pharmaceutically acceptable salt thereof is encapsulated in the polymeric microspheres;
(vii) washing and isolating the polymeric microspheres; and
(viii) drying the microspheres under control conditions with or without the addition of a surfactant and mannitol mixture during the drying process.

39. The process of embodiment 38 wherein the excipient is a cyclic polysaccharide and wherein the mass ratio of the cyclic polysaccharide to the peptide or the pharmaceutically acceptable salt thereof is from about 1:2 to about 1:20.

40. The process of embodiment 39 wherein the cyclic polysaccharide is hydroxypropyl-β-cyclodextrin (HPBCD).

41. The process of embodiment 39 wherein the mass ratio of HPBCD to the peptide or pharmaceutically acceptable salt thereof is from about 1:2 to about 1:4.

42. The process of embodiment 38 wherein the excipient is dextrose and the mass ratio of dextrose to the peptide or pharmaceutically acceptable salt thereof is from 1:4 to 1:16.

43. The process of embodiment 42 wherein the mass ratio of dextrose to the peptide or pharmaceutically acceptable salt thereof is from 1:6 to 1:10.

44. The process of embodiment 42 or 43 wherein the mass ratio of dextrose to the peptide or pharmaceutically acceptable salt thereof is 1:8.

45. The process of any of embodiments 38-44 wherein the peptide or the pharmaceutically acceptable salt thereof is veldoreotide or veldoreotide acetate, respectively.

46. The process of any of embodiments 38-45 wherein the polymeric solution comprises poly(lactic-co-glycolic acid) (PLGA).

Embodiment 47. An extended-release pharmaceutical composition produced by the process of any of embodiments 38-46.

Embodiment 48. A composition for manufacturing polymeric microspheres comprising: veldoreotide or a pharmaceutically acceptable salt thereof; an excipient comprising a cyclic polysaccharide or dextrose or a combination thereof; and a polymer solution.

49. The composition of embodiment 48 wherein the excipient is the cyclic polysaccharide hydroxypropyl-β-cyclodextrin (HPBCD).

50. The composition of embodiment 49 wherein the mass ratio of HPBCD to veldoreotide or pharmaceutically acceptable salt thereof is from about 1:1 to about 1:20; or from about 1:2 to about 1:4; or about 1:4.

51. The composition of embodiment 48 wherein the excipient is dextrose.

52. The composition of embodiment 51 wherein the mass ratio of dextrose to veldoreotide or pharmaceutically acceptable salt thereof is from 1:4 to 1:16; or from 1:6 to 1:10; or is 1:8.

53. The composition of any of embodiments 48-52 wherein the polymer solution comprises poly(lactic-co-glycolic acid) (PLGA).

Embodiment 54. A method for treating a disease or condition selected from the group consisting of acromegaly, acromegaly cancer, carcinoid cancer, Cushings Syndrome, SST-R5 expressing tumors, type 2 diabetes, hyperglycemia, and hormone-related tumors comprising the step of administering the pharmaceutical composition of any one of embodiments 1-37 to a patient with said disease or condition.

55. The method of embodiment 54, wherein the pharmaceutical composition is administered by injection.

56. The method of embodiment 54, wherein the pharmaceutical composition is administered by subcutaneous injection.

57. The method of embodiment 54, wherein the pharmaceutical composition is administered by intramuscular injection.

58. The method of any of embodiments 54-57, wherein the pharmaceutical composition is dispersed in a pharmaceutical acceptable diluent that composed of surfactant and mannitol in isotonic solution ready for injection.

Although the present invention has been described in terms of specific embodiments, changes and modifications can be made without departing from the scope of the invention which is intended to be defined only by the scope of the claims.

What is claimed is:
1. A pharmaceutical composition comprising:
veldoreotide acetate;
an excipient, wherein the excipient comprises a monosaccharide, a disaccharide, polysaccharide, cyclic polysaccharide, cyclic oligosaccharide, cyclodextrin or β-cyclodextrin;
and a polymeric microsphere, wherein veldoreotide acetate-is encapsulated in the polymeric microsphere, and wherein the surface area of the polymeric microsphere is from about 7 m²/g to about 12 m²/g.

2. The pharmaceutical composition of claim 1, wherein the diameter of the polymeric microsphere is from about 10 microns to about 100 microns.

3. The pharmaceutical composition of claim 1, wherein the polymeric microsphere comprises poly(lactic-co-glycolic acid) (PLGA).

4. The pharmaceutical composition of claim 1, wherein the microsphere comprises a plurality of internal voids separated by thin interstitial boundaries.

5. The pharmaceutical composition of claim 1, wherein the microsphere further comprises an excipient selected from the group consisting of a sugar, an amino acid, and nicotinamide.

6. The pharmaceutical composition of claim 1, wherein the amount of monosaccharide is from about 0.1 weight % to about 1.0 weight % based on the total weight of the polymeric microsphere.

7. The pharmaceutical composition of claim 1, wherein the excipient comprises lysine, arginine, or a pharmaceutically acceptable salt thereof.

8. A process for manufacturing polymeric microspheres comprising the steps of:
(i) mixing an excipient comprising a sugar or an amino acid, and veldoreotide or a pharmaceutically acceptable salt thereof in water to form a first aqueous mixture;
(ii) mixing a polymer in organic solvent to form a polymeric solution;
(iii) mixing the first aqueous mixture in the polymeric solution to form a first dispersion mixture comprising a water-in-oil primary emulsion;
(iv) mixing polyvinyl alcohol (PVA) in phosphate buffered saline or in saline to form a second aqueous mixture;
(v) mixing the primary emulsion in the second aqueous mixture of PVA to form a water-in-oil-in-water double emulsion thereby providing a secondary dispersion mixture; and
(vi) allowing the organic solvent in the secondary dispersion mixture to evaporate to form polymeric microspheres comprising veldoreotide or pharmaceutically acceptable salt thereof.

9. The process of claim 8, wherein the pharmaceutically acceptable salt of veldoreotide is veldoreotide acetate.

10. The process of claim 8, wherein the polymeric solution comprises poly(lactic-co-glycolic acid) (PLGA).

11. The process of claim 8, wherein the excipient comprises a monosaccharide, a disaccharide, polysaccharide, cyclic polysaccharide, cyclic oligosaccharide, cyclodextrin or β-cyclodextrin.

12. The process of claim 11, wherein the excipient comprises a monosaccharide.

13. The process of claim 12, wherein the mass ratio of monosaccharide to veldoreotide or pharmaceutically acceptable salt thereof is from 1:4 to 1:16.

14. The process of claim 12, wherein the mass ratio of monosaccharide to veldoreotide or pharmaceutically acceptable salt thereof is from 1:6 to 1:10.

15. The process of claim 12, wherein the mass ratio of monosaccharide to veldoreotide or pharmaceutically acceptable salt thereof is 1:8.

16. The process of claim 11, wherein the excipient comprises a cyclodextrin.

17. The process of claim 16 wherein the mass ratio of cyclodextrin to veldoreotide or pharmaceutically acceptable salt thereof is from 1:1 to 1:8.

18. The process of claim 16, wherein the mass ratio of cyclodextrin to veldoreotide or pharmaceutically acceptable salt thereof is from 1:2 to 1:4.

19. The process of claim 8, wherein the excipient comprises lysine, arginine, or a pharmaceutically acceptable salt thereof.

* * * * *